(12) United States Patent
Finkbeiner et al.

(10) Patent No.: US 9,359,445 B2
(45) Date of Patent: Jun. 7, 2016

(54) COMPOSITIONS AND METHODS FOR TREATING NEUROLOGICAL DISORDERS

(71) Applicant: The J. David Gladstone Institutes, San Francisco, CA (US)

(72) Inventors: Steven M. Finkbeiner, Corte Madera, CA (US); Vikram Ramnath Rao, San Francisco, CA (US); Sarah Rosemary Carter, Arlington, VA (US); Eva Suzanne LaDow, San Francisco, CA (US); Hong Joo Kim, Memphis, TN (US); Matthew Campioni, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 13/625,597

(22) Filed: Sep. 24, 2012

(65) Prior Publication Data

US 2013/0095113 A1 Apr. 18, 2013

Related U.S. Application Data

(63) Continuation-in-part of application No. PCT/US2011/029806, filed on Mar. 24, 2011.

(60) Provisional application No. 61/317,598, filed on Mar. 25, 2010.

(51) Int. Cl.
*C07K 16/40* (2006.01)
*A61K 31/7088* (2006.01)
*C12N 15/113* (2010.01)

(52) U.S. Cl.
CPC ............. *C07K 16/40* (2013.01); *A61K 31/7088* (2013.01); *C12N 15/1137* (2013.01); *C07K 2317/77* (2013.01); *C12N 2310/14* (2013.01); *C12N 2310/531* (2013.01)

(58) Field of Classification Search
CPC ............... A61K 31/7088; C07K 16/40; C07K 2317/77; C12N 15/1137; C12N 2310/14; C12N 2310/531
USPC ............ 424/146.1, 158.1, 450; 435/325, 350, 435/375; 514/44 A; 536/24.5; 530/389.1, 530/388.1
See application file for complete search history.

(56) References Cited

U.S. PATENT DOCUMENTS

| | | | | |
|---|---|---|---|---|
| 6,124,272 | A * | 9/2000 | Monia et al. | 514/44 A |
| 2004/0121407 | A1 * | 6/2004 | Distefano et al. | 435/7.1 |
| 2006/0004043 | A1 | 1/2006 | Bhagwat et al. | |
| 2009/0099178 | A1 | 4/2009 | Bhagwat et al. | |
| 2009/0175852 | A1 | 7/2009 | Ciavarri et al. | |
| 2009/0247519 | A1 * | 10/2009 | Raynham | C07D 215/46 514/234.5 |
| 2009/0258814 | A1 * | 10/2009 | Brady et al. | 514/2 |

FOREIGN PATENT DOCUMENTS

| | | | | |
|---|---|---|---|---|
| WO | WO 98/24894 | | 12/1997 | |
| WO | WO 2007/002433 | | 1/2007 | |
| WO | WO 2007088401 | A1 * | 8/2007 | ........... A61K 31/416 |
| WO | WO 2009/147246 | | 12/2009 | |
| WO | WO 2009147246 | A1 * | 12/2009 | |
| WO | WO 2011/104411 | | 2/2011 | |

OTHER PUBLICATIONS

Zhang et al. ((2005) J. Biol. Chem. 280:19036-19044).*
Czauderna et al. Nucleic Acids Research, 2003, vol. 31, No. 11 p. 2705-2716.*
Lim et al. Bull. Korean Chem. Soc. 2006, vol. 27, No. 9 1371.*
Lee, et al., "Growth Inhibitory and Anti-Tumor Activities of OSU-03012, a Novel PDK-1 Inhibitor, on Vestibular Schwannoma and Malignant Schwannoma Cells", Eur. J. Cancer, 2009, vol. 45, No. 9, pp. 1709-1720.
Soriano et al., "Mice Deficient in Mac-1 (CD11b/CD18) Are Less Susceptible to Cerebral Stroke", Stroke, 1999, vol. 30, pp. 134-139.
Amadesi et al., "Protein Kinase Disoforms are Expressed in Rat and Mouse Primary Sensory Neurons and are Activated by Agonists of Protease-Activated Receptor 2", Journal of Comparative Neurology, May 2009, 516(2):141-156.
Bisbal et al., "Protein Kinase D Regulates trafficking of Dendritic Membrane Proteins in Developing Neurons", Journal of Neuroscience, Sep. 2008, 28(37):9297-9308.
Carter et al., "The Roles of the Novel Kinase PKD1 and the AKAP Yotiao in NMDA Receptor Signaling", Ph. D. Thesis, 2007, University of California, San Francisco.
Fielitz et al., "Requirement of Protein Kinase D1 for Pathological Cardiac Remodeling", Proceedings of the National Academy of Sciences, Feb. 2008, 105(8):3059-3063.
Kim et al., "Protein Kinase D1 Regulates AMPAR Trafficking and Arc Protein Levels in Response to Glutamatergic Signaling", Abstracts of the Annual Meeting of the Society for Neuroscience, Nov. 2008, 39:Abstract.
Kim et al., "Protein Kinase D1 Regulates HDAC-Dependent Arc Transcription in Response to mGluR Activation", Abstracts of the Annual Meeting of the Society for Neuroscience, Oct. 2009, 39:Abstract.
Zhu et al., "Interaction Between Protein Kinase D1 and Transient Receptor Potential V1 in Primary Sensory Neurons is involved in Heat Hypersensitivity", Pain, Jul. 2008, 137(3):574-588.
Jellinger; "Neuropathological Spectrum of Synucleinopathies"; Movement Disorders; vol. 18, No. 6, pp. S2-S12 (2003).
Manzoni, et al.; "Dysfunction of the autophagy/lysosomal degradation pathway is a shared feature of the genetic synucleinopathies"; The FASEB Journal; vol. 27, pp. 3424-3429 (Sep. 2013).
Marti, et al.; "Clinical Overview of the Synucleinopathies"; Movement Disorders; vol. 18, No. 6, pp. S21-S27 (2003).
Puschmann, et al.; "Synucleinopathies from bench to bedside"; Parkinsonism and Related Disorders; vol. 18S1, pp. S24-S27 (2012).

* cited by examiner

*Primary Examiner* — Janet Epps-Smith
(74) *Attorney, Agent, or Firm* — Michael B. Rubin; Bozicevic, Field & Francis LLP

(57) ABSTRACT

The present disclosure provides methods for treating neurological disorders, generally involving modulating protein kinase D1 (PKD1) activity levels in a neuron or glial cell in an individual in need thereof. The present disclosure provides antibodies specific for PKD1. The present disclosure provides a genetically modified non-human mammal deficient in PKD1 activity.

5 Claims, 24 Drawing Sheets

A
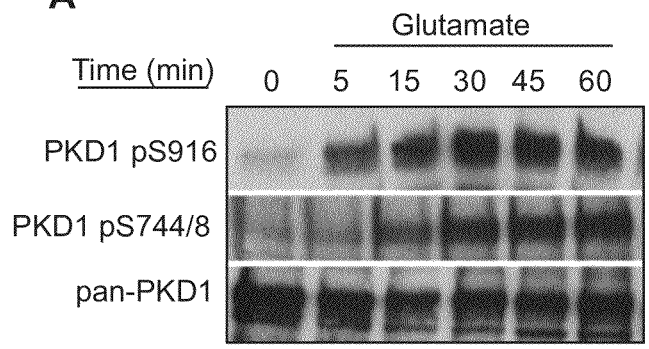
B
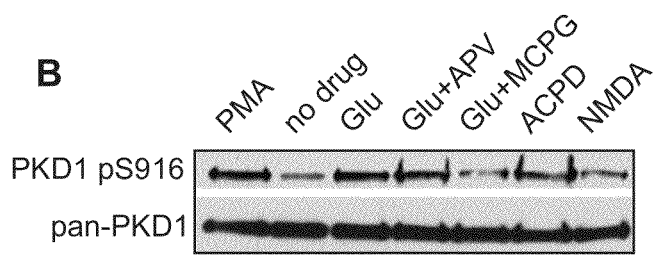
C
Activation of PLC
    U73122
↓
Activation of PKC
    GF1
    Gö6976
    Gö6983
↓
Activation of PKD
    Gö6976
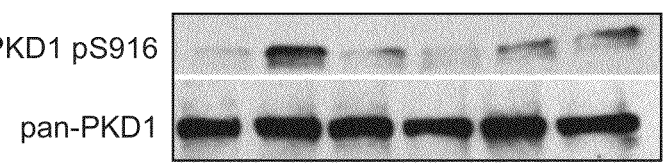
FIG. 2

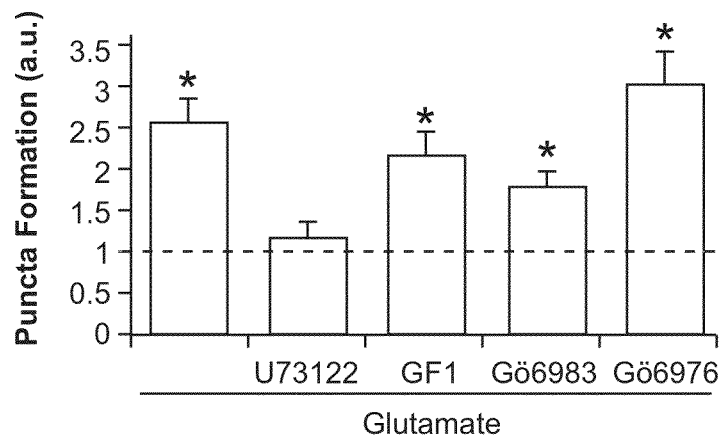
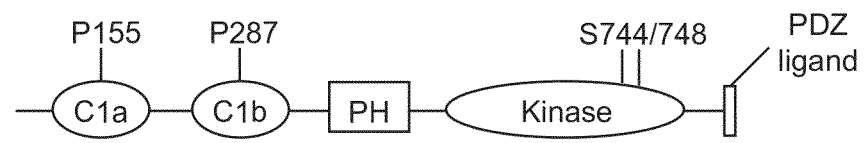
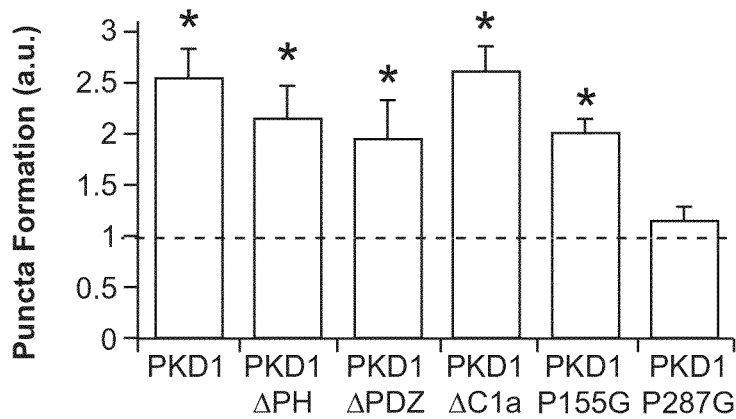
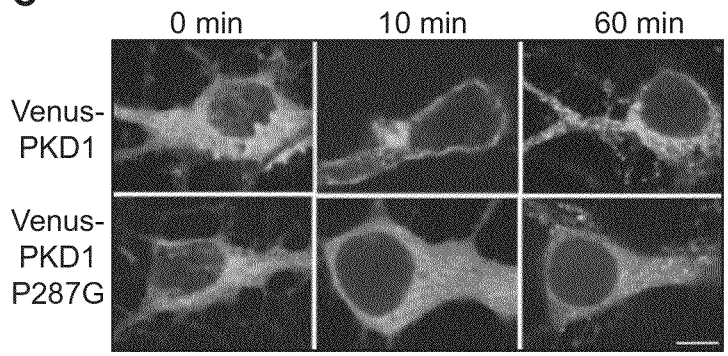
FIG. 4

NP_002733
*Homo sapiens* PKD1

```
  1 msappvlrpp spllpvaaaa aaaaaalvpg sgpgpapfla pvaapvggis fhlqiglsre
 61 pvllqdssg dyslahvrem acsivdqkfp ecgfygmydk illfrhdpts enilqlvkaa
121 sdiqegdlie vvlsasatfe dfqirphalf vhsyrapafc dhcgemlwgl vrqglkcegc
181 glnyhkrcaf kipnncsgvr rrlsnvslt gvstirtssa elstsapdep llqkspsesf
241 igrekrsnsq syigrpihld kilmskvkvp htfvihsytr ptvcqyckkl lkglfrqglq
301 ckdcrfnchk rcapkvpnnc lgevtingdl lspgaesdvv meegsddnds ernsglmddm
361 eeamvqdaem amaecqndsg emqdpdpdhe danrtispst snniplmrvv qsvkhtkrks
421 stvmkegwmv hytskdtlrk rhywrldskc itlfqndtgs rrykeiplse ilslepvkts
481 alipnganph cfeittanvv yvvgenvvnp sspspnnsvl tsgvgadvar mweiaiqhal
541 mpvipkgssv gtgtnlhrdi svsisvsncq iqenvdistv yqifpdevlg sgqfgivygg
601 khrktgrdva ikiidklrfp tkqesqlrne vailqnlhhp gvvnlecmfe tpervfvvme
661 klhgdmlemi lssekgrlpe hitkfllitqi lvalrhlhfk nivhcdlkpe nvllasadpf
721 pqvklcdfgf ariigeksfr rsvvgtpayl apevlrnkgy nrsldmwsvg vilyvslsgt
781 fpfnededih dqiqnaafmy ppnpwkeish eaidlinnll qvkmrkrysv dktlshpwlq
841 dyqtwldlre leckigeryi thesddlrwe kyageqglqy pthlinpsas hsdtpeteet
901 emkalgervs il (SEQ ID NO:1)
```

FIG. 11

GenBank NM_002742; 2739 bp;
*Homo sapiens*; PKD1 mRNA

```
   1 atgagcgccc ctccgtcct gcggccgccc agtccgctgc tgcccgtggc ggcggcagct
  61 gccgcagcgg cgccgcact ggtcccaggg tccgggcccg ggcccgcgcc gttcttggct
 121 cctgtcgcgg cccgtcgg gggcatctcg ttccatctgc agatcggcct gagccgtgag
 181 ccggtgctgc tgctgcagga ctcgtccgg gactacagcc tggcgcacgt ccgcgagatg
 241 gcttgctcca ttgtcgacca gaagttccct gaatgtggtt tctacggaat gtatgataag
 301 atcctgcttt ttcgccatga ccctacctct gaaaacatcc ttcagctggt gaaagcggcc
 361 agtgatatcc aggaaggcga tcttattgaa gtggtcttgt cagcttccgc cacctttgaa
 421 gactttcaga ttcgtcccca cgctctcttt gttcattcat acagagctcc agctttctgt
 481 gatcactgtg gagaaatgct gtgggggctg gtacgtcaag gtcttaaatg tgaaggtgt
 541 ggtctgaatt accataagag atgtgcattt aaaataccca cggtgtgagg
 601 cggagaaggc tctcaaacgt ttccctcact gggtcagca ccatccgcac atcatctgct
 661 gaactctcta caagtgcccc tgatgagccc cttctgcaaa aatcaccatc agagtcgttt
 721 attggtcgag agaagaggtc aaatctcaa tcatacattg gacgaccaat tcaccttgac
 781 aagattttga tgtctaaagt taaagtgccg caagaagctt ctgaagggc ttttcaggca gggcttgcag
 841 cccacagtgt gccagtactg caagaagctg cagaagctt ctgaagggc ttttcaggca aaacaactgc
 901 tgcaaagatt gcagattcaa ctgccataaa cgttgtgcac cgaaagtacc tgatgtggtc
 961 cttggcgaag tgaccattaa tggagatttg cttagccctg gggcagagtc ggatgatatg
1021 atggaagaag ggagtgatga caatgatagt gaaaggaaca gtgggctcat ggatgatatg
1081 gaagaagcaa tggtccaaga tgcagagatg gcaatggcag agtgccagaa cgacagtggc
1141 gagatgcaag atccagaccc agaccacgag gagggtagtg gacgccaaca gaaccatcag tccatcaaca
1201 agcaacaata tcccactcat gagggtagtg cagtctgtca cactacacca aacacacgaa gaggaaaagc
1261 agcacagtca tgaagaaagg atggatggtc tagcaaatgt ttcagaatga gctgcggaaa
1321 cggcactatt ggagattgga tagcaaatgt attacctct ttcagaatga cacaggaagc
1381 aggtactaca aggaaattcc tttatctgaa attttgtctc tggaaccagt aaaaacttca
1441 gctttaattc ctaatggggc caatcctcat tgttttcgaaa tcactacggc aaatgtagtg
```

FIG. 12A

```
1501 tattatgtgg gagaaaatgt ggtcaatcct tccagcccat caccaaataa cagtgttctc
1561 accagtggcg ttggtgcaga tgtggccagg atgtgggaga tagccatcca gcatgccctt
1621 atgcccgtca ttcccaaggg ctcctccgtg ggtacaggaa ccaacttgca cagagatatc
1681 tctgtgagta tttcagtatc aaattgccag attcaagaaa atgtggacat cagcacagta
1741 tatcagattt ttcctgatga agtactgggt tctggacagt ttggaattgt ttatggagga
1801 aaacatcgta aaacaggaag agatgtagct attaaaatca ttgacaaatt acgatttcca
1861 acaaaacaag aaagccagct tcgtaatgag gttgcaattc tacagaacct tcatcaccct
1921 ggtgttgtaa atttggagtg tatgttttgag acgcctaaa gagtgtttgt tgttatggaa
1981 aaactccatg gagacatgct ggaaatgatc ttgtcaagtg aaaagggcag gttgccagag
2041 cacataacga agttttttaat tactcagata ctcgtggctt tgcggcacct tcattttaaa
2101 aatatcgttc actgtgacct caaaccagaa aatgtgttgc tagcctcagc tgatccttt
2161 cctcaggtga aactttgtga tttttggtttt gcccggatca ttggagagaa gtctttccgg
2221 aggtcagtgg tgggtacccc cgcttacctg gctcctgagg tcctaaggaa caagggctac
2281 aatcgctctc tagacatgtg gtctgtttgg gtcatcatct atgtaagcct aagcgcaca
2341 ttcccattta atgaagatga agacatacac gaccaaaatc agaatgcagc tttcatgtat
2401 ccaccaaatc cctgaagga aatatctcat gaagccattg atcttatcca caatttgctg
2461 caagtaaaaa tgagaaagcg ctacagtgtg gataagacct tgagcaccc ttggctacag
2521 gactatcaga cctgttaga tttgcgagag ctgaatgca aatcggga gcgctacatc
2581 acccatgaaa gtgatgacct gaggtgggag aagtatgcag gcgagcaggg gctgcagtac
2641 cccacacacc tgatcaatcc aagtgctagc cacagtgaca ctcctgagac tgaagaaaca
2701 gaaatgaaag ccctcggtga gcgtgtcagc atcctctga  (SEQ ID NO:2)
```

FIG. 12B

SEQUENCE LISTING

<160> NUMBER OF SEQ ID NOS: 38

<210> SEQ ID NO 1
<211> LENGTH: 912
<212> TYPE: PRT
<213> ORGANISM: Homo sapiens

<400> SEQUENCE: 1

Met Ser Ala Pro Pro Val Leu Arg Pro Pro Ser Pro Leu Leu Pro Val
 1               5                  10                  15

Ala Ala Ala Ala Ala Ala Ala Ala Ala Ala Leu Val Pro Gly Ser Gly

```
                20                  25                  30
Pro Gly Pro Ala Pro Phe Leu Ala Pro Val Ala Pro Val Gly Gly
            35                  40                  45
Ile Ser Phe His Leu Gln Ile Gly Leu Ser Arg Glu Pro Val Leu Leu
    50                  55                  60
Leu Gln Asp Ser Ser Gly Asp Tyr Ser Leu Ala His Val Arg Glu Met
65                  70                  75                  80
Ala Cys Ser Ile Val Asp Gln Lys Phe Pro Glu Cys Gly Phe Tyr Gly
                85                  90                  95
Met Tyr Asp Lys Ile Leu Leu Phe Arg His Asp Pro Thr Ser Glu Asn
            100                 105                 110
Ile Leu Gln Leu Val Lys Ala Ala Ser Asp Ile Gln Glu Gly Asp Leu
        115                 120                 125
Ile Glu Val Val Leu Ser Ala Ser Ala Thr Phe Glu Asp Phe Gln Ile
        130                 135                 140
Arg Pro His Ala Leu Phe Val His Ser Tyr Arg Ala Pro Ala Phe Cys
145                 150                 155                 160
Asp His Cys Gly Glu Met Leu Trp Gly Leu Val Arg Gln Gly Leu Lys
                165                 170                 175
Cys Glu Gly Cys Gly Leu Asn Tyr His Lys Arg Cys Ala Phe Lys Ile
            180                 185                 190
Pro Asn Asn Cys Ser Gly Val Arg Arg Arg Leu Ser Asn Val Ser
            195                 200                 205
Leu Thr Gly Val Ser Thr Ile Arg Thr Ser Ser Ala Glu Leu Ser Thr
    210                 215                 220
Ser Ala Pro Asp Glu Pro Leu Leu Gln Lys Ser Pro Ser Glu Ser Phe
225                 230                 235                 240
Ile Gly Arg Glu Lys Arg Ser Asn Ser Gln Ser Tyr Ile Gly Arg Pro
                245                 250                 255
Ile His Leu Asp Lys Ile Leu Met Ser Lys Val Lys Val Pro His Thr
            260                 265                 270
Phe Val Ile His Ser Tyr Thr Arg Pro Thr Val Cys Gln Tyr Cys Lys
        275                 280                 285
Lys Leu Leu Lys Gly Leu Phe Arg Gln Gly Leu Gln Cys Lys Asp Cys
        290                 295                 300
Arg Phe Asn Cys His Lys Arg Cys Ala Pro Lys Val Pro Asn Asn Cys
305                 310                 315                 320
Leu Gly Glu Val Thr Ile Asn Gly Asp Leu Leu Ser Pro Gly Ala Glu
                325                 330                 335
Ser Asp Val Val Met Glu Glu Gly Ser Asp Asp Asn Asp Ser Glu Arg
            340                 345                 350
Asn Ser Gly Leu Met Asp Asp Met Glu Glu Ala Met Val Gln Asp Ala
        355                 360                 365
Glu Met Ala Met Ala Glu Cys Gln Asn Asp Ser Gly Glu Met Gln Asp
        370                 375                 380
Pro Asp Pro Asp His Glu Asp Ala Asn Arg Thr Ile Ser Pro Ser Thr
385                 390                 395                 400
Ser Asn Asn Ile Pro Leu Met Arg Val Val Gln Ser Val Lys His Thr
                405                 410                 415
Lys Arg Lys Ser Ser Thr Val Met Lys Glu Gly Trp Met Val His Tyr
            420                 425                 430
Thr Ser Lys Asp Thr Leu Arg Lys Arg His Tyr Trp Arg Leu Asp Ser
        435                 440                 445
```

-continued

```
Lys Cys Ile Thr Leu Phe Gln Asn Asp Thr Gly Ser Arg Tyr Tyr Lys
        450                 455                 460

Glu Ile Pro Leu Ser Glu Ile Leu Ser Leu Glu Pro Val Lys Thr Ser
465                 470                 475                 480

Ala Leu Ile Pro Asn Gly Ala Asn Pro His Cys Phe Glu Ile Thr Thr
                    485                 490                 495

Ala Asn Val Val Tyr Val Gly Glu Asn Val Val Asn Pro Ser Ser
                500                 505                 510

Pro Ser Pro Asn Asn Ser Val Leu Thr Ser Gly Val Gly Ala Asp Val
            515                 520                 525

Ala Arg Met Trp Glu Ile Ala Ile Gln His Ala Leu Met Pro Val Ile
530                 535                 540

Pro Lys Gly Ser Ser Val Gly Thr Gly Thr Asn Leu His Arg Asp Ile
545                 550                 555                 560

Ser Val Ser Ile Ser Val Ser Asn Cys Gln Ile Gln Glu Asn Val Asp
                565                 570                 575

Ile Ser Thr Val Tyr Gln Ile Phe Pro Asp Glu Val Leu Gly Ser Gly
                580                 585                 590

Gln Phe Gly Ile Val Tyr Gly Gly Lys His Arg Lys Thr Gly Arg Asp
            595                 600                 605

Val Ala Ile Lys Ile Ile Asp Lys Leu Arg Phe Pro Thr Lys Gln Glu
            610                 615                 620

Ser Gln Leu Arg Asn Glu Val Ala Ile Leu Gln Asn Leu His His Pro
625                 630                 635                 640

Gly Val Val Asn Leu Glu Cys Met Phe Glu Thr Pro Glu Arg Val Phe
                645                 650                 655

Val Val Met Glu Lys Leu His Gly Asp Met Leu Glu Met Ile Leu Ser
            660                 665                 670

Ser Glu Lys Gly Arg Leu Pro Glu His Ile Thr Lys Phe Leu Ile Thr
            675                 680                 685

Gln Ile Leu Val Ala Leu Arg His Leu His Phe Lys Asn Ile Val His
690                 695                 700

Cys Asp Leu Lys Pro Glu Asn Val Leu Leu Ala Ser Ala Asp Pro Phe
705                 710                 715                 720

Pro Gln Val Lys Leu Cys Asp Phe Gly Phe Ala Arg Ile Ile Gly Glu
                725                 730                 735

Lys Ser Phe Arg Arg Ser Val Val Gly Thr Pro Ala Tyr Leu Ala Pro
                740                 745                 750

Glu Val Leu Arg Asn Lys Gly Tyr Asn Arg Ser Leu Asp Met Trp Ser
            755                 760                 765

Val Gly Val Ile Ile Tyr Val Ser Leu Ser Gly Thr Phe Pro Phe Asn
770                 775                 780

Glu Asp Glu Asp Ile His Asp Gln Ile Gln Asn Ala Ala Phe Met Tyr
785                 790                 795                 800

Pro Pro Asn Pro Trp Lys Glu Ile Ser His Glu Ala Ile Asp Leu Ile
                805                 810                 815

Asn Asn Leu Leu Gln Val Lys Met Arg Lys Arg Tyr Ser Val Asp Lys
                820                 825                 830

Thr Leu Ser His Pro Trp Leu Gln Asp Tyr Gln Thr Trp Leu Asp Leu
            835                 840                 845

Arg Glu Leu Glu Cys Lys Ile Gly Glu Arg Tyr Ile Thr His Glu Ser
850                 855                 860
```

Asp Asp Leu Arg Trp Glu Lys Tyr Ala Gly Glu Gln Gly Leu Gln Tyr
865                 870                 875                 880

Pro Thr His Leu Ile Asn Pro Ser Ala Ser His Ser Asp Thr Pro Glu
            885                 890                 895

Thr Glu Glu Thr Glu Met Lys Ala Leu Gly Glu Arg Val Ser Ile Leu
        900                 905                 910

<210> SEQ ID NO 2
<211> LENGTH: 2739
<212> TYPE: DNA
<213> ORGANISM: Homo sapiens

<400> SEQUENCE: 2

| | |
|---|---|
| atgagcgccc ctccggtcct gcggccgccc agtccgctgc tgcccgtggc ggcggcagct | 60 |
| gccgcagcgg ccgccgcact ggtcccaggg tccgggcccg ggcccgcgcc gttcttggct | 120 |
| cctgtcgcgg ccccggtcgg gggcatctcg ttccatctgc agatcggcct gagccgtgag | 180 |
| ccggtgctgc tgctgcagga ctcgtccggg gactacagcc tggcgcacgt ccgcgagatg | 240 |
| gcttgctcca ttgtcgacca gaagttccct gaatgtggtt tctacggaat gtatgataag | 300 |
| atcctgcttt tcgccatga ccctacctct gaaaacatcc ttcagctggt gaaagcggcc | 360 |
| agtgatatcc aggaaggcga tcttattgaa gtggtcttgt cagcttccgc caccttgaa | 420 |
| gactttcaga ttcgtcccca cgctctcttt gttcattcat acagagctcc agctttctgt | 480 |
| gatcactgtg agaaatgct gtgggggctg gtacgtcaag gtcttaaatg tgaagggtgt | 540 |
| ggtctgaatt accataagag atgtgcattt aaaatacca acaattgcag cggtgtgagg | 600 |
| cggagaaggc tctcaaacgt ttccctcact ggggtcagca ccatccgcac atcatctgct | 660 |
| gaactctcta caagtgcccc tgatgagccc cttctgcaaa aatcaccatc agagtcgttt | 720 |
| attggtcgag agaagaggtc aaattctcaa tcatacattg acgaccaat tcaccttgac | 780 |
| aagattttga tgtctaaagt taaagtgccg cacacatttg tcatccactc ctacacccgg | 840 |
| cccacagtgt gccagtactg caagaagctt ctgaagggc ttttcaggca gggcttgcag | 900 |
| tgcaaagatt gcagattcaa ctgccataaa cgttgtgcac cgaaagtacc aaacaactgc | 960 |
| cttggcgaag tgaccattaa tggagatttg cttagccctg gggcagagtc tgatgtggtc | 1020 |
| atggaagaag ggagtgatga caatgatagt gaaaggaaca gtgggctcat ggatgatatg | 1080 |
| gaagaagcaa tggtccaaga tgcagagatg gcaatggcag agtgccagaa cgacagtggc | 1140 |
| gagatgcaag atccagaccc agaccacgag gacgccaaca gaaccatcag tccatcaaca | 1200 |
| agcaacaata tcccactcat gagggtagtg cagtctgtca acacacgaa gaggaaaagc | 1260 |
| agcacagtca tgaaagaagg atggatggtc cactacacca gcaaggacac gctgcggaaa | 1320 |
| cggcactatt ggagattgga tagcaaatgt attaccctct ttcagaatga cacaggaagc | 1380 |
| aggtactaca aggaaattcc tttatctgaa atttttgtctc tggaaccagt aaaaacttca | 1440 |
| gctttaattc ctaatgggc caatcctcat tgtttcgaaa tcactacggc aaatgtagtg | 1500 |
| tattatgtgg gagaaaatgt ggtcaatcct tccagcccat caccaaataa cagtgttctc | 1560 |
| accagtggcg ttggtgcaga tgtggccagg atgtgggaga tagccatcca gcatgccctt | 1620 |
| atgcccgtca ttcccaaggg ctcctccgtg gtacaggaa ccaacttgca cagagatatc | 1680 |
| tctgtgagta tttcagtatc aaattgccag attcaagaaa atgtggacat cagcacagta | 1740 |
| tatcagattt ttcctgatga agtactgggt tctggacagt ttggaattgt ttatggagga | 1800 |
| aaacatcgta aaacaggaag agatgtagct attaaaatca ttgacaaatt acgatttcca | 1860 |

```
acaaaacaag aaagccagct tcgtaatgag gttgcaattc tacagaacct tcatcaccct   1920
ggtgttgtaa atttggagtg tatgtttgag acgcctgaaa gagtgtttgt tgttatggaa   1980
aaactccatg gagacatgct ggaaatgatc ttgtcaagtg aaaagggcag gttgccagag   2040
cacataacga agttttaat tactcagata ctcgtggctt tgcggcacct tcattttaaa    2100
aatatcgttc actgtgacct caaccagaa aatgtgttgc tagcctcagc tgatcctttt    2160
cctcaggtga aactttgtga ttttggtttt gcccggatca ttggagagaa gtctttccgg   2220
aggtcagtgg tgggtacccc cgcttacctg gctcctgagg tcctaaggaa caagggctac   2280
aatcgctctc tagacatgtg gtctgttggg gtcatcatct atgtaagcct aagcggcaca   2340
ttcccattta atgaagatga agacatacac gaccaaattc agaatgcagc tttcatgtat   2400
ccaccaaatc cctggaagga aatatctcat gaagccattg atcttatcaa caatttgctg   2460
caagtaaaaa tgagaaagcg ctacagtgtg ataagacct gagccaccc ttggctacag     2520 gactatcaga cctggttaga tttgcgagag ctggaatgca aaatcgggga gcgctacatc   2580
acccatgaaa gtgatgacct gaggtgggag aagtatgcag cgagcaggg gctgcagtac    2640 cccacacacc tgatcaatcc aagtgctagc cacagtgaca ctcctgagac tgaagaaaca   2700
gaaatgaaag ccctcggtga gcgtgtcagc atcctctga                          2739
```

<210> SEQ ID NO 3
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 3

```
Ser Asn Val Ser Leu Thr Gly Leu Gly Thr Val Arg Thr Ala Ser Ala
  1               5                  10                  15

Glu Phe Ser Thr Ser Val Pro Asp Glu Pro Leu Leu Ser Pro Val Ser
                 20                  25                  30

Pro Gly Phe Glu Gln Lys Ser Pro Ser Glu Ser Phe Ile Gly Arg Glu
             35                  40                  45

Lys Arg Ser Asn Ser Gln Ser Tyr Ile Gly Arg
         50                  55
```

<210> SEQ ID NO 4
<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 4

```
Asn Gly Glu Leu Leu Ser Pro Gly Ala Glu Ser Asp Val Val Met Glu
  1               5                  10                  15

Glu Gly Ser Asp Asp Asn Asp Ser Glu Arg Asn Ser Gly Leu Met Asp
                 20                  25                  30

Asp Met Asp Glu Ala Met Val Gln Asp Thr Glu Met Ala Leu Ala Glu
             35                  40                  45

Gly Gln Ser Gly Gly Ala Glu Met Gln Asp Pro Asp Ala Asp Gln Glu
         50                  55                  60

Asp Ser Asn Arg Thr Ile Ser Pro Ser Thr Ser Asn Asn Ile
 65                  70                  75
```

<210> SEQ ID NO 5

```
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 5

Trp Glu Gln Tyr Ala Gly Glu Gln Gly Leu Gln Tyr Pro Ala His Leu
 1               5                  10                  15

Ile Ser Leu Ser Ala Ser His Ser Asp Ser Pro Glu Ala Glu Arg
            20                  25                  30

Glu Met Lys Ala Leu Ser Glu Arg Val Ser Ile Leu
        35                  40

<210> SEQ ID NO 6
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 6

Cys Tyr Pro Tyr Asp Val Pro Asp Tyr Ala
 1               5                  10

<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Asp Tyr Lys Asp Asp Asp Asp Lys
 1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 8

Cys Glu Gln Lys Leu Ile Ser Glu Glu Asp Leu
 1               5                  10

<210> SEQ ID NO 9
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 9

His His His His His
 1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 10
```

His His His His His His
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 11

Glu Gln Lys Leu Ile Ser Glu Glu Asp Leu
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 12

Trp Ser His Pro Gln Phe Glu Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 13

Tyr Pro Tyr Asp Val Pro Asp Tyr Ala
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 14

Arg Tyr Ile Arg Ser
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 15

Phe His His Thr
1

<210> SEQ ID NO 16
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 16

Trp Glu Ala Ala Ala Arg Glu Ala Cys Cys Arg Glu Cys Cys Ala Arg

```
<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
aaagagtgtt tgttgttatg g                                              21

<210> SEQ ID NO 18
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 18
acgcctgaaa gagtgtttgt tgttatggaa                                     30

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
acgcctgaaa gagtgtttgt                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gagtgtttgt tgttatggaa                                                20

<210> SEQ ID NO 21
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 21
gagtgtttgt tgttatggaa aaactccatg                                     30

<210> SEQ ID NO 22
<211> LENGTH: 80
<212> TYPE: PRT
<213> ORGANISM: Artificial Sequence
<220> FEATURE:
<223> OTHER INFORMATION: Synthetic polypeptide

<400> SEQUENCE: 22
```

(previous sequence continued)

```
                                    1               5                  10                  15
Ala
```

```
Met Ala Ala Ala Pro Ser His Pro Ala Gly Leu Pro Gly Ser Pro Gly
 1               5                  10                  15

Pro Gly Ser Pro Pro Pro Gly Gly Leu Asp Leu Gln Ser Pro Pro
            20                  25                  30
```

```
Pro Leu Leu Pro Gln Ile Pro Ala Pro Gly Ser Gly Val Ser Phe His
         35                  40                  45

Ile Gln Ile Gly Leu Thr Arg Glu Phe Val Leu Pro Ala Ala Ser
 50                  55                  60

Glu Leu Ala His Val Lys Gln Leu Ala Cys Ser Ile Val Asp Gln Lys
 65                  70                  75                  80

<210> SEQ ID NO 23
<211> LENGTH: 80
<212> TYPE: PRT
<213> ORGANISM: Artificial Sequence
<220> FEATURE:
<223> OTHER INFORMATION: Synthetic polypeptide

<400> SEQUENCE: 23

Met Ser Ala Asn Asn Ser Pro Pro Ser Ala Gln Lys Ser Val Phe Pro
 1               5                  10                  15

Ala Thr Val Ser Ala Val Leu Pro Ala Pro Ser Pro Cys Ser Ser Pro
             20                  25                  30

Lys Thr Gly Leu Ser Ala Arg Leu Ser Asn Gly Ser Phe Ser Ala Pro
         35                  40                  45

Ser Leu Thr Asn Ser Arg Gly Ser Val His Thr Val Ser Phe Leu Leu
 50                  55                  60

Gln Ile Gly Leu Thr Arg Glu Ser Val Thr Ile Glu Ala Gln Glu Leu
 65                  70                  75                  80

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
aaagtgtgat tgttgtttag g                                             21

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
cctgagccac ctggaagagt a                                             21

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
ggcccattca tgtggttctg                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 27
ctgtgacctc aagccagaaa                                                  20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gtacccacca ctgacctcct                                                  20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
catcgacctc atcaacaacc                                                  20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
tggctgagag acttgtccac                                                  20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
cccagaaatc tgtgttccct                                                  20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
agagagccga gctgagagtc                                                  20

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 33
ccccaatgtg tccgtcgt                                                    18

<210> SEQ ID NO 34
<211> LENGTH: 19

```
<212> TYPE: DNA
<213> ORGANISM: Artificial Sequence
<220> FEATURE:
<223> OTHER INFORMATION: Synthetic oligonucleotide

<400> SEQUENCE: 34
gcctgcttca ccaccttct                                                  19

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 35
ccctgcaccg tgtatcttag agtg                                            24

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
tccacccttg caactaattt g                                               21

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
taacctggtg tccctcctgg atc                                             23

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
gcaaagactt ctcagcagcc ttga                                            24
```

COMPOSITIONS AND METHODS FOR TREATING NEUROLOGICAL DISORDERS

CROSS-REFERENCE

This application is a continuation-in-part application of International Patent Application No. PCT/US2011/029806, having an international filing date of Mar. 24, 2011, which application is incorporated herein by reference in its entirety. This application claims the benefit of U.S. Provisional Patent Application No. 61/317,598, filed Mar. 25, 2010, which application is incorporated herein by reference in its entirety.

STATEMENT REGARDING FEDERALLY SPONSORED RESEARCH

This invention was made with government support under Grant Nos. RO1 NS039074 and PO1 AG022074 awarded by the National Institutes of Health. The government has certain rights in the invention.

BACKGROUND

AMPA-type glutamate receptors (AMPARs) mediate the majority of fast, excitatory neurotransmission in the central nervous system, and the number and subunit composition of AMPARs are major determinants of synaptic strength. AMPARs are heterotetramers made up of the subunits GluR1-4. GluR2 is particularly important for determining the properties of the receptor: receptors that lack GluR2 pass $Ca^{2+}$ and have different kinetics and single-channel conductances than those with GluR2. Thus, the relative amount of GluR2 at the post-synaptic density (PSD) has a major effect on synaptic efficacy. Indeed, the ratio of GluR2-containing to GluR2-lacking AMPARs at the PSD may be regulated in both mGluR- and NMDAR-dependent forms of plasticity.

In non-neuronal cells, extracellular signals regulate endosomal trafficking through protein kinase D1 (PKD1). PKD1 facilitates the recycling of β3 integrins to focal adhesions in epithelia during wound-healing and mediates $Ca^{2+}$-dependent insulin secretion in pancreatic β cells.

SUMMARY OF THE INVENTION

The present disclosure provides methods for treating neurological disorders, generally involving modulating protein kinase D1 (PKD1) activity levels in a neuron or glial cell in an individual in need thereof. The present disclosure provides antibodies specific for PKD1. The present disclosure provides genetically modified non-human animals deficient in PKD1 activity.

BRIEF DESCRIPTION OF THE DRAWINGS

FIGS. 2A-C depict the effect of metabotropic glutamate receptor (mGluR) activation on PKD1 kinase activity.

FIGS. 4A-C depict the role of phospholipase C (PLC) on PKD1 translocation.

FIG. 11 depicts an amino acid sequence of a human PKD1 polypeptide.

FIGS. 12A and B depict a nucleotide sequence encoding a human PKD1 polypeptide.

DEFINITIONS

Figure 1:
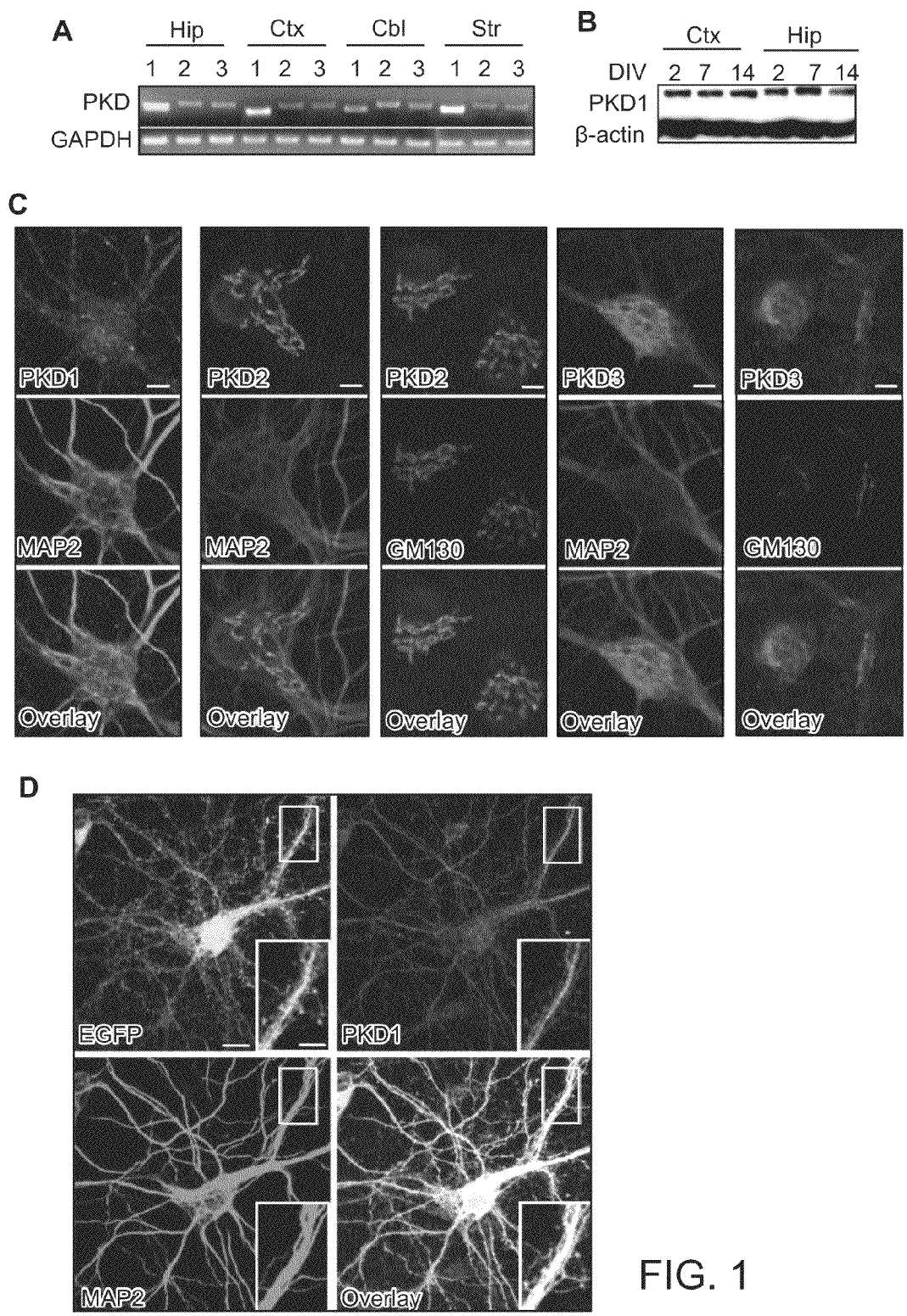
FIGS. 1A-D depict expression of PKD1 in mouse brain and neurons.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "short interfering nucleic acid," "siNA," "short interfering RNA," "siRNA," "short interfering nucleic acid molecule," "short interfering oligonucleotide molecule," or "chemically-modified short interfering nucleic acid molecule," as used herein, refer to any nucleic acid molecule capable of inhibiting or down regulating gene expression, for example by mediating RNA interference "RNAi" or gene silencing in a sequence-specific manner. Design of RNAi molecules when given a target gene is routine in the art. See also US 2005/0282188 (which is incorporated herein by reference) as well as references cited therein. See, e.g., Pushparaj et al. Clin Exp Pharmacol Physiol. 2006 May-June; 33(5-6):504-10; Lutzelberger et al. Handb Exp Pharmacol. 2006; (173):243-59; Aronin et al. Gene Ther. 2006 March; 13(6):509-16; Xie et al. Drug Discov Today. 2006 January; 11(1-2):67-73; Grunweller et al. Curr Med. Chem. 2005; 12(26):3143-61; and Pekaraik et al. Brain Res Bull. 2005 Dec. 15; 68(1-2):115-20. Epub 2005 Sep. 9.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules (e.g., single chain Fv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

The following terms are used to describe the sequence relationships between two or more polynucleotides, or polypeptides: (a) "reference sequence," (b) "comparison window," (c) "sequence identity," and (d) "percent sequence identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a sequence, wherein the sequence in the comparison window may include additions or deletions (i.e., gaps) compared to the reference sequence (which does not include additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller, CABIOS, 4:11 (1988); the local homology algorithm of Smith et al., Adv. Appl. Math., 2:482 (1981); the homology alignment algorithm of Needleman and Wunsch, JMB, 48:443 (1970); the search-for-similarity-method of Pearson and Lipman, Proc. Natl. Acad. Sci. USA, 85:2444 (1988); the algorithm of Karlin and Altschul, Proc. Natl. Acad. Sci. USA, 87:2264 (1990), modified as in Karlin and Altschul, Proc. Natl. Acad. Sci. USA, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988); Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994). The ALIGN program is based on the algorithm of Myers and Miller, supra. The BLAST programs of Altschul et al., JMB, 215:403 (1990); Nucl. Acids Res., 25:3389 (1990), are based on the algorithm of Karlin and Altschul supra.

(c) As used herein, "sequence identity" or "identity" in the context of two nucleotide or amino acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percent sequence identity" means the value determined by comparing two optimally aligned sequences over a comparison window, wherein the portion of the nucleotide or amino acid sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

Before aspects of the present disclosure are further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a protein kinase D1 polypeptide" includes a plurality of such polypeptides and reference to "the PKD1 modulator" includes reference to one or more PKD1 modulators and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods for treating neurological disorders, generally involving modulating protein kinase D1 (PKD1) activity levels in a neuron and/or glial cell in an individual in need thereof. The present disclosure provides antibodies specific for PKD1. The present disclosure provides genetically modified non-human animals deficient in PKD1 activity.

Methods of Treating Neurological Disorders

The present disclosure provides methods for treating neurological disorders, generally involving modulating (e.g., reducing) PKD1 activity levels in a neuron and/or a glial cell in an individual in need of such treatment.

In some embodiments, an effective amount of an agent that modulates PKD1 activity levels in an individual (e.g., in a neuron and/or glial cell in the individual) is an amount that, when administered in monotherapy or in combination therapy, in one or more doses, is effective to treat a neurological disorder in an individual. In some embodiments, an effective amount of an agent that modulates PKD1 activity levels in an individual (e.g., in a neuron and/or glial cell in the individual) is an amount that, when administered to an individual in monotherapy or in combination therapy, in one or more doses, is effective to reduce an adverse symptom of a neurological disorder in the individual. In some embodiments, an effective amount of an agent that modulates PKD1 activity levels in an individual (e.g., in a neuron and/or glial cell in the individual) is an amount that, when administered to an individual in monotherapy or in combination therapy, in one or more doses, is effective to result in an improvement in at least one neurological function in the individual. Glial cells include microglia, oligodendrocytes, and astrocytes. In particular embodiments, the agent inhibits PKD1 activity or reduces PKD1 levels, thereby reducing PKD1 activity.

As used herein, a "protein kinase D1 polypeptide" or a "PKD1 polypeptide" refers to a polypeptide comprising an amino acid sequence having at least about 80%, at least about 85%, at least about 90%, at least about 95%, at least about 98%, at least about 99%, or 100%, amino acid sequence identity to a contiguous stretch of from about 750 amino acids (aa) to about 800 aa, from about 800 aa to about 850 aa, from about 850 aa to about 900 aa, or from about 900 aa to 912 aa, of the amino acid sequence depicted in FIG. 11 and set forth in SEQ ID NO:1. A PKD1 polypeptide includes naturally-occurring allelic variants of the amino acid sequence depicted in FIG. 11 and set forth in SEQ ID NO:1. A PKD1 polypeptide includes enzymatically active variants that have the above noted amino acid sequence identity to the amino acid sequence depicted in FIG. 11 and set forth in SEQ ID NO:1.

Amino acid sequences of PKD1 polypeptides are known in the art, and are disclosed in, e.g., GenBank Accession No. NP_002733 (*Homo sapiens*); GenBank Accession No. XP_001170806.1 (*Pan troglodytes*); GenBank Accession No. XP_001114639.1 (*Macaca mulatta*); GenBank Accession No. XP_612625.4 (*Bos taurus*); GenBank Accession No. XP_851386.1 (*Canis familiaris*); GenBank Accession No. XP_001489407.2 (*Equus caballus*); GenBank Accession No. XP_234108.4 (*Rattus norvegicus*); GenBank Accession No. NP_032884.2 (*Mus musculus*); and GenBank Accession No. NP_001026372.1 (*Gallus gallus*).

A PKD1 polypeptide can be encoded by a nucleotide sequence having at least about 80%, at least about 85%, at least about 90%, at least about 95%, at least about 98%, at least about 99%, or 100%, amino acid sequence identity to a contiguous stretch from about 2250 nucleotides (nt) to about 2300 nt, from about 2300 nt to about 2400 nt, from about 2400 nt to about 2500 nt, from about 2500 nt to about 2600 nt, from about 2600 nt to about 2700 nt, or from about 2700 nt to 2739 nt, of the nucleotide sequence depicted in FIGS. 12A and 12B and set forth in SEQ ID NO:2.

Nucleotide sequences encoding PKD1 polypeptides are known in the art, and are disclosed in, e.g., GenBank Accession No. NM_002742 (*Homo sapiens*); GenBank Accession No. XM_001170806.1 (*Pan troglodytes*); GenBank Accession No. XM_001114639.1 (*Macaca mulatta*); GenBank Accession No. XM_612625.4 (*Bos taurus*); GenBank Accession No. XM_846293.1 (*Canis familiaris*); GenBank Accession No. XM_0011489357.2 (*Equus caballus*); GenBank Accession No. XM_001078506.1 (*Rattus norvegicus*); GenBank Accession No. NM_008858.3 (*Mus musculus*).

Disorders that are treatable using a subject method include, but are not limited to, epilepsy, ischemia, cerebellar ataxia; neurodegenerative diseases such as Huntington's disease, Parkinson's disease, amyotrophic lateral sclerosis, and Alzheimer's disease; demyelinating diseases, including disseminated perivenous encephalomyelitis, multiple sclerosis, neuromyelitis optica, concentric sclerosis, acute, disseminated encephalomyelitides, post encephalomyelitis, postvaccinal encephalomyelitis, acute hemorrhagic leukoencephalopathy, progressive multifocal leukoencephalopathy, idiopathic polyneuritis, diphtheric neuropathy, Pelizaeus-Merzbacher disease, neuromyelitis optica, diffuse cerebral sclerosis, central pontine myelinosis, spongiform leukodystrophy, and leukodystrophy (Alexander type); and acute brain injury (e.g. stroke, head injury, cerebral palsy).

Active Agents

A subject treatment method involves administering to an individual in need thereof an effective amount of an active agent that modulates PKD1 activity in a neuron and/or in a glial cell in the individual. Suitable active agents include small molecules, antibodies specific for PKD1, and nucleic acid agents that modulate PKD1 levels in a neuron and/or a glial cell.

In some embodiments, a suitable agent is an agent that increases PKD1 activity by at least about 10%, at least about 15%, at least about 20%, at least about 25%, at least about 50%, at least about 75%, at least about 100% or 2-fold, at least about 2.5-fold, at least about 5-fold, at least about 10-fold, at least about 20-fold, or more than 20-fold, compared to the activity of PKD1 in the absence of the agent. In some embodiments, a suitable agent is one that increases the level of active PKD1 in a neuron or glial cell by at least about 10%, at least about 15%, at least about 20%, at least about 25%, at least about 50%, at least about 75%, at least about 100% or 2-fold, at least about 2.5-fold, at least about 5-fold, at least about 10-fold, at least about 20-fold, or more than 20-fold, compared to the level of active PKD1 in the neuron or glial cell in the absence of the agent.

In some embodiments, a suitable agent is an agent that inhibits PKD1 activity in a neuron or a glial cell by at least about 10%, at least about 15%, at least about 20%, at least about 25%, at least about 50%, at least about 75%, or at least about 80%, compared to the activity of the PKD1 polypeptide in the absence of the agent. In some embodiments, a suitable agent is one that decreases the level of active PKD1 in a neuron or glial cell by at least about 10%, at least about 15%, at least about 20%, at least about 25%, at least about 50%, at least about 75%, or at least about 80%, compared to the level of active PKD1 in the neuron or glial cell in the absence of the agent.

In some embodiments, a suitable agent is an agent that inhibits PKD1 activity with a half-maximal inhibitory concentration ($IC_{50}$) of from about 1 nM to about 5 nM, from about 5 nM to about 10 nM, from about 10 nM to about 25 nM, from about 25 nM to about 50 nM, from about 50 nM to about 75 nM, from about 75 nM to about 100 nM, from about 100 nM to about 250 nM, from about 250 nM to about 500 nM, from about 500 nM to about 1 µM, or from about 1 µM to about 10 µM. For example, in some embodiments, a suitable PKD1 inhibitor includes a compound that inhibits human PKD1 with an $IC_{50}$ of from about 1 nM to about 5 nM, from about 5 nM to about 10 nM, from about 10 nM to about 25 nM, from about 25 nM to about 50 nM, from about 50 nM to about 75 nM, from about 75 nM to about 100 nM, from about 100 nM to about 250 nM, from about 250 nM to about 500 nM, from about 500 nM to about 1 µM, or from about 1 µM to about 10 µM.

Small Molecule Agents

Suitable active agents include small molecule agents that modulate PKD1 kinase activity. Suitable small molecule agents include, but are not limited to, amino-ethyl-amino-aryl (AEAA) (see, e.g., U.S. Patent Publication No. 2009/0247519); an imidazopyrazine compound (see, e.g., U.S. Patent Publication No. 2009/0175852); an indazole compound (see, e.g., U.S. Patent Publication No. 2006/0004043);

In some embodiments, a small molecule PKD1 modulator is an amino-ethyl-amino-aryl (AEAA) compound of the formula:

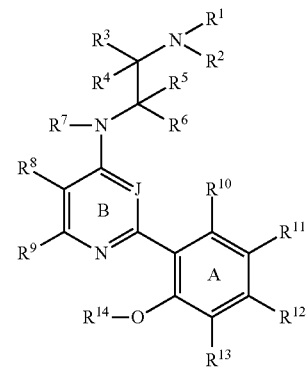

where J is independently N or CH; and wherein:

(1) each of $R^8$ and $R^9$ is independently —H or a Ring B substituent; or (2) $R^8$ and $R^9$, taken together with the atoms to which they are attached, form an aromatic Ring C having exactly 5 ring atoms or exactly 6 ring atoms, wherein each ring atom is a carbon ring atom or a nitrogen ring atom, wherein Ring C has exactly 0, exactly 1, or exactly 2 ring nitrogen atoms, and wherein Ring C is fused to Ring B; and wherein:

(1) each of $R^{10}$, $R^{11}$, $R^{12}$, and $R^{13}$ is independently —H or a Ring A substituent; or (2) each of $R^{12}$ and $R^{13}$ is independently a —H or Ring A substituent; and $R^{10}$ and $R^{11}$, taken together with the atoms to which they are attached, form an aromatic Ring D having exactly 6 atoms, wherein each ring atom is a carbon ring atom, and wherein Ring D is fused to Ring A; or (3) each of $R^{10}$ and $R^{13}$ is independently —H or a Ring A substituent; and $R^{11}$ and $R^{12}$, taken together with the atoms to which they are attached, form an aromatic Ring E having exactly 6 ring atoms, wherein each ring atom is a carbon ring atom, and wherein Ring E is fused to Ring A; or (4) each of $R^{10}$ and $R^{11}$ is independently —H or a Ring A substituent; and $R^{12}$ and $R^{13}$, taken together with the atoms to which they are attached, form an aromatic Ring F having exactly 6 ring atoms, wherein each ring atom is a carbon ring atom, and wherein Ring F is fused to Ring A; and wherein:

each of $R^1$, $R^2$, $R^3$, $R^4$, $R^5$, $R^6$, and $R^7$ is independently —H or a group G;

and additionally wherein:

each of $R^3$, $R^4$, $R^5$, and $R^6$ may be a group Y;

each of $R^1$, $R^2$, and $R^7$ may be a group Z;

$R^3$ and $R^4$, taken together, may form a group =O;

$R^5$ and $R^6$, taken together, may form a group =O;

and wherein:

$R^{14}$ is independently —H or a group W.

Suitable compounds are found among compounds XX001 to XX344, and compounds YY-001, YY-002, and YY-003, of U.S. Patent Publication No. 2009/0247519. For example, suitable compounds include, e.g.:

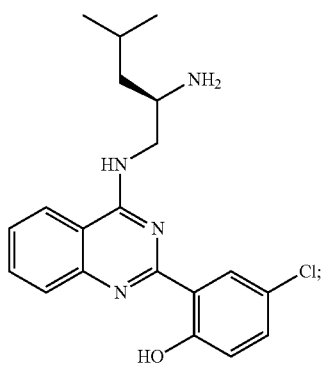
(XX-026)

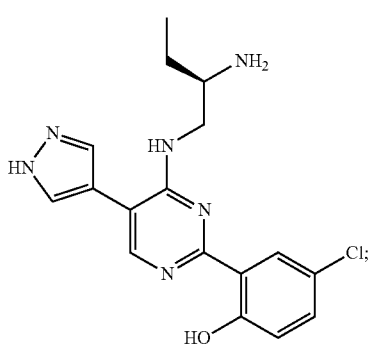
(XX-168)

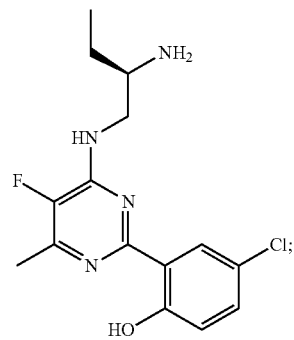
(XX-183)

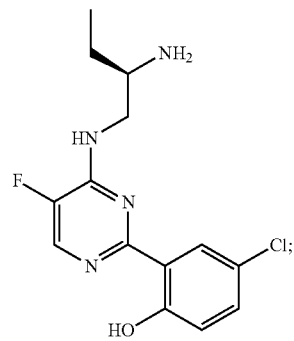
(XX-184)

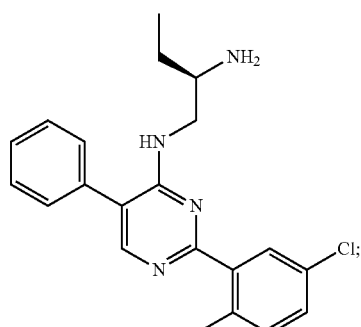
(XX-190)

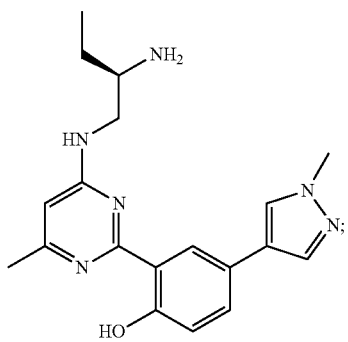
(XX-201)

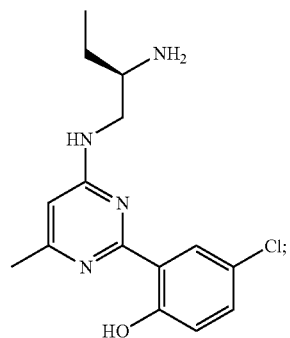
(XX-202)
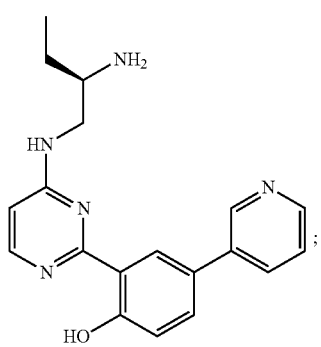
(XX-227)
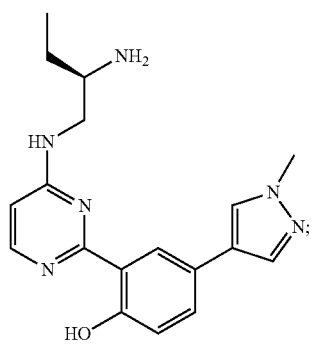
(XX-207)
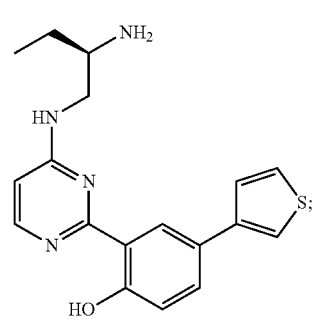
(XX-230)
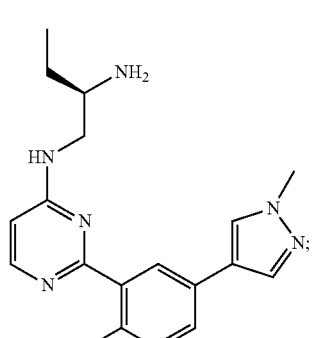
(XX-209)
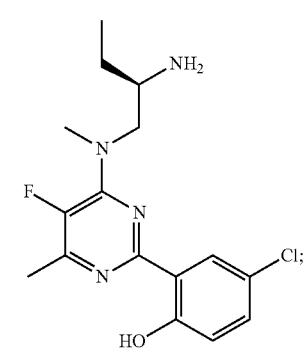
(XX-265)
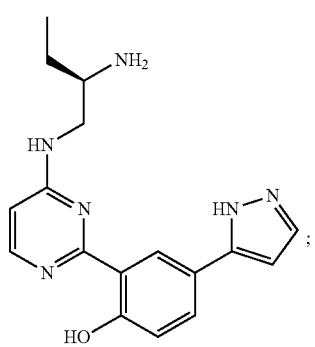
(XX-210)
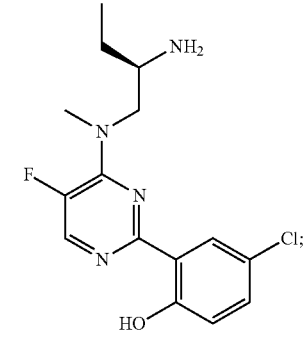
(XX-266)

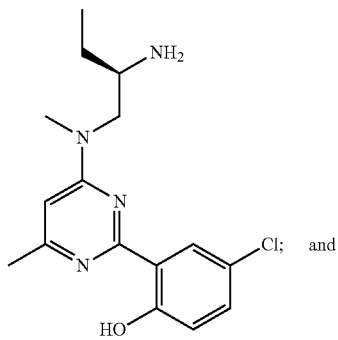
(XX-267)

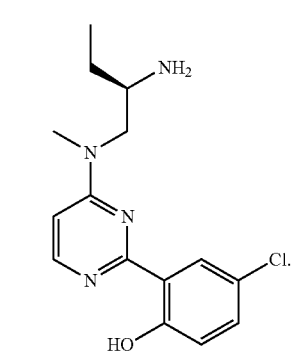
(XX-276)

Antibody Agents

Suitable active agents include antibodies that specifically bind PKD1. In some embodiments, an antibody that specifically binds PKD1 is a monoclonal antibody. In some embodiments, an antibody that specifically binds PKD1 is a polyclonal antibody. In some embodiments, an antibody that specifically binds PKD1 is an antibody fragment, e.g., a single chain Fv (scFv) antibody. In some embodiments, an antibody that specifically binds PKD1 comprises one or more modifications.

The present disclosure provides antibodies specific for PKD1. A subject antibody can be used in a subject treatment method. A subject antibody can also be used in detection methods, e.g., diagnostic and disease monitoring methods. The present disclosure further provides compositions, including pharmaceutical compositions, comprising a subject antibody.

In some embodiments, an antibody specifically recognizes and binds to a PKD1 epitope(s) contained within PKD1 amino acids 203-261, amino acids 333-410, or amino acids 875-918.

PKD1 amino acids 203-261 include, e.g.:

```
                                            (SEQ ID NO: 3)
SNVSLTGLGTVRTASAEFSTSVPDEPLLSPVSPGFEQKSPSESFIGREKR

SNSQSYIGR;
```

PKD1 amino acids 333-410 include, e.g.:

```
                                            (SEQ ID NO: 4)
NGELLSPGAESDVVMEEGSDDNDSERNSGLMDDMDEAMVQDTEMALAEGQ

SGGAEMQDPDADQEDSNRTISPSTSNNI;
```

PKD1 amino acids 875 to 918 include, e.g.:

```
                                            (SEQ ID NO: 5)
WEQYAGEQGLQYPAHLISLSASHSDSPEAEEREMKALSERVSIL.
```

In some embodiments, a PKD1 epitope can be formed by a polypeptide having at least about 75%, at least about 80%, at least about 85%, at least about 90%, at least about 95%, at least about 98%, at least about 99%, or 100%, amino acid sequence identity to a contiguous stretch of 3 amino acids (aa), 4 aa, 5 aa, 6 aa, 7 aa, 8 aa, 9 aa, 10 aa, 11 aa, 12 aa, 13 aa, 14 aa, or 15 aa, of one of the sequences:

```
                                            (SEQ ID NO: 3)
SNVSLTGLGTVRTASAEFSTSVPDEPLLSPVSPGFEQKSPSESFIGREKR

SNSQSYIGR, (SEQ ID NO: 4)
NGELLSPGAESDVVMEEGSDDNDSERNSGLMDDMDEAMVQDTEMALAEGQ

SGGAEMQDPDADQEDSNRTISPSTSNNI,
and (SEQ ID NO: 5)
WEQYAGEQGLQYPAHLISLSASHSDSPEAEEREMKALSERVSIL.
```

A subject antibody exhibits high affinity binding to a PKD1 polypeptide. For example, a subject antibody binds to PKD1 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject antibody binds to an epitope present on PKD1 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

A subject antibody exhibits substantially no binding to any epitopes formed by amino acids within a PKD2 polypeptide. Any binding of a subject antibody to an epitope formed by amino acids within a PKD2 polypeptide is generally non-specific binding of a substantially lower affinity than the specific binding of the antibody to an epitope on PKD1. A substantially lower affinity is generally at least a two fold, three fold, five fold, 10 fold, 50 fold, 100 fold, 500 fold, or 1000 fold lower affinity.

The term "antibody" refers to a protein comprising one or more (e.g., one or two) heavy chain variable regions (VH) and/or one or more (e.g., one or two) light chain variable regions (VL), or subfragments thereof capable of binding an epitope. The VH and VL regions can be further subdivided into regions of hypervariability, termed "complementarity determining regions (CDR)", interspersed with regions that are more conserved, termed "framework regions (FR)". The extent of the FR and CDRs has been precisely defined (see, Kabat, et al. (1991) Sequences of Proteins of Immunological Interest, Fifth Edition, U.S. Department of Health and Human Services, NIH Publication No. 91-3242; Chothia et al. (1987) J. Mol. Biol. 196: 901-917). A VH can comprise three CDRs and four FRs arranged from N-terminus to C-terminus in the following order: FR1, CDR1, FR2, CDR2, FR3, CDR3, FR4. Similarly, a VL can comprise three CDRs and four FRs arranged from N-terminus to C-terminus in the following order: FR1, CDR1, FR2, CDR2, FR3, CDR3, FR4.

The VH or VL chain of an antibody can further include all or part of a heavy or light chain constant region, to thereby form a heavy or light immunoglobulin chain, respectively. In one embodiment, the antibody is a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes intact immunoglobulins of types IgA, IgG, IgE, IgD, IgM and subtypes thereof. In some embodiments, a subject antibody is an IgG isotype.

As used herein the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

In some embodiments, a subject antibody does not comprise a full-length immunoglobulin heavy chain and a full-length immunoglobulin light chain, and instead comprises antigen-binding fragments of a full-length immunoglobulin heavy chain and a full-length immunoglobulin light chain. In some embodiments, the antigen-binding fragments are contained on separate polypeptide chains; in other embodiments, the antigen-binding fragments are contained within a single polypeptide chain. The term "antigen-binding fragment" refers to one or more fragments of a full-length antibody that are capable of specifically binding to a PKD1 polypeptide as described above. Examples of binding fragments include (i) a Fab fragment (a monovalent fragment consisting of the VL, VH, CL and CH1 domains; (ii) a F(ab')$_2$ fragment (a bivalent fragment comprising two Fab fragments linked by a disulfide bridge at the hinge region; (iii) a Fd fragment (consisting of the VH and CH1 domains); (iv) a Fv fragment (consisting of the VH and VL domains of a single arm of an antibody); (v) a dAb fragment (consisting of the VH domain); (vi) an isolated CDR; (vii) a single chain Fv (scFv) (consisting of the VH and VL domains of a single arm of an antibody joined by a synthetic linker using recombinant means such that the VH and VL domains pair to form a monovalent molecule); (viii) diabodies (consisting of two scFvs in which the VH and VL domains are joined such that they do not pair to form a monovalent molecule; the VH of each one of the scFv pairs with the VL domain of the other scFv to form a bivalent molecule); (ix) bi-specific antibodies (consisting of at least two antigen binding regions, each region binding a different epitope). In some embodiments, a subject antibody fragment is a Fab fragment. In some embodiments, a subject antibody fragment is a single-chain antibody (scFv).

In some embodiments, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and may be found in, e.g., U.S. Pat. No. 5,849,860. PEG suitable for conjugation to a protein is generally soluble in water at room temperature, and has the general formula R(O—$CH_2$—$CH_2$)$_n$O—R, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., comprise a covalently linked carbohydrate or polysaccharide moiety. Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one step reaction procedure in which the cross-linker is added to a solution containing a mixture of the polypeptides to be linked Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2, 4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, 125I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-dephenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2): 209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020, 192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from *Anthozoan* species, as described in, e.g., Matz et al. (1999) *Nature Biotechnol.* 17:969-973; and the like.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., CYPYDVPDYA; SEQ ID NO:6), FLAG (e.g., DYKDDDDK; SEQ ID NO:7), c-myc (e.g., CEQKLISEEDL; SEQ ID NO:8), and the like; provide a detectable signal, e.g., an enzyme that generates a detectable product (e.g., (β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:9), HisX6 (HHHHHH) (SEQ ID NO:10), C-myc (EQKLISEEDL) (SEQ ID NO:11), Flag (DYKDDDDK) (SEQ ID NO:7), StrepTag (WSHPQFEK) (SEQ ID NO:12), hemagglutinin, e.g., HA Tag (YPYDVPDYA; SEQ ID NO:13), glutathinone-5-transferase (GST), thioredoxin, cellulose binding domain, RYIRS (SEQ ID NO:14), Phe-His-His-Thr (SEQ ID NO:15), chitin binding domain, S-peptide, T7 peptide, SH2 domain, C-end RNA tag, WEAAAREACCRECCARA (SEQ ID NO:16), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

A subject antibody will in some embodiments be fused to a polypeptide that binds to an endogenous blood brain barrier (BBB) receptor. Linking a subject antibody to a polypeptide that binds to an endogenous BBB receptor facilitates crossing the BBB, e.g., in a subject treatment method (see below) involving administration of a subject antibody to an individual in need thereof. Suitable polypeptides that bind to an endogenous BBB include antibodies, e.g., monoclonal antibodies, or antigen-binding fragments thereof, that specifically bind to an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

In some embodiments, a subject antibody comprises a polyamine modification. Polyamine modification of a subject antibody enhances permeability of the modified antibody at the BBB. A subject antibody can be modified with polyamines that are either naturally occurring or synthetic. See, for example, U.S. Pat. No. 5,670,477. Useful naturally occurring polyamines include putrescine, spermidine, spermine, 1,3-deaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or $N(R)_2$ moieties, wherein R is H, ($C_1$-$C_4$) alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated into a liposome.

A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

The present disclosure provides a composition comprising a subject antibody. A subject antibody composition can comprise, in addition to a subject antibody, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

The present disclosure further provides pharmaceutical compositions comprising a subject antibody. Thus, the present disclosure provides a pharmaceutical composition comprising a subject antibody and a pharmaceutically acceptable excipient. Pharmaceutically acceptable excipients are described below.

Nucleic Acid Agents

Suitable active agents include nucleic acid agents that specifically reduce PKD1 levels in a neuron and/or a glial cell. The present disclosure further provides isolated interfering nucleic acids that specifically reduce PKD1 levels in a cell, e.g., in a neuron and/or a glial cell.

Interfering nucleic acids include small nucleic acid molecules, such as a short interfering nucleic acid (siNA), a short interfering RNA (siRNA), a double-stranded RNA (dsRNA), a micro-RNA (miRNA), and a short hairpin RNA (shRNA).

The terms "short interfering nucleic acid," "siNA," "short interfering RNA," "siRNA," "short interfering nucleic acid molecule," "short interfering oligonucleotide molecule," and "chemically-modified short interfering nucleic acid molecule" as used herein refer to any nucleic acid molecule capable of inhibiting or down regulating gene expression, for example by mediating RNA interference "RNAi" or gene silencing in a sequence-specific manner. Design of RNAi molecules, given a target gene, is routine in the art. See also US 2005/0282188 (which is incorporated herein by reference) as well as references cited therein. See, e.g., Pushparaj et al. Clin Exp Pharmacol Physiol. 2006 May-June; 33(5-6): 504-10; Lutzelberger et al. Handb Exp Pharmacol. 2006; (173):243-59; Aronin et al. Gene Ther. 2006 March; 13(6): 509-16; Xie et al. Drug Discov Today. 2006 January; 11(1-2):67-73; Grunweller et al. Curr Med. Chem. 2005; 12(26): 3143-61; and Pekaraik et al. Brain Res Bull. 2005 Dec. 15; 68(1-2):115-20. Epub 2005 Sep. 9.

Methods for design and production of siRNAs to a desired target are known in the art, and their application to PKD1 genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

Suitable PKD1 gene targets include, e.g., a contiguous stretch of from about 10 nucleotides (nt) to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, of nucleotides 1-2739 of PKD1 mRNA (GenBank NM_002742). Nucleotides 1-2739 of PKD1 mRNA (GenBank NM_002742) are shown in FIGS. 12A and 12B (SEQ ID NO:2).

Non-limiting examples of suitable target nucleic acids include:

```
                                              (SEQ ID NO: 17)
1)     5'-AAAGAGTGTTTGTTGTTATGG-3';

(SEQ ID NO: 18)
2)     5'-ACGCCTGAAAGAGTGTTTGTTGTTATGGAA-3';

(SEQ ID NO: 19)
3)     5'-ACGCCTGAAAGAGTGTTTGT-3';

(SEQ ID NO: 20)
4)     5'-GAGTGTTTGTTGTTATGGAA-3';

(SEQ ID NO: 21)
5)     5'- GAGTGTTTGTTGTTATGGAAAAACTCCATG-3'.
```

Other suitable target sequences will be readily apparent upon inspection of a sequence alignment of the nucleotide sequences provided in GenBank Accession No. NM_002742 (*Homo sapiens*); GenBank Accession No. XM_001170806.1 (*Pan troglodytes*); GenBank Accession No. XM_001114639.1 (*Macaca mulatta*); GenBank Accession No. XM_612625.4 (*Bos taurus*); GenBank Accession No. XM_846293.1 (*Canis familiaris*); GenBank Accession No. XM_0011489357.2 (*Equus caballus*); GenBank Accession No. XM_001078506.1 (*Rattus norvegicus*); and GenBank Accession No. NM_008858.3 (*Mus musculus*).

It should be understood that the sequences provided above are the target sequences of the mRNAs encoding the target gene, and that the siRNA oligonucleotides used would comprise a sequence complementary to the target.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at the post-transcriptional level or the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of PKD1.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi in cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes include those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, polymerase chain reaction (PCR)-generated fragments comprising one or more promoters and an appropriate template or templates for the interfering RNA. The present disclosure provides a recombinant expression vector comprising a nucleotide sequence encoding an interfering RNA. The nucleotide sequence encoding the interfering RNA can be operably linked to a promoter, e.g., an inducible promoter, a neuron-specific promoter, a constitutive promoter, etc.

Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., human immunodeficiency virus-based vectors, feline immunodeficiency virus-based vectors, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.).

In some embodiments, an interfering RNA-encoding nucleotide sequence is operably linked to a neuron-specific control element (e.g., a promoter, an enhancer). Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; and a CMV enhancer/platelet-derived growth factor-13 promoter (see, e.g., Liu et al. (2004) Gene Therapy 11:52-60).

An interfering RNA can be delivered in a delivery system that provides tissue targetable delivery. In addition, a suitable formulation for an interfering nucleic acid can include one or more additional properties: 1) nucleic acid binding into a core that can release the siRNA into the cytoplasm; 2) protection from non-specific interactions; 3) and tissue targeting that provides cell uptake. In some embodiments, the composition comprises a modular polymer conjugate targeting glial cells, neurons, or a subset of neurons by coupling a peptide ligand specific for those cells to one end of a protective polymer, coupled at its other end to a cationic carrier for nucleic acids. For example, a suitable polymer conjugate can have three functional domains: peptide ligand specific for a target cell; protective polymer; and cationic carrier for nucleic acids. Another suitable formulation includes surface coatings attached to a preformed nanoparticle.

Suitable formulations for delivery of an interfering nucleic acid include polymers, polymer conjugates, lipids, micelles, self-assembly colloids, nanoparticles, sterically stabilized nanoparticles, and ligand-directed nanoparticles.

The present disclosure provides a composition comprising a subject interfering nucleic acid. A subject interfering nucleic acid composition can comprise, in addition to a subject interfering nucleic acid, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; glycerol; and the like.

The present disclosure further provides pharmaceutical compositions comprising a subject interfering nucleic acid. Thus, the present disclosure provides a pharmaceutical composition comprising a subject interfering nucleic acid and a pharmaceutically acceptable excipient. Pharmaceutically acceptable excipients are described below.

Recombinant Expression Vector

In some embodiments, a subject method involves administering to an individual in need thereof an effective amount of a recombinant expression vector that provides for production of a nucleic acid that reduces the level of PKD1 polypeptide in a neuron and/or a glial cell, e.g., a recombinant expression vector comprising a nucleotide sequence that encodes an interfering nucleic acid that selectively reduces the level of a PKD1 polypeptide in a neuronal or glial cell that produces PKD1. Thus, in some embodiments, a recombinant expression vector is administered to an individual in need thereof, where the recombinant expression vector comprises a nucleotide sequence encoding an interfering RNA that specifically reduces a PKD1 transcript and/or polypeptide in a cell (e.g., in a neuron or a glial cell). In some embodiments, the nucleotide sequence encoding an interfering RNA that specifically reduces a PKD1 transcript and/or polypeptide in a cell is operably linked to a transcriptional control element (e.g., a promoter) that is active in a neuron or a glial cell.

The present disclosure further provides a recombinant expression vector that comprises a nucleotide sequence encoding a subject interfering nucleic acid, as well as compositions, including pharmaceutical compositions, that comprise a subject recombinant expression vector.

Expression vectors generally have convenient restriction sites located near the promoter sequence to provide for the insertion of nucleic acid sequences encoding a gene product of interest (e.g., an interfering nucleic acid). A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol V is Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol V is Sci 38:2857 2863, 1997; Jomary et al., Gene Ther 4:683 690, 1997, Rolling et al., Hum Gene Ther 10:641648, 1999; Ali et al., Hum Mol Genet. 5:591594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

Non-limiting examples of suitable eukaryotic promoters (promoters functional in a eukaryotic cell) include cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In some embodiments, an interfering RNA-encoding nucleotide sequence is operably linked to a neuron-specific control element (e.g., a promoter, an enhancer). Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; and a CMV enhancer/platelet-derived growth factor-13 promoter (see, e.g., Liu et al. (2004) Gene Therapy 11:52-60).

A recombinant vector will in some embodiments include one or more selectable markers. In addition, the expression vectors will in many embodiments contain one or more selectable marker genes to provide a phenotypic trait for selection of transformed host cells such as dihydrofolate reductase or neomycin resistance for eukaryotic cell culture.

Other gene delivery vehicles and methods may be employed, including polycationic condensed DNA linked or unlinked to killed adenovirus alone, for example Curiel (1992) Hum. Gene Ther. 3:147-154; ligand linked DNA, for example see Wu (1989) J. Biol. Chem. 264:16985-16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) Mol. Cell. Biol. 14:2411-2418, and in Woffendin (1994) Proc. Natl. Acad. Sci. 91:1581-1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 524 968.

Liposome or lipid nucleic acid delivery vehicles can also be used. Liposome complexes for gene delivery are described in, e.g., U.S. Pat. No. 7,001,614. For example, liposomes comprising DOTAP and at least one cholesterol and/or cholesterol-derivative, present in a molar ratio range of 2.0 mM 10 mM provide an effective delivery system, e.g., where the molar ratio of DOTAP to cholesterol is 1:1 3:1. The cationic lipid N-[(2,3-dioleoyloxy)propyl]-L-lysinamide (LADOP) can be used in a composition for delivering a polynucleotide, where LADOP-containing liposomes are described in, e.g., U.S. Pat. No. 7,067,697. Liposome formulations comprising amphipathic lipids having a polar headgroup and aliphatic components capable of promoting transfection are suitable for use and are described in, e.g., U.S. Pat. No. 6,433,017. Lipid-conjugated polyamide compounds can be used to deliver nucleic acid; see, e.g., U.S. Pat. No. 7,214,384.

Suitable synthetic polymer-based carrier vehicles are described in, e.g., U.S. Pat. No. 6,312,727. Further non-viral delivery suitable for use includes mechanical delivery systems such as the approach described in Woffendin et al. (1994) Proc. Natl. Acad. Sci. USA 91:11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

The present disclosure provides a composition comprising a subject recombinant expression vector. A subject interfering nucleic acid composition can comprise, in addition to a subject recombinant expression vector, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; glycerol; and the like.

The present disclosure further provides pharmaceutical compositions comprising a subject recombinant expression vector. Thus, the present disclosure provides a pharmaceutical composition comprising a subject recombinant expression vector and a pharmaceutically acceptable excipient. Pharmaceutically acceptable excipients are described below.

Combination Therapies

In some embodiments, a subject treatment method comprises administering to an individual in need thereof an active agent that modulates PKD1 activity levels in a cell (e.g., in a neuron and/or a glial cell); and further comprises administering at least one additional therapeutic agent.

Suitable additional therapeutic agents include agents for treating AD, where such agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept is generally administered at 50 mg orally per day for 6 weeks, and, if well tolerated by the individual, at 10 mg per day thereafter.

Another suitable additional therapeutic agent for treating AD is an apoE4 "structure corrector" that reduces apoE4 domain interaction. Agents that reduce apoE4 domain interaction include, e.g., an agent as described in U.S. Patent Publication No. 2006/0073104); and in Ye et al. (2005) Proc. Natl. Acad. Sci. USA 102:18700.

Another suitable additional therapeutic agent for treating AD is an agent that inhibits tau aggregation, e.g., a napthoquinone derivative that inhibits tau aggregation, as described in U.S. Pat. No. 7,605,179. Another suitable additional therapeutic agent is an agent that inhibits phosphorylation of tau, e.g., a 3-substituted-4-pyrimidone derivative that inhibits tau protein kinase 1, as described in U.S. Pat. No. 7,572,793.

Suitable additional therapeutic agents include agents for treating Huntington's disease or a symptom of Huntington's disease, where such agents include, but are not limited to, tetrabenazine, clonazepam, haloperidol, clozapine, fluoxetine, sertraline, and nortriptyline.

Suitable additional therapeutic agents include agents for treating Parkinson's disease or a symptom of Parkinson's disease, where such agents include, but are not limited to, levodopa; dopamine agonists (e.g., bromocriptine, apomorphine, pramipexole, ropinirole); anticholinergic agents (e.g., trihexyphenidyl, benztropine, ethopropazine); monoamine oxidase-B inhibitors (e.g., selegiline); catechol-O-methyltransferase inhibitors (e.g., entacapone, tolcapone); and amantadine.

Suitable additional therapeutic agents include agents for treating multiple sclerosis, where such agents include, but are not limited to, interferon-β (e.g., interferon-β1a, interferon-β1b); glatiramer acetate; a cancer chemotherapeutic agent (e.g., mitoxantrone, azathioprine, cyclophosphamide, methotrexate, cladribine); corticosteroids (e.g., methylprednisolone, prednisone, dexamethasone).

Formulations, Dosages, and Routes of Administration

As discussed above, a subject treatment method generally involves administering to an individual in need thereof an effective amount of an agent that modulates PKD1 activity levels in a neuron and/or a glial cell. Formulations, dosages, and routes of administration are discussed below. For the purposes of the discussion of formulations, dosages, and routes of administration, the term "active agent" refers to one or more of a subject antibody, a subject interfering nucleic acid, and a small molecule modulator of PKD1 activity.

The present disclosure also provides pharmaceutical compositions comprising a subject antibody. The present disclosure also provides pharmaceutical compositions comprising a subject interfering nucleic acid.

In some instances, a composition comprising an agent that modulates PKD1 activity can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins Formulations In the subject methods, the active agent(s) may be administered to the host using any convenient means capable of resulting in the desired therapeutic effect or clinical outcome. Thus, an active agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent may be administered in the form of its pharmaceutically acceptable salt, or an active agent may also be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. The compounds of the present invention can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise an active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for a suitable dosage form depend, e.g., on the particular active agent employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition can include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of an active agent by the nasal mucosa.

An active agent can be administered in a composition suitable for injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Oral Formulations

In some embodiments, an active agent is formulated for oral delivery to an individual in need of such an agent.

For oral delivery, a formulation comprising an active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, an active agent is formulated with one or more pharmaceutical excipients and coated with an enteric coating, as described in U.S. Pat. No. 6,346,269. For example, a solution comprising an active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for an active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include an active agent formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly (lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B. V.).

Suitable oral formulations also include an active agent formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoyl-carnitine, and sodium salts of fatty acids); toxins (e.g., zonula occludens toxin); and the like.

Controlled Release Formulations

In some embodiments, an active agent is formulated in a controlled release formulation.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems*, 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. In one exemplary embodiment, an active agent can be contained in an enterically coated multiple-unit dosage form. In an exemplary embodiment, a dosage form comprising an active agent is prepared by spray-coating granules of the active agent-enteric coating agent solid dispersion on an inert core material. These granules can result in prolonged absorption of the active agent with good bioavailability.

Typical enteric coating agents include, but are not limited to, hydroxypropylmethylcellulose phthalate, methacryclic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form*, Chem. Pharm. Bull. 33: 1615-1619 (1985). Various enteric coating materials may be selected on the basis of testing to achieve an enteric coated dosage form designed ab initio to have an optimal combination of dissolution time, coating thicknesses and diametral crushing strength. S. C. Porter et al., *The Properties of Enteric Tablet Coatings Made From Polyvinyl Acetate-phthalate and Cellulose acetate Phthalate*, J. Pharm. Pharmacol. 22:42p (1970).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, *Super Saturation Mechanism of Drugs from Solid Dispersions with Enteric Coating Agents*, Chem. Pharm. Bull. 36: 4941-4950 (1998). The solid dispersions may be also called solid-state dispersions. The term "coprecipitates" may also be used to refer to those preparations obtained by the solvent methods.

The selection of the carrier may have an influence on the dissolution characteristics of the dispersed active agent because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of an active agent may also be increased owing to some interaction with the carriers.

Examples of carriers useful in solid dispersions include, but are not limited to, water-soluble polymers such as polyethylene glycol, polyvinylpyrrolidone, and hydroxypropylmethylcellulose. Alternative carriers include phosphatidylcholine. Phosphatidylcholine is an amphoteric but water-insoluble lipid, which may improve the solubility of otherwise insoluble active agents in an amorphous state in phosphatidylcholine solid dispersions.

Other carriers include polyoxyethylene hydrogenated castor oil. Poorly water-soluble active agents may be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of an active agent with ethyl cellulose and stearic acid in different ratios.

There are various methods commonly known for preparing solid dispersions. These include, but are not limited to, the melting method, the solvent method and the melting-solvent method.

Another controlled release dosage form is a complex between an ion exchange resin and an active agent. Ion exchange resin-drug complexes have been used to formulate sustained-release products of acidic and basic drugs. In one exemplary embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs*, J. Pharm. Sciences 70: 379-384 (1981).

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid). Shigeyuki Takada, *Utilization of an Amorphous Form of a Water-Soluble GPIIb/IIIa Antagonist for Controlled Release From Biodegradable Micro spheres*, Pharm. Res. 14:1146-1150 (1997), and ethyl cellulose, Yoshiyuki Koida, *Studies on Dissolution Mechanism of Drugs from Ethyl Cellulose Microcapsules*, Chem. Pharm. Bull. 35:1538-1545 (1987).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate-release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet, production of which is comprised of two distinct steps: the drug in question is converted to an amorphous form through a combination of energy, excipients, and unique processing procedures.

Once converted to the desirable physical form, the resultant high energy complex may be stabilized by an absorption process that utilizes a novel polymer cross-linked technology to prevent recrystallization. The combination of the change in the physical state of an active agent coupled with the solubilizing characteristics of the excipients employed enhances the solubility of the active agent. The resulting absorbed amorphous drug complex granulate may be formulated with a gel-forming erodible tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of drug being both released locally and absorbed systemically. The combination of both approaches serves to minimize the potential harm of an active agent with resultant benefits to patients.

IPDAS is composed of numerous high density controlled release beads. Each bead may be manufactured by a two step process that involves the initial production of a micromatrix with embedded active agent and the subsequent coating of this micromatrix with polymer solutions that form a rate-limiting semipermeable membrane in vivo. Once an IPDAS tablet is ingested, it may disintegrate and liberate the beads in the stomach. These beads may subsequently pass into the duodenum and along the gastrointestinal tract, e.g., in a controlled and gradual manner, independent of the feeding state. Release of the active agent occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

MODAS is a drug delivery system that may be used to control the absorption of water soluble agents. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver an active agent. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain an active agent. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used to an active agent. DUREDAS was developed to provide for two different release rates, or dual release of a drug from one dosage form. The term bilayer refers to two separate direct compression events that take place during the tableting process. In an exemplary embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of an active agent may be desirable in order to facilitate a fast onset of therapeutic affect. Hence one layer of the tablet may be formulated as an immediate release granulate. By contrast, the second layer of the tablet may release the drug in a controlled manner, e.g., through the use of hydrophilic polymers. This controlled release may result from a combination of diffusion and erosion through the hydrophilic polymer matrix.

A further extension of DUREDAS technology is the production of controlled release combination dosage forms. In this instance, two different active agents may be incorporated into the bilayer tablet and the release of drug from each layer controlled to maximize therapeutic affect of the combination.

An active agent can be incorporated into any one of the aforementioned controlled released dosage forms, or other conventional dosage forms. The amount of active agent contained in each dose can be adjusted, to meet the needs of the individual patient, and the indication. One of skill in the art and reading this disclosure will readily recognize how to adjust the level of an active agent and the release rates in a controlled release formulation, in order to optimize delivery of the active agent and its bioavailability.

Inhalational Formulations

An active agent will in some embodiments be administered to a patient by means of a pharmaceutical delivery system for the inhalation route. An active agent may be formulated in a form suitable for administration by inhalation. The inhalational route of administration provides the advantage that the inhaled drug can bypass the blood-brain bather. The pharmaceutical delivery system is one that is suitable for respiratory therapy by delivery of an active agent to mucosal linings of the bronchi. This invention can utilize a system that depends on the power of a compressed gas to expel an active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains an active agent, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An active agent can also be formulated for delivery with a nebulizer, which is an instrument that generates very fine liquid particles of substantially uniform size in a gas. For example, a liquid containing an active agent is dispersed as droplets. The small droplets can be carried by a current of air through an outlet tube of the nebulizer. The resulting mist penetrates into the respiratory tract of the patient.

A powder composition containing an active agent, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present invention. An active agent can be formulated in basically three different types of formulations for inhalation. First, an active agent can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, an active agent can be formulated in aqueous or ethanolic solutions and delivered by conventional nebulizers. Lastly, an active agent can be formulated into dry powder formulations. Such formulations can be administered by simply inhaling the dry powder formulation after creating an aerosol mist of the powder.

Dosages

Although the dosage used will vary depending on the clinical goals to be achieved, a suitable dosage range is one which provides up to about 1 µg to about 1,000 µg or about 10,000 µg of an active agent and can be administered in a single dose. Alternatively, a target dosage of an active agent can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intracranial, subcutaneous, intradermal, topical application, intravenous, rectal, nasal, oral and other enteral and parenteral routes of administration. Routes of administration may be combined, if desired, or adjusted depending upon the agent and/or the desired effect. The composition can be administered in a single dose or in multiple doses. In some embodiments, the composition is administered orally. In other embodiments, the composition is administered intravenously. In other embodiments, the composition is administered via an inhalational route. In other embodiments, the composition is administered intramuscularly.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a neurological disorder and pain that may be associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Subjects Suitable for Treatment

Subjects that can be treated with a subject method include individuals who have been diagnosed as having a neurodegenerative disorder, a demyelinating disease, acute brain injury, spinal cord injury, or other disorder or condition that involves neuronal cell death or dysfunction. Subjects suitable for treatment with a subject method also include individuals who have been treated for a neurodegenerative disorder or a demyelinating disease, and who have either failed to respond to the treatment, or who initially responded to the treatment, but relapsed.

Genetically Modified Non-Human Mammals Deficient in PKD1

The present disclosure provides a genetically modified non-human mammal that is deficient in PKD1. Such a genetically modified non-human animal is also referred to herein as a "PKD1 knockout non-human mammal." A subject PKD1 knockout non-human mammal can be used: 1) for carrying out research relating to the role of PKD1 in neurological disorders; 2) for testing compounds that are candidates for treating a neurological disorder; and 3) as a source of isolated PKD1 knockout cells that can be used in vitro for assessing candidate compounds. In some embodiments, a subject PKD1 knockout non-human mammal is a mouse.

A subject PKD1 knockout non-human mammal exhibits spatial memory deficits. A subject PKD1 knockout non-human mammal can be used to identify agents that enhance spatial memory. For example, a test agent is administered to a subject PKD1 knockout non-human mammal; and the effect, if any, of the test agent on spatial memory is assessed. The Morris water maze test can be used to assess the effect of a test agent on spatial memory. A test agent that enhances spatial memory is a candidate agent for treating a neurological disorder characterized by spatial memory deficit.

A "PKD1 knockout non-human mammal" is a mammal in which the function of one or more alleles of an endogenous PKD1 gene has been altered, for example, by homologous recombination or other insertion or deletion. In certain embodiments, the endogenous PKD1 gene is disrupted. By "disrupted gene" is meant at least a portion of the genetic code encoding PKD1 has been altered, thereby affecting transcription and/or translation of that segment of the genetic code, e.g., rendering that segment of the code unreadable through knockout techniques or by insertion of an additional gene for a desired protein or insertion of a regulatory sequence that modulates transcription of an existing sequence. In some embodiments, all of the cells of the PKD1 knockout non-human mammal include the disrupted gene. In certain embodiments, the PKD1 knockout non-human mammal is a mammal in which one or both alleles of the endogenous PKD1 gene has been rendered nonfunctional. In some embodiments, both alleles of the endogenous PKD1 gene are rendered non-functional. Such embodiments include those commonly referred to as "gene knockouts," "gene knock-ins" and any other modification of one or more native allele of the native (endogenous) PKD1 gene that renders such gene non-functional.

In some embodiments, one or both endogenous PKD1 alleles is knocked out only in cells of the central nervous system (CNS). For example, a first genetically modified non-human mammal that expresses a Cre recombinase under the control of a neuron-specific promoter is bred with a second genetically modified non-human mammal of the same species as the first genetically modified non-human mammal that comprises a lox site in a PKD1 gene; the offspring of the first and the second non-human mammals then have a PKD1 knockout in cells of the CNS, but not in cells other than CNS cells.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; and a CMV enhancer/platelet-derived growth factor-$\beta$ promoter (see, e.g., Liu et al. (2004) *Gene Therapy* 11:52-60).

An endogenous PKD1 allele can be modified by homologous recombination with a DNA encoding a defective PKD1, such as a nucleotide sequence containing within the coding sequence an antibiotic marker, which antibiotic marker can then be used for selection purposes. Methods of making knockout mammals are well known in the art. See, e.g, U.S. Pat. No. 7,547,816 and U.S. Pat. No. 7,514,592. The following description provides examples.

Animal Sources

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats and can easily be extended to other species when analogous techniques are developed.

Microinjection Procedures

The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein.

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5 C incubator with a humidified atmosphere at 5% $CO_2$, 95% air until the time of injection.

Randomly cycling adult females are mated with vasectomized males to induce a false pregnancy, at the same time as donor females. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

Introduction of Exogenous DNA into ES Cells for Making Transgenic or Knockout Mammals Methods for the culturing of ES cells and the subsequent production of transgenic animals, the introduction of DNA into ES cells by a variety of methods such as electroporation, calcium phosphate/DNA precipitation, and direct injection are described in detail in "Teratocarcinomas and embryonic stem cells, a practical approach," ed. E. J. Robertson, (IRL Press 1987), the teachings of which are incorporated herein. Gene transfer can be carried out by homologous recombination. Selection of the desired clone of transgene-containing ES cells is accomplished through one of several means. Transfection is carried out by one of several methods described in detail in Current Protocols in Molecular Biology: Ch. 9 Introduction of DNA into Mammalian Cells; John Wiley & Sons, New York, N.Y., 2001). Calcium phosphate/DNA precipitation, direct injection, and electroporation are examples of suitable methods. In these procedures, a number of ES cells, for example, $0.5 \times 10^6$, are plated into tissue culture dishes and transfected with a mixture of the linearized nucleic acid construct containing the gene of interest. Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, Nature 338, 150-153 (1989)). DNA introduction by electroporation can also be used. Methods for positive selection of the recombination event (i.e., neomycin (neo) resistance) and dual positive-negative selection (i.e., neo resistance and ganciclovir resistance) and the subsequent identification of the desired clones by PCR have been described by Joyner et al., Nature 338, 153-156 (1989) and Capecchi, (1989), the teachings of which are incorporated herein. The target sequence can also be "floxed" using methods reviewed in Sauer (Methods. 1998 April; 14(4):381-92) for removal by crossing with an appropriate expresser of cre-recombinase.

As an example, a DNA construct used as the knockout construct can include: i) a nucleotide sequence from some portion of the PKD1 gene, for example, exon sequence, intron sequence and/or promoter sequence; and ii) a marker sequence used to detect the presence of the DNA construct in a cell. The DNA construct is inserted into a cell and integrates with the genomic DNA of the cell in such a position so as to prevent or interrupt transcription of the native PKD1 DNA sequence. Such insertion can occur by homologous recombination, in which regions of the DNA construct that are homologous to endogenous PKD1 DNA sequences hybridize to each other when the DNA construct is inserted into the cell and recombine so that the DNA construct is incorporated into the corresponding position of the endogenous PKD1 DNA. The DNA construct sequence can comprise a full or partial sequence of one or more exons and/or introns of the PKD1 gene, a full or partial promoter sequence of the PKD1 gene, or combinations thereof.

When used to disrupt the expression of an endogenous gene in an animal, the DNA construct will generally contain an insert in the homologous region. The insert can be, for example, a selectable marker. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the invention, including, for example, Neo, Hyg, hisD, Gpt and Ble genes, as described, for example in Ausubel et al. (Current Protocols in Molecular Biology (Supplement 47), John Wiley & Sons, New York (1999) and U.S. Pat. No. 5,981,830). Drugs useful for selecting for the presence of a selectable marker includes, for example, G418 for Neo, hygromycin for Hyg, histidinol for hisD, xanthine for Gpt, and bleomycin for Ble (see Ausubel et al., supra, (1999); and U.S. Pat. No. 5,981,830). DNA constructs of the invention can incorporate a positive selectable marker, a negative selectable marker, or both (see, for example, U.S. Pat. No. 5,981,830).

Embryo Recovery and ES Cell Injection

Naturally cycling or superovulated females mated with males are used to harvest embryos for the injection of ES cells. Embryos of the appropriate age are recovered after successful mating. Embryos are flushed from the uterine horns of mated females and placed in Dulbecco's modified essential medium plus 10% calf serum for injection with ES cells. Approximately 10-20 ES cells are injected into blastocysts using a glass microneedle with an internal diameter of approximately 20 m.

Transfer of Embryos to Pseudopregnant Females

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

Identification of Transgenic Animals

Samples (1-2 cm of mouse tails) are removed from young animals. For larger animals, blood or other tissue can be used. To test for chimeras in the homologous recombination experiments, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$).

Once the transgenic animals are identified, lines are established by conventional breeding. Dual species crosses can be obtained by cross mating and breeding to homozygosity. Methods of breeding transgenic mice are routine in the art.

Further Genetic Modifications

The PKD1 knockout and double knockouts can be crossed with other types of genetically modified animals (either naturally occurring mutations or genetically engineered animals). Many such animals are described in the literature and available from companies such as Jackson Laboratories, Bar Harbor, Me. As one non-limiting example, a PKD1 knockout animal can also include a genetic modification such that a pathological form of amyloid precursor protein (APP) is produced in the animal. For example, a transgenic mouse can comprise, in addition to a PKD1 knockout, a human amyloid precursor protein (hAPP) mutant transgene; a presenilin1 or a presenilin2 transgene; and the like. See, e.g., Götz et al. (2004) *Mol. Psychiatry* 9:664; Götz and Ittner (2008) *Nature Reviews* 9:532.

Cells

The present disclosure further provides cells isolated from a subject PKD1 knockout mammal. A subject isolated cell comprises a defect in one or both alleles of an endogenous PKD1 gene, such that the gene is defective and PKD1 is not synthesized by the cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Protein Kinase D1 Receives Distinct Signals from NMDARs and mGluRs and Regulates AMPAR Trafficking and Subunit Composition Experimental Procedures Cortical Cultures Embryonic mouse primary cortical neurons were cultured and $NR^{-/-}$ neurons were genotyped as described (Bradley et al., 2006). For experiments not including $NR^{-/-}$ neurons, wild-type C57/BL6 mice (Charles River) were used. Neurons from E18-19 embryos were plated at a density of $0.6 \times 10^6$ cells/cm$^2$ on 12 mm glass coverslips coated with poly D-lysine and maintained in Neurobasal medium supplemented with B27 (Invitrogen). Experiments were done at 8-14 days in vitro (DIV). Neurons were transfected with the calcium phosphate method (Bradley et al., 2006).

Reverse Transcription Polymerase Chain Reaction (RT-PCR)

Total RNA was extracted from C57/BL6 mouse brain with RNEasy kits (Qiagen). Complementary DNA (cDNA) was generated with SuperScript II reverse transcriptase. Protein Kinase D1 (PKD1), D2 (PKD2), and D3 (PKD3) were amplified by polymerase chain reaction (PCR) with isoform specific primers as described (Oster et al., 2006).

Generation of PKD Isoform-Specific Antisera

PKD1-Specific Antibodies

For PKD1-specific antibodies, three regions of PKD1 (amino acids 203-261, 333-410, and 875-918) were cloned and expressed as GST-fusion proteins. All three proteins were mixed and injected into rabbits to generate polyclonal antibodies.

Protein 1 (59 aa: 203-261)

Protein Sequences (6.3 kDa, pI=6.62)

(SEQ ID NO: 3)
SNVSLTGLGTVRTASAEFSTSVPDEPLLSPVSPGFEQKSPSESFIGREKR

SNSQSYIGR

Protein 2 (78aa: 333-410)

Protein Sequences (8.6 kDa, pI=3.46)

(SEQ ID NO: 4)
NGELLSPGAESDVVMEEGSDDNDSERNSGLMDDMDEAMVQDTEMALAEGQ

SGGAEMQDPDADQEDSNRTISPSTSNNI

Protein 3 (44aa: 875-918)

Protein Sequences (4.9 kDa, pI 4.63)

(SEQ ID NO: 5)
WEQYAGEQGLQYPAHLISLSASHSDSPEAEEREMKALSERVSIL.

PKD2- and PKD3-Specific Antibodies

For PKD2 and 3-specific antibodies, the first 80 amino acids of PKD2 and 3 were cloned and expressed as GST-fusion proteins.

PKD2

Protein Sequences (8.0 kDa, pI=6.77)

(SEQ ID NO: 22)
MAAAPSHPAGLPGSPGPGSPPPPGGLDLQSPPPLLPQIPAPGSGVSFHIQ

IGLTREFVLLPAASELAHVKQLACSIVDQK

PKD3

Protein Sequences (8.2 kDa, pI=9.16)

(SEQ ID NO: 23)
MSANNSPPSAQKSVFPATVSAVLPAPSPCSSPKTGLSARLSNGSFSAPSL

TNSRGSVHTVSFLLQIGLTRESVTIEAQEL

Recombinant PKD1 (amino acids 203-261, 333-410, and 875-918) and PKD3 (amino acids 1-80) were expressed in bacteria with the pGEX-4T-1 vector (Amersham). Glutathione-S-transferase-PKD fusion proteins were solubilized in nondenaturing buffer and purified over glutathione Sepharose 4B (GE Healthcare). Rabbits were immunized with the recombinant proteins and antisera were affinity purified by YenZym Antibodies.

Western Blots

Neurons were lysed with ice-cold RIPA buffer (1% Triton X-100, 0.1% sodium dodecyl sulfate (SDS), 50 mM Tris-HCl, 150 mM NaCl, 1 mM EDTA, 10 mM NaF, and protease inhibitor cocktail; Roche). Samples were centrifuged, and supernatants were loaded onto gels, separated by sodium dodecyl sulfate-polyacrylamide gel electrophoresis (SDS-PAGE), transferred to nitrocellulose membranes, and probed with antibodies against pan-PKD1 (1:1000, Cell Signaling or 1:5000, HJK), phospho-S744/8 PKD1 (1:1000, Cell Signaling), phospho-5916 PKD1 (1:1000, Cell Signaling), β-actin (1:4000, Sigma) or anti-tubulin (1:500,000, Sigma). Anti-rabbit or anti-mouse secondary antibodies conjugated to horseradish peroxidase were used on all blots and imaged by enhanced chemiluminescence (Amersham Biosciences) or with SuperSignal West Femto substrate (Pierce).

Immunocytochemistry

Cells were fixed in 4% paraformaldehyde with 4% sucrose for 10 min and blocked in phosphate-buffered saline (PBS) with 3% bovine serum albumin, 2% goat or donkey serum, and 0.1% Triton-X100. For surface staining, primary antibody was applied to live cells for 45 min before fixation, and detergent was omitted from the blocking step. The primary antibody concentrations were: PKD1 (1:5000, HJK), PKD2 (1:2000, Bethyl Laboratories) PKD3 (1:5000, HJK) MAP2 (1:400, Chemicon), HA (1:1000, Cell Signaling), GluR2 (1:300, Millipore), Rab5 (1:100 PKD1 Receives Distinct Signals from NMDARs and mGluRs and Regulates α-amino-3-hydroxy-5-methyl-4-isoxazolepropionic acid receptor (AMPAR) Trafficking and Subunit Composition, BD Biosciences), LAMP1 (1:200, Stressgen), or Syntaxin13 (1:50, AbCam). All fluorescent secondary antibodies were used at 1:250 (Invitrogen).

Pharmacology

Stimulations were performed at room temperature in HEPES-buffered saline (HBS: 119 mM NaCl, 2.5 mM KCl, 2 mM $MgCl_2$, 2 mM $CaCl_2$, 25 mM HEPES, 30 mM glucose, 1 μM tetrodotoxin, 10 μM NBQX, pH 7.4). For all stimulations except those using high levels of $K^+$, 25 μM nimodipine was included in the HBS. Neurons were incubated in HBS for 30-60 min before stimulation. Doses used (unless otherwise indicated): phorbol 12-myristate 13-acetate (PMA; 100 nM); glutamate (30 μM with 10 μM glycine); D,L-2-amino-5-phosphonovaleric acid (APV; 100 μM), N-methyl-D-aspartate (NMDA; 100 μM with 10 μM glycine); alpha-methyl-4-carboxyphenylglycine (MCPG; 1 mM); (1S,3R)-1-aminocyclopentane-1,3-dicarboxylic acid (ACPD; 100 μM); and $K^+$ (55 mM).

Field Stimulation

At 14 DIV, transfected neurons in coverslips were transferred to a custom-designed field stimulator with two parallel platinum electrodes suspended in the medium approximately 1 mm from the cell monolayer. Neurons were stimulated in HBS as described above, except $Mg^{2+}$ was omitted. Stimulation (5 Hz for 15 min, 1-ms pulse width) was delivered with a D330 MultiStim (Digitimer).

Imaging and Analysis

For puncta analysis, images were taken with an inverted epifluorescence microscope (Nikon, Japan) and a cooled charge coupled device (CCD) digital camera (Hamamatsu Orca II) (Arrasate and Finkbeiner, 2005). Venus-PKD1 and mCherry images of the same field were taken before and after stimulation. Calculations of puncta indices (PIs) were based on a previous study (Bradley et al., 2006). PIs were calculated with MetaMorph software (Molecular Devices) as the standard deviation (SD) of Venus fluorescence along a region of dendrite divided by the SD of mCherry fluorescence along the same region. Puncta formation was determined by calculating PIs both before and after a 60-min stimulation with glutamate and expressed as the ratio of PI (time 60)/PI (time 0). Dendrites were excluded from analysis if the SD of their mCherry intensities changed after stimulation. For spontaneous puncta formation, longitudinal analysis was adapted from a previous study (Arrasate and Finkbeiner, 2005). Fields of neurons were located on the first day of imaging and revisited each day thereafter with a robotic microscope. Images were taken beginning at 13 DIV and ending at 21 DIV. In colocalization studies, images were obtained with a Zeiss LSM 510 laser scanning confocal microscope. Images were minimally processed with ImageJ. Thresholds for puncta were set to five-fold mean background intensity for each channel. Thresholding and overlap quantification was performed in MetaMorph software.

Constructs

GW1-Venus-PKD1 was created from a Clontech vector containing green fluorescent protein-protein kinase D1 (GFP-PKD1) described previously (Rey et al., 2004). A 46-amino acid stretch links Venus to the N-terminus of mouse PKD1. The point mutation in Venus-PKD1 was generated with a site-directed mutagenesis kit (Stratagene) and confirmed by DNA sequencing. CFP-TGN38 was described (McNamara et al., 2004), as were HA-GluR1 and HA-GluR2 (Passafaro et al., 2001).

PKD1 Knockdown

PKD1 shRNA was constructed as a short hairpin RNA in mammalian expression vector pSilencer 2.0 using the target PKD1 sequence AAAGAGTGTTTGTTGTTATGG (SEQ ID NO:17) followed by a 9-bp linker and the inverse 21-bp sequence. The control m-shRNA used the same target sequence with four mutations (underlined): AAAGTGTG ATTGTTGTTTAGG (SEQ ID NO:24). To generate lentiviral constructs of shRNAs, the U6 promoter and short hairpin sequences from the pSilencer constructs were amplified by PCR, subcloned into viral vector FUGW2, and expressed in HEK293FT cells (Invitrogen) along with viral packaging proteins Δ8.9 and VSVG. Viruses were harvested, titered, and used for infection as described (Cronshaw et al., 2002). Neurons were harvested and analyzed 5-7 days after infection.

Array Tomography

Arrays of brain tissue from YFP-H transgenic mice (Feng et al., 2000) were prepared with 70-nm slices as described (Micheva and Smith, 2007). Primary antibodies were incubated on arrays overnight at 4° C. as follows: PKD1 (1:300, HJK), PSD95 (1:50, NeuroMabs) synapsin (1:100, Millipore), GluR2 (1:30, Chemicon), Rab5 (1:100, BD Biosciences), and GM130 (1:50, BD Biosciences). To examine the spatial relationship of the channels of interest, a cross-correlation analysis similar to that of van Steensel and colleagues (van Steensel et al., 1996) was used. For each pair of channels, patches of neuropil were convoluted to find the raw colocalization score, Sr, for a range of lateral offsets. To correct for differences in mean brightness in different channels, the analysis was repeated with one channel transposed (and therefore uncorrelated) to get a baseline score, St. The colocalization index (Ci) of two channels was determined by normalizing by difference-over-sum as Sr−St/Sr+St=Ci. Ci=1 indicates ideal colocalization, Ci=0 no colocalization above chance, and Ci<0 anti-localization. With this method, colocalization of different labels can be objectively compared in a channel-independent manner.

Transferrin Recycling Assay

This assay was adapted from a previous study (Park et al., 2004). Neurons were incubated with Alexa 647-conjugated transferrin (50 μg/mL; Invitrogen) for 60 min in HBS (containing no antagonists) to achieve a steady-state concentration of internalized fluorescently conjugated transferrin. The extracellular fluorescent transferrin was then washed out with an excess of unlabeled transferrin (5 mg/ml, Sigma), and cells were fixed at various times for confocal microscopy. Neurons were selected based on mCherry images; the experimenter was blind to the Alexa 647 content of the cells. Confocal images were taken of the mCherry channel, and Alexa 647 images were taken at identical laser settings for each cell to allow quantitative comparisons. The average pixel intensity of transferrin in mCherry-positive pixels was determined with Zeiss LSM 510 software. Cell bodies were excluded from analysis.

Surface Biotinylation

Primary cortical neurons (7 DIV) were infected with lentivirus encoding either shRNA against PKD1 or control shRNA. Five days after infection, cells were placed on ice and rinsed twice with ice-cold phosphate buffered saline (PBS: 137 mM NaCl, 3 mM KCl, 2 mM $KH_2PO_4$, 10 mM $Na_2HPO_4$). Sulfo-NHS-LC-biotin (2 mg/ml, Pierce) was added, and cells were incubated at 4° C. with gentle rocking. After 30 min, cells were rinsed three times with ice-cold PBS and harvested in PBS containing 1% Triton X-100, 0.1% SDS, and protease cocktail inhibitor with EDTA (Roche). Lysates were sonicated briefly and centrifuged at 13,000 rpm in a tabletop centrifuge at 4° C. Protein concentration was measured by Bradford assay, and lysates were diluted to 200 μg/ml in PBS+1% NP-40. Avidin Sepharose beads (50 μl slurry, Pierce) were added to diluted lysate (500 μl) and incubated overnight at 4° C. Beads were washed three times in ice-cold PBS, and biotinylated protein was eluted by boiling in 2× Laemmli buffer. Surface proteins were analyzed by western blot with anti-GluR2 (1:1000, NeuroMabs), anti-GluR1 (1:200, Millipore), anti-NR1 (1:1000, Upstate Biotechnology), or anti-mGluR1/5 (1:1000, NeuroMAbs). Total protein (40 μg per sample) was reserved and run on parallel western blots to control for expression between samples. Band intensities were quantified with ImageJ Gel Analyzer tool (Abramoff M D, 2004).

Electrophysiology

Recordings were performed in voltage-clamp mode in HBS (119 mM NaCl, 2 mM KCl, 1 mM $MgCl_2$, 1.5 mM $CaCl_2$, 10 mM HEPES, 15 mM glucose, pH 7.35, 235 mOsm) at 25° C., in the presence of 1 μM tetrodotoxin (TTX), 10 μM gabazine, and 100 μM D-APV (added fresh each day) using an Axon Multiclamp amplifier and Clampex acquisition software. Electrode resistance was 3-6 MOhm. The intracellular recording solution was cesium based (120 mM $CsMeSO_3$, 6 mM NaCl, 2 mM $MgCl_2$, 10 mM HEPES, 0.2 mM EGTA, 2 mM $Na_2ATP$, 0.3 mM GTP-Tris) with 50 μM spermine (added fresh each day). For I/V curves, stimulation was achieved using puffs of 5 mM kainic acid, and episodic recordings were taken for 10-mV increments in holding potential from −80 to +40 mV. Series resistance was compensated for and the peak current response at each potential was measured with AxoGraph analysis software. At least three recordings were taken for each cell. The rectification index was calculated by dividing the maximal current amplitude at +40 mV by that at −60 mV. Significance was determined with an unpaired t test.

pHluorin GluR2 Recycling Assay

Rat GluR2 tagged with superecliptic pHluorin was cloned into pGW1 mammalian expression vector. mCherry was subcloned to replace enhanced green fluorescent protein (EGFP) in FUGW PKD1 shRNA and control vectors. mCherry served as a morphology marker to monitor the overall health of the cell. pHluorin-GluR2 and PKD1 shRNA or mutant control were transfected into mouse cortical neurons with Lipofectamine 2000 (Invitrogen). At 12 DIV, neurons were imaged on a Zeiss LSM 510 confocal microscope with a 40× water immersion lens in HBS as described above, only nimodipine was excluded. After 20 min of baseline imaging, 30 μM glutamate and 10 μM glycine were washed on to cells by gravity flow perfusion for 5 min, followed by washout with control HBS solution. Images were collected every 5 min. Average pixel intensity of pH-GluR2 in the cell body was calculated in MetaMorph, and background was measured in a cell-free region of the image and subtracted from fluorescence intensities before further calculations. Fractional change in fluorescent intensity ($\Delta F/F_0$) was calculated as $F_t-F_0/F_0$, where $F_t$ is pHGluR2 intensity at time t and $F_0$ is the average pH-GluR2 fluorescence intensity at four points before glutamate application.

Results

Endogenous PKD1 has a Different Distribution in Neurons than PKD2 and 3

To discover roles for PKD in the nervous system, it was first determined where PKD is found. Transcripts encoding the three known isoforms of PKD were widely expressed in the adult mouse brain, including in cortex, hippocampus, striatum, and cerebellum (FIG. 1A). PKD1, the most abundant isoform, was highly expressed in primary neuronal cultures of mouse cortex and hippocampus, which are well-established model systems for mechanistic studies of synaptic plasticity (Bradley et al., 2006; Rao et al., 2006) and protein trafficking (Horton and Ehlers, 2003; Horton et al., 2005). PKD1 levels were high and relatively constant at 2, 7, and 14 days in vitro (DIV) (FIG. 1B), when synapses form and mature.

Figure 9A:
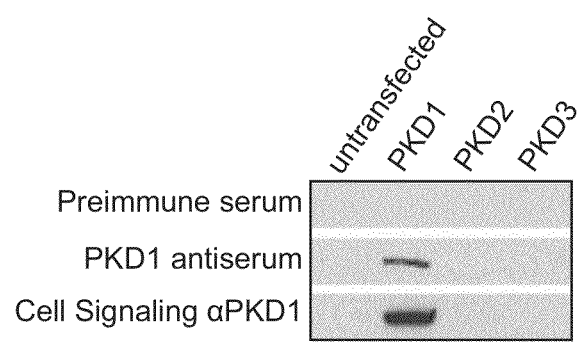
FIGS. 9A and 9B depict the specificity of PKD1- and PKD3-specific polyclonal antibodies.
Figure 9B:
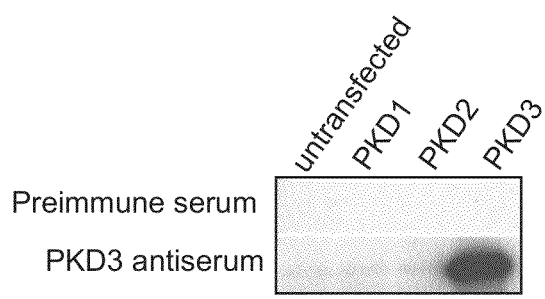

To identify the cell types and subcellular locations where PKDs are found, cortical cultures were analyzed with isoform-specific polyclonal antibodies against PKD1, PKD2, and PKD3 (FIGS. 9A and B). All three isoforms were present in MAP2-positive (FIG. 1C) and -negative cells, indicating expression in neurons and glia. In neurons, PKD2 and PKD3 were predominantly localized to the cell body. PKD2's distribution closely overlapped that of the cis-Golgi marker GM130 in all neurons examined, while PKD3 localized to the cis-Golgi in some neurons but in others was diffusely distributed throughout the soma (FIG. 1C), as in other cell types (Rey et al., 2003a; Rey et al., 2003b). The close association of these PKD isoforms with the Golgi is consistent with a role in protein trafficking.

Unlike the other two isoforms, PKD1 was present throughout the soma and dendrites in both diffuse and punctate distributions (FIGS. 1C and 1D). In dendrites, puncta were found in the shaft and some spines (FIG. 1D, inset), suggesting unsuspected roles for PKD1 in neuronal function and that PKD1 might regulate synaptic function.

FIGS. 1A-D. PKD1 Is Widely Expressed in Mouse Brain and Neurons. (A) reverse transcription-polymerase chain reaction (RT-PCR) showing expression of PKD1, 2, and 3 in hippocampus (Hip), cortex (Ctx), cerebellum (Cbl), and striatum (Str). (B) Western blot showing PKD1 expression in primary mouse cortical (Ctx) and hippocampal (Hip) neuronal cultures. (C) Immunocytochemical staining of PKD1, 2, and 3 in neuronal cell bodies. MAP2 serves as a neuronal marker, and GM130 labels cis-Golgi apparatus. Scale bar, 5 μm. (D) Immunocytochemical staining of a primary cortical neuron showing distribution of endogenous PKD1 in the cell body and dendrites. The neuron was infected with lentivirus encoding EGFP, which serves as a morphology marker. MAP2 specifically labels neuronal cell bodies and dendrites. Scale bars, 10 μm (main image) and 5 μm (inset).

FIGS. 9A and B. Generation of PKD1- and PKD3-Specific Polyclonal Antibodies. HEK cells were transfected with PKD1, 2, or 3, and lysates were used to test immunoreactivity of anti-sera. (A) αPKD1 was raised in rabbit against amino acids 203-261, 333-410, and 875-918 of murine PKD1. Preimmune serum (top) and anti-PKD1 antisera (middle) were used to blot against overexpressed PKD1, 2, and 3 from HEK cell lysate to confirm specificity. Anti-PKD1 antibody (Cell Signaling, 1:2000, bottom) served as a positive control. After confirmation of reactivity and specificity for PKD1, PKD1 antibody was affinity purified from rabbit antiserum. (B) αPKD3 was raised in rabbit against amino acids 1-80 of murine PKD3. Preimmune serum (top) and anti-PKD3 antisera (bottom) were used to blot against overexpressed PKD1, 2, and 3 from HEK cell lysate to confirm specificity. After confirmation of reactivity and specificity for PKD3, PKD3 antibody was affinity purified from rabbit antiserum.

PKD1 Activation is Downstream of mGluRs

Figure 10A:
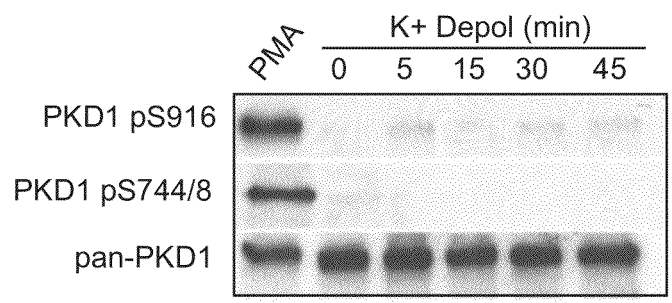
FIGS. 10A and 10B depict activation of PKD1 by Group I mGluRs, but not brain-derived neurotrophic factor (BDNF) or $K^+$ depolarization.

To investigate the potential role of PKD1 in synaptic function, it was asked if PKD1 is activated by the neurotransmitter glutamate. Mouse cortical cultures were stimulated with bath-applied glutamate (30 μM); and extracts for western blot analysis were prepared. After 10 min of stimulation, PKD1 was rapidly and robustly phosphorylated at the activation loop (S744/8) and autophosphorylation (S916) sites (FIG. 2A), indicating it was activated (Matthews et al., 1999b). Phosphorylation persisted for up to 60 min of stimulation. By contrast, activation of voltage-gated $Ca^{2+}$ channels with $K^+$ depolarization (Bradley et al., 2006) or TrkB receptors with brain-derived neurotophic factor (BDNF) did not activate PKD1 (FIG. 10A). Thus, PKD1 activity is rapidly but selectively controlled by synaptic stimuli.

In non-neuronal cells, PKD1 is commonly activated by Gαq-coupled receptors and isoforms of protein kinase C (PKC) or by an influx of extracellular $Ca^{2+}$ (Kunkel et al., 2007). Since glutamate activates Gαq-coupled metabotropic glutamate receptors (mGluRs) and $Ca^{2+}$-permeable N-methyl-D-aspartate receptors (NMDARs), it was determined whether either glutamate receptor subtype activates PKD1 in neurons. The mGluR antagonist MCPG reduced glutamate-induced PKD1 phosphorylation, and the mGluR-specific agonists ACPD (FIG. 2B, C) and (S)-3,5-dihydroxyphenylglycine (DHPG) (FIG. 10B) induced phosphorylation. The N-methyl-D-aspartate receptor (NMDAR) antagonist 2-amino-5-phosphonovaleric acid (APV) did not block phosphorylation of PKD1 by glutamate, and NMDA application did not stimulate autophosphorylation (FIG. 2B). Thus, metabotropic glutamate receptor (mGluR) activation seems to be necessary and sufficient to mediate PKD1 activation in response to glutamate, whereas NMDARs are dispensable.

PLC activation induces PKC to phosphorylate the activation loop of PKD1, although PKD1 may also autophosphorylate in trans independently of PKC or PLC (Rybin et al., 2009). However, inhibition of PLC or PKC blocked ACPD-induced PKD1 phosphorylation, indicating that mGluRs activate PKD1 through the canonical Gαq signaling pathway (FIG. 2C).

FIGS. 2A-C. PKD1 Kinase Activity Is Elicited by mGluRs. (A) Mouse cortical neurons were stimulated with 30 μM glutamate for the indicated times. (B) Neurons were stimulated as indicated, harvested, and examined by western blot (n=3). PMA was used as a positive control. (C) Left: activation pathway of PKD1. Drugs that inhibit each step of the pathway are listed under their targets. Right: Drugs were applied as shown. Each drug blocked ACPD-induced PKD1 phosphorylation.

Figure 10B:
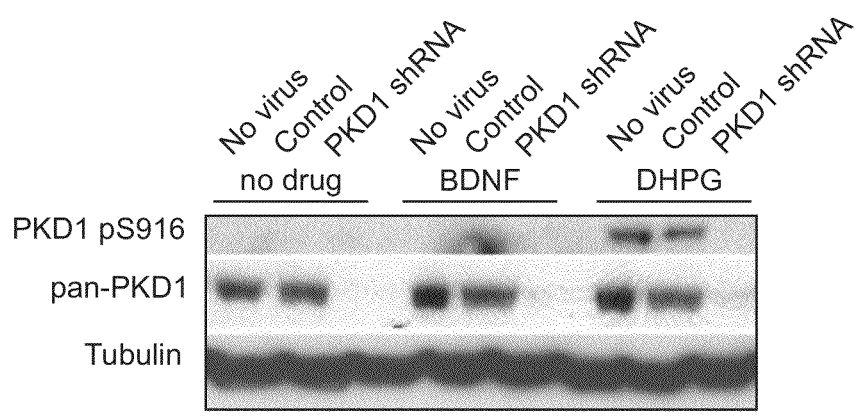

FIGS. 10A and 10B. Group I mGluRs, But Not BDNF or $K^+$ Depolarization, Activate PKD1. (A) Mouse cortical neurons were depolarized with $K^+$ (55 mM+50 μM D-APV) for the indicated times. The phorbol ester PMA (100 nM, 60 min) was used as a positive control for PKD1 activation. (B) Neurons were infected with lentivirus as indicated and stimulated with the Group I mGluR agonist DHPG (50 μM) or BDNF (100 ng/ml) for 60 min before lysis and analysis by western blot.

PKD1 Translocates in Response to $Ca^{2+}$ Influx Through NMDARs

Figure 3:
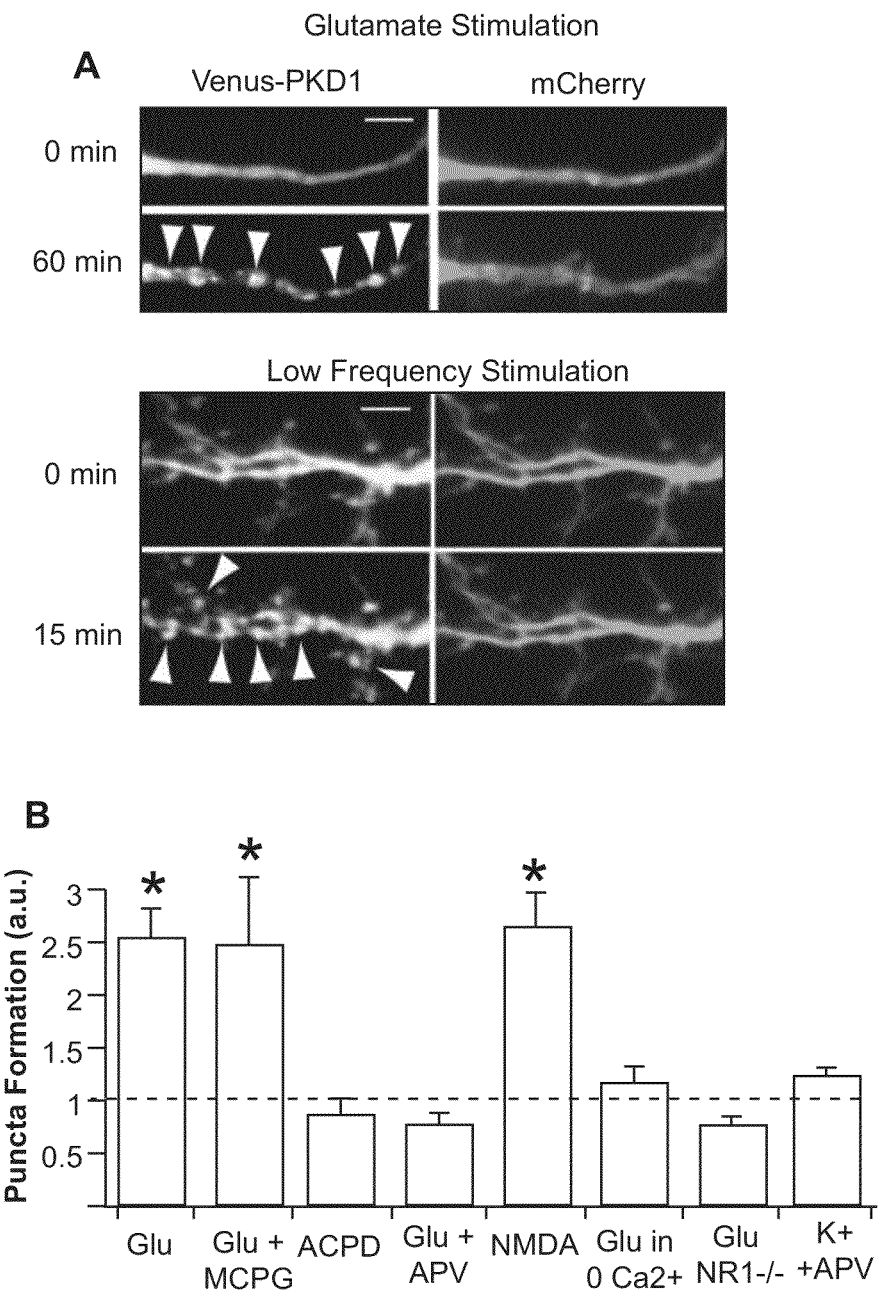
FIGS. 3A and B depict PKD1 translocation in response to N-methyl-D-aspartate receptors (NMDARs).

The subcellular localization of PKD1 after stimulation of non-neuronal cells has provided clues about its function. Certain stimuli cause PKD1 to move from the cytosol to the plasma membrane (Matthews et al., 2000; Rey et al., 2004), nucleus (Rozengurt et al., 2005), mitochondria (Hausser et al., 2005), and trans-Golgi network (TGN). The movement of PKD1 in neurons in response to glutamate was assessed. To facilitate the studies, a plasmid encoding PKD1 with the fluorescent protein Venus fused to its N-terminus (Venus-PKD1) was made. Transfected Venus-PKD1 was localized diffusely throughout the cytoplasm in neurons under basal conditions, but translocated to discrete puncta throughout the dendrites in response to glutamate (FIG. 3A). Co-transfected mCherry, a diffuse fluorescent protein, showed that neuronal morphology remained healthy and unchanged during puncta formation. PKD1 translocation to dendritic puncta was potently induced by more physiological synaptic stimulation with extracellular field electrodes (FIG. 3A). If these puncta are physiologically relevant, they might occasionally be elicited by spontaneous synaptic activity. Indeed, PKD1 spontaneously and reversibly formed intradendritic puncta.

The mechanisms of PKD1 translocation were examined. The receptor subtype responsible for glutamate-induced translocation of Venus-PKD1 was identified (FIG. 3B). To assess puncta formation under different conditions, a puncta index based on the standard deviation of pixel intensities throughout the image (Bradley et al., 2006) was developed. Puncta formation after glutamate stimulation was unaffected by the mGluR antagonist MCPG, and the mGluR agonist ACPD did not induce translocation, even at a dose (500 μM) well above that required for PKD1 activation (100 μM; FIG. 2B). In contrast, puncta formation was induced by NMDA alone and was blocked by the NMDAR antagonist APV or the absence of extracellular Ca$^{2+}$ (FIG. 3B). To further confirm the role of NMDARs in Venus-PKD1 puncta formation, neurons from NR1$^{-/-}$ embryos, which lack functional NMDARs (Bradley et al., 2006), were cultured. These neurons showed no Venus-PKD1 translocation after stimulation (FIG. 3B). To determine if the source of Ca$^{2+}$ influx is important, neurons were depolarized with high K$^+$ (55 mM) in the presence of APV, which should activate voltage-sensitive Ca$^{2+}$ channels (Bradley et al., 2006). No puncta formed (FIG. 3B). Thus, although mGluRs activate PKD1 after glutamatergic stimulation, the translocation of PKD1 to dendritic puncta is mediated by Ca$^{2+}$ influx through NMDARs.

FIGS. 3A and B. PKD1 Translocates in Response to NMDARs. (A) Images of Venus-PKD1 and mCherry before and after stimulation with 30 μM glutamate or with a field stimulator Hz). Scale bars, 10 μm. Images are representative (n>30 neurons, >3 experiments). (B) Puncta indices (PIs) for dendritic regions calculated for each stimulation. Y-axis is PI at 60 min divided by the same measure at 0 min. *p<0.05, before vs. after stimulation (two-tailed, paired t test).

PKD1 Translocation Requires PLC Activity

Experiments were conducted to better understand the signaling pathway by which NMDARs induce PKD1 translocation. In non-neuronal cells, PKD1 is redistributed after it binds through its N-terminal cysteine-rich domains to newly generated diacylglycerol (DAG) in plasma and intracellular membranes (Chen et al., 2008; Maeda et al., 2001; Oancea et al., 2003). To test whether NMDAR-dependent PKD1 translocation in neurons requires PLC-dependent DAG production, the PLC inhibitor U73122 was used; it was found that U73122 blocked glutamate-induced puncta formation (FIG. 4A). PKC antagonists GF 109203× or Gö6983 did not prevent PKD1 translocation, consistent with the finding that NMDARs do not induce PKD1 kinase activity.

It was then determined whether PKD1 translocation requires direct binding to DAG. Binding of DAG to the C1a and C1b domains of PKD1 is disrupted by two single amino acid substitutions, P155G and P287G, respectively (Baron and Malhotra, 2002; Maeda et al., 2001; Matthews et al., 1999a). In Venus-PKD, only the P287G mutation prevented glutamate-induced puncta formation (FIG. 4B). Thus, DAG produced downstream of NMDARs binds PKD1 and induces its translocation. Mutations of two other regulatory domains of PKD1, the pleckstrin homology domain and the PDZ ligand, did not affect translocation, emphasizing the specificity of the response to PLC. That a single mutation (P287G) disrupts translocation supports our conclusion that PKD1 translocation induced by NMDARs is a physiological response.

PKD1 Binds Plasma Membrane via C1b Domain Before Forming Puncta

The C1b domain of PKD1 mediates association with the plasma membrane (Matthews et al., 1999a), and the C1a domain mediates binding to internal membranes such as TGN (Baron and Malhotra, 2002; Maeda et al., 2001). Thus, the requirement of C1b for puncta formation was surprising and suggested another intermediate translocation step. In other cell types, PKD1 first translocates to the plasma membrane in response to PLC activation (Matthews et al., 2000; Rey et al., 2001). It was determined whether PKD1 associates with membranes before forming puncta. Confocal imaging revealed that puncta formation is a two-step process. After 10 min of stimulation, Venus-PKD1 localized to the plasma membrane in the cell body and dendrites in many neurons and was relatively absent from the cytoplasm (FIG. 4C). After 30 min, Venus-PKD1 formed puncta in the cytoplasm, which persisted with continued bath application of glutamate. In contrast, the P287G mutant did not translocate to the plasma membrane (FIG. 4C) and did not form puncta. Thus prior plasma membrane association is required for localization of PKD1 to puncta.

FIGS. 4A-C. PKD1 Translocation Is a Two-Step Process Requiring PLC. (A) Neurons transfected with Venus-PKD1 and mCherry were stimulated with glutamate (plus indicated drugs), and their puncta indices were calculated. Only U73122, the PLC inhibitor, blocks puncta formation. PKC inhibitors GF109203X, Gö6976, and Gö6983 had no effect. (B) (Top) Primary structure of PKD1 with critical amino acids highlighted. Bottom shows puncta indices of each construct in response to 30 μM glutamate. *p<0.05, before vs. after stimulation (two-tailed, paired t test). n>4 dendrites from at least three neurons in at least two experiments. (C) Neurons were stimulated, fixed, and imaged by confocal microscopy. Neurons transfected with Venus-PKD1 P287G do not show plasma membrane association after 10 min or puncta formation at 60 min. Scale bar, 5 μm.

PKD1 Colocalizes with Early Endosomes and AMPARs after Stimulation

Figure 5:
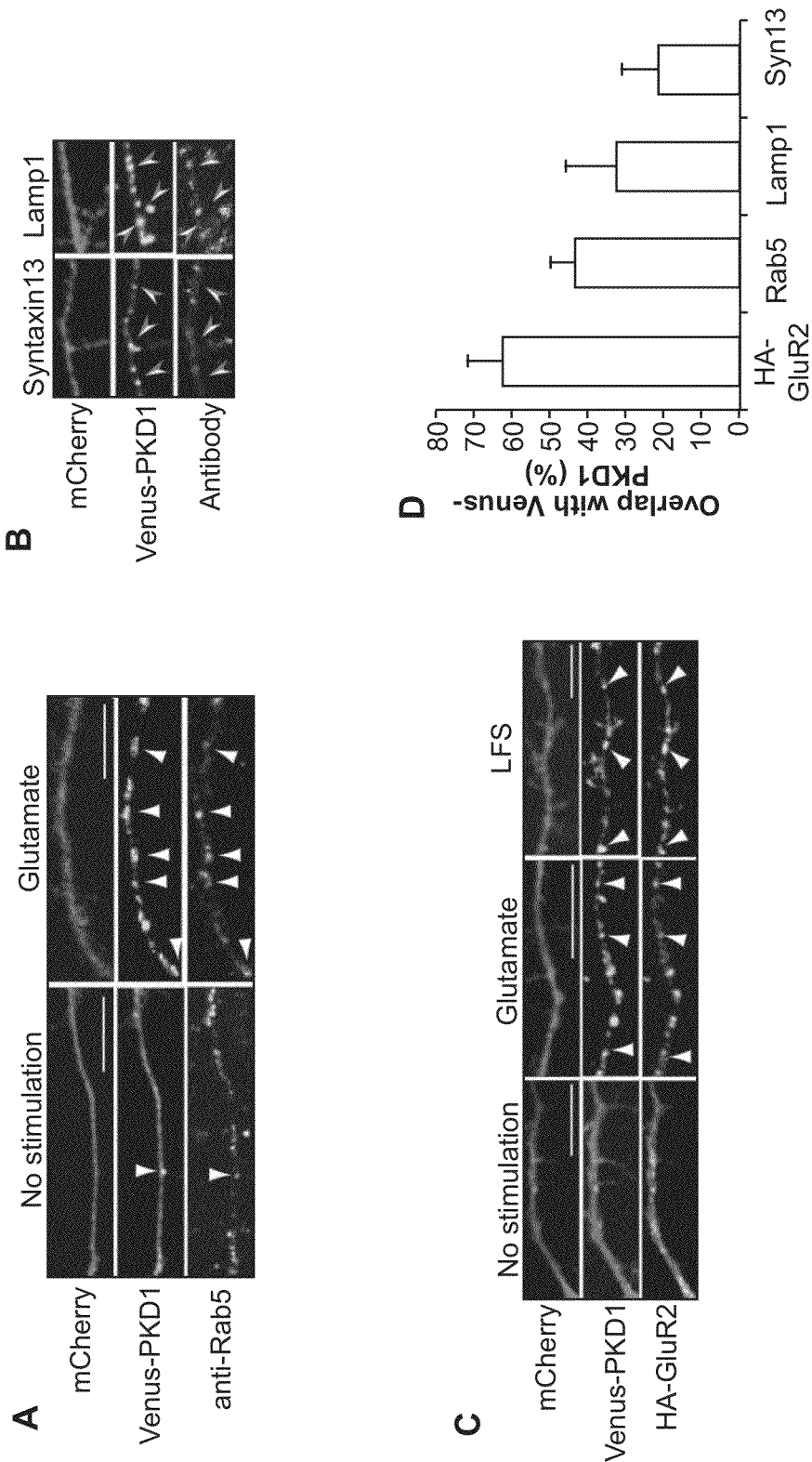
FIGS. 5A-H depict colocalization of PKD1 with endosomal markers and α-amino-3-hydroxy-5-methyl-4-isoxazolepropionic acid receptor (AMPARs).
Figure 5:
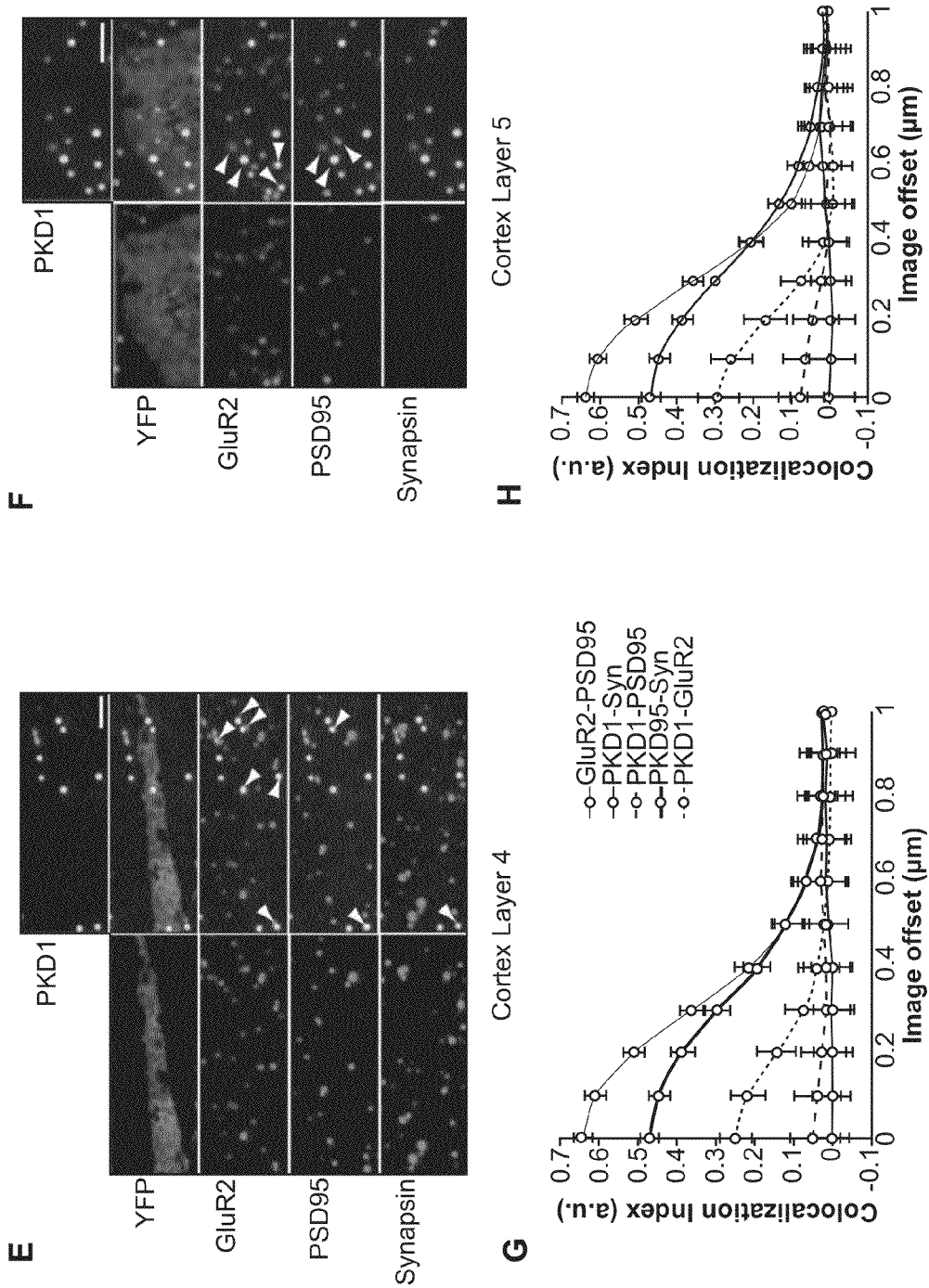

To characterize Venus-PKD1 puncta, colocalization of Venus-PKD1 and the TGN, where PKD1 has an established role, was tested. A CFP-tagged version of the TGN marker TGN38 (CFP-TGN38) (Sanchez-Ruiloba et al., 2006; Yeaman et al., 2004) showed some overlap with glutamate-induced Venus-PKD1 puncta. Since TGN38 is sometimes found in other dendritic endosomes (McNamara et al., 2004), antibodies against endogenous endosomal protein markers were used to test for glutamate-induced colocalization. Of the markers tested, Venus-PKD1 puncta colocalized best with Rab5 (FIG. 5A), a marker of early endosomes, and less well with syntaxin13, a recycling endosome marker, and Lamp1, a lysosomal marker (FIG. 5B). The dendritic colocalization of Venus PKD1 puncta was quantified with endosome makers in an overlap approach (Manders et al., 1992). Venus PKD1 had the highest overlap coefficient with Rab5 (mean, 43.3±6.3%) and the lowest with syntaxin13 (mean, 21.4±9.3%). These colocalization studies indicate that PKD1 localizes to the dendritic endosomal pathway, with some specificity for early endosomes.

The association of PKD1 with dendritic endosomes downstream of NMDARs suggested that PKD1 participates in activity-dependent trafficking of glutamate receptors. NMDAR activity leads to internalization of glutamate receptors, including AMPARs, which are either recycled or degraded in lysosomes (Lee et al., 2004; Lin et al., 2000). To see if PKD1-associated endosomes also contain AMPARs, Venus-PKD1 was coexpressed with HA-tagged GluR2, the most abundant AMPAR subunit in the cortex (Geiger et al., 1995; Jonas et al., 1994). Without stimulation, both proteins were distributed diffusely throughout the dendrites. Glutamate or field stimulation induced formation of puncta that contained Venus-PKD1 and HA-GluR2 (FIG. 5C). Of the molecules tested, Venus-PKD1 most strongly colocalized with HA-GluR2 (FIG. 5D, E).

These results raise the intriguing possibility that GluR2 might be a cargo whose trafficking is regulated by PKD1. However, these initial findings were obtained by overexpression in primary cultures, which can lead to formation of AMPARs that are not found endogenously and may not behave like native AMPARs (Shi et al., 2001). To investigate PKD1 localization in vivo, array tomography (Micheva and Smith, 2007) was used to obtain high-resolution immunofluorescence images. An array of 48 70-nm serial sections from a transgenic mouse expressing YFP in pyramidal cells of cortical layer 5 (Feng et al., 2000) was used. Thus, YFP served as a morphology marker for assessing PKD1's subcellular localization. PKD1 was distributed in a punctate manner throughout neurons of layers 4 and 5 of adult mouse cortex (FIG. 5E, F). These puncta were found in the cytosol and adjacent to the plasma membrane in the neuropil and cell bodies. As these tissue arrays can be stripped and probed multiple times (Micheva and Smith, 2007), the co-localization of PKD1 with a variety of synaptic markers could be tested in the same sample. To quantify this colocalization, a van Steensel-like correlation coefficient (van Steensel et al., 1996) was developed. Few PKD1 puncta were at synapses, as there was little co-localization with PSD95 or synapsin; however, PKD1 showed strong correlation with GluR2, suggesting that PKD1 is predominantly associated with an asynaptic fraction of GluR2 (FIGS. 5G and 5H). This is consistent with a role for PKD1 in trafficking GluR2 through the dendritic endosomal system in which the majority of PKD1 is associated with GluR2 in early endosomes.

FIGS. 5A-H. PKD1 Colocalizes with Endosomal Markers and AMPARs. (A) Neurons containing mCherry and Venus-PKD1 were stained with antibodies against Rab5. (Left) A spontaneous punctum (arrowhead). (Right) Overlapping puncta after glutamate stimulation (arrowheads). Images are representative (n>10 neurons, 3 experiments). (B) Neurons were stained with antibodies against syntaxin13 or Lamp1. Arrowheads show Venus puncta that do not colocalize with antibody immunofluorescence. Images are representative (n>10 neurons, 3 experiments). (C) Neurons were transfected with Venus-PKD1 and HA-tagged GluR2, stimulated with glutamate or a field stimulator, and stained with anti-HA antibodies. Arrowheads show colocalizing puncta. Images are representative (n>19 neurons, >3 experiments). Scale bars=10 μm. (D) Quantification of dendritic co-localization between Venus-PKD1 puncta and various markers. n>10 cells from at least three experiments per condition. Values are mean±SD. (E) Array tomography images of endogenous PKD1, GluR2, PSD-95, and synapsin in dendrites of cortical layer 4 of mouse brain transgenically expressing YFP as a morphology marker. Arrowheads point to colocalizing puncta. Scale bar=2 μm. (F) Array tomography images of endogenous PKD1, GluR2, PSD-95, and synapsin in the cell body layer, cortical layer 5 of mouse brain transgenically expressing YFP, which serves as a morphology marker. Arrowheads point to colocalizing puncta. Scale bar=2 μm. (G) Quantification of colocalization of PKD1 and synaptic markers in layer 4 of mouse cortex. Points along the line are mean correlation coefficients based on analysis of 48 70-nm sections; error bars show SD. (H) Extent of colocalization of PKD1 and synaptic markers in layer 5 of mouse cortex. Points along the line are mean correlation coefficients based on analysis of 48 70-nm sections; error bars show SD.

Interfering with PKD1 Function Disrupts GluR2 Trafficking

Figure 6:
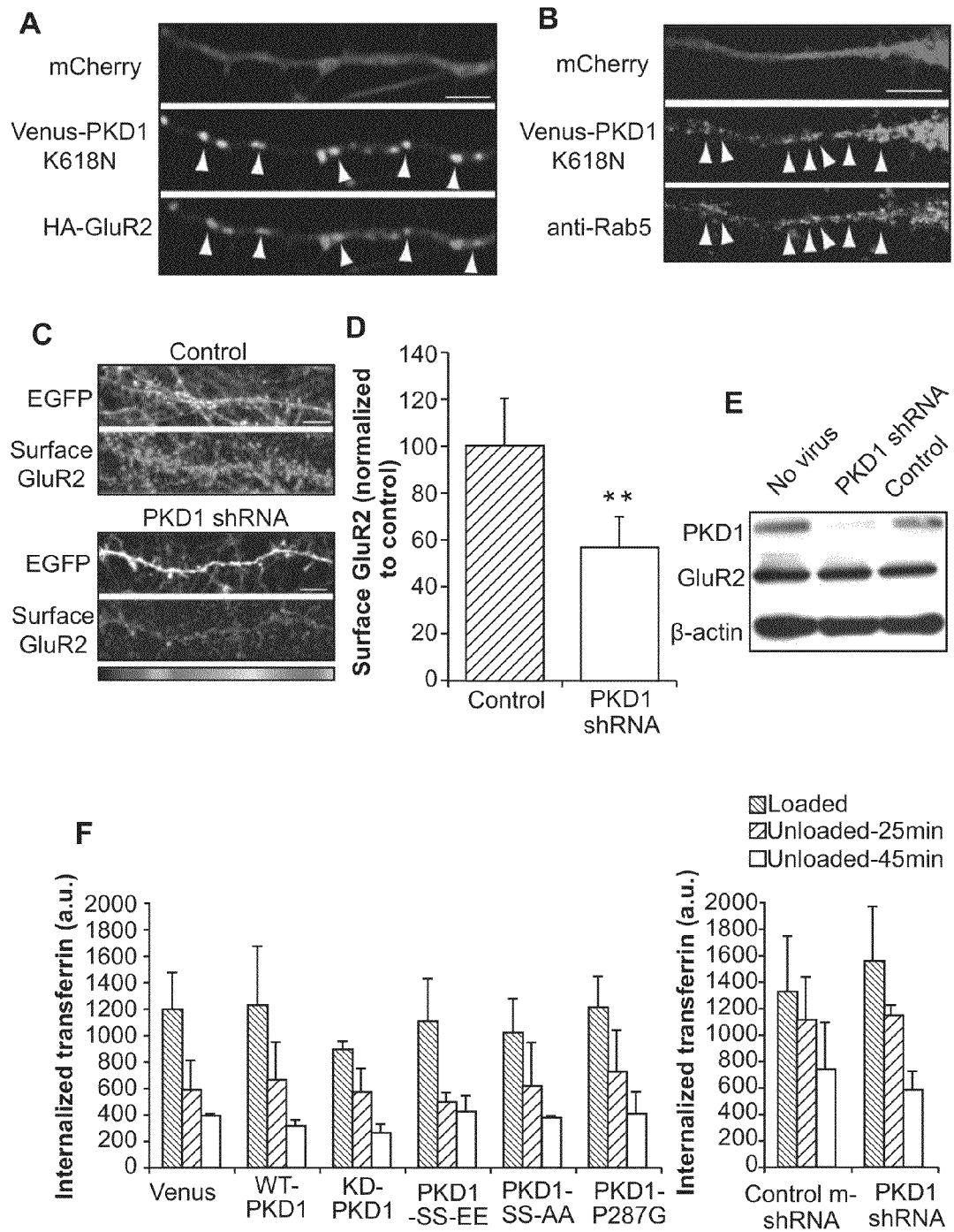
FIGS. 6A-F depict the effect of interfering with PKD1 on AMPAR trafficking.

The above-discussed co-localization studies in vivo and in vitro demonstrate that PKD1 associates with the AMPAR subunit GluR2 at endosomes. It was asked if PKD1 might be involved in dendritic AMPAR trafficking. To assess this possibility, Venus-PKD1 K618N, a catalytically inactive, dominant-interfering version of PKD1 that constitutively localizes to the TGN and TGN-derived vesicles (Sanchez-Ruiloba et al., 2006; Yeaman et al., 2004) was tested. Kinase-dead PKD1 prevents certain proteins from trafficking to the plasma membrane, trapping them in endosomes where PKD1 localizes (Sanchez-Ruiloba et al., 2006; Yeaman et al., 2004). In unstimulated neurons, Venus-PKD1 K618N altered the subcellular localization of coexpressed HA-GluR2: HA-GluR2 formed puncta that colocalized with Venus-PKD1 K618N (FIG. 6A). These puncta were Rab5 positive (FIG. 6B), indicating that kinase-dead PKD1 caused GluR2 to accumulate abnormally in endosomes.

To further establish the specificity and physiological relevance of this finding, it was investigated whether the effects on GluR2 trafficking resulted specifically from the inhibition of PKD1 function. It was determined whether knockdown of PKD1 led to a corresponding reduction in endogenous GluR2 subunits at the plasma membrane. At 7 DIV, neurons were infected with a lentivirus encoding EGFP and either a short hairpin RNA (shRNA) against PKD1 or a control mutated shRNA. Spiny proximal dendrites of pyramidal and stellate neurons were stained for surface GluR1 at 12-14 DIV. PKD1 knockdown reduced GluR2 levels to ~60% of that in control cells (FIGS. 6C and 6D). Total GluR2 protein levels were unaffected by the knockdown (FIG. 6E). Thus, PKD1 regulates the trafficking, rather than the expression, of GluR2.

To investigate whether the effect of PKD1 on AMPAR trafficking reflects a specific cargo relationship or a broader role in regulating protein cycling in dendrites, the effect of PKD1 on the uptake or recycling of fluorescently tagged transferrin (Park et al., 2004; Steiner et al., 2005) was assessed. shRNA knockdown of PKD1 or overexpression of interfering forms of PKD1 did not affect transferrin recycling (FIG. 6F). Since AMPAR trafficking can be dysregulated without affecting transferrin uptake or recycling (Steiner et al., 2005), these findings suggest PKD1 could regulate the recycling of one or more glutamate receptor subtypes without affecting global dendritic protein trafficking.

FIGS. 6A-F. Interfering with PKD1 Disrupts AMPAR Trafficking. (A) Neurons were transfected with Venus-PKD1 K618N and HA-GluR2 and stained with anti-HA antibody. Arrowheads show colocalizing puncta. Images are representative (n>9 neurons, 4 experiments). (B) Neurons transfected with Venus-PKD1 K618N were stained with antibodies against early endosomal marker Rab5. Arrowheads show colocalizing puncta. (C) Neurons were infected with lentivirus encoding GFP and a control shRNA or shRNA against PKD1. Surface staining for endogenous GluR2 is shown in lower panels; blue pixels indicate lower intensity stain than red pixels. Scale bar, 5 μm. (D) Quantification of surface GluR2 staining shown in (C). Values are mean±SD. n>80 dendrites, >15 cells per condition over 3 experiments. **p<0.001. (E) Total protein levels of PKD1 and GluR2 from neurons infected with virus encoding either shRNA against PKD1 or control mutated shRNA. n=3 experiments. (F) Fluorescently labeled transferrin was loaded into neurons transfected with mCherry and versions of PKD1. After reaching equilibrium, neurons were unloaded with an excess of unlabeled transferrin for 25 or 45 min and fixed. The amount of transferrin fluorescence remaining in the dendrites was compared across constructs. No significant differences were found among Venus-PKD1 constructs (left) or between shRNA and control constructs (right).

Figure 7:
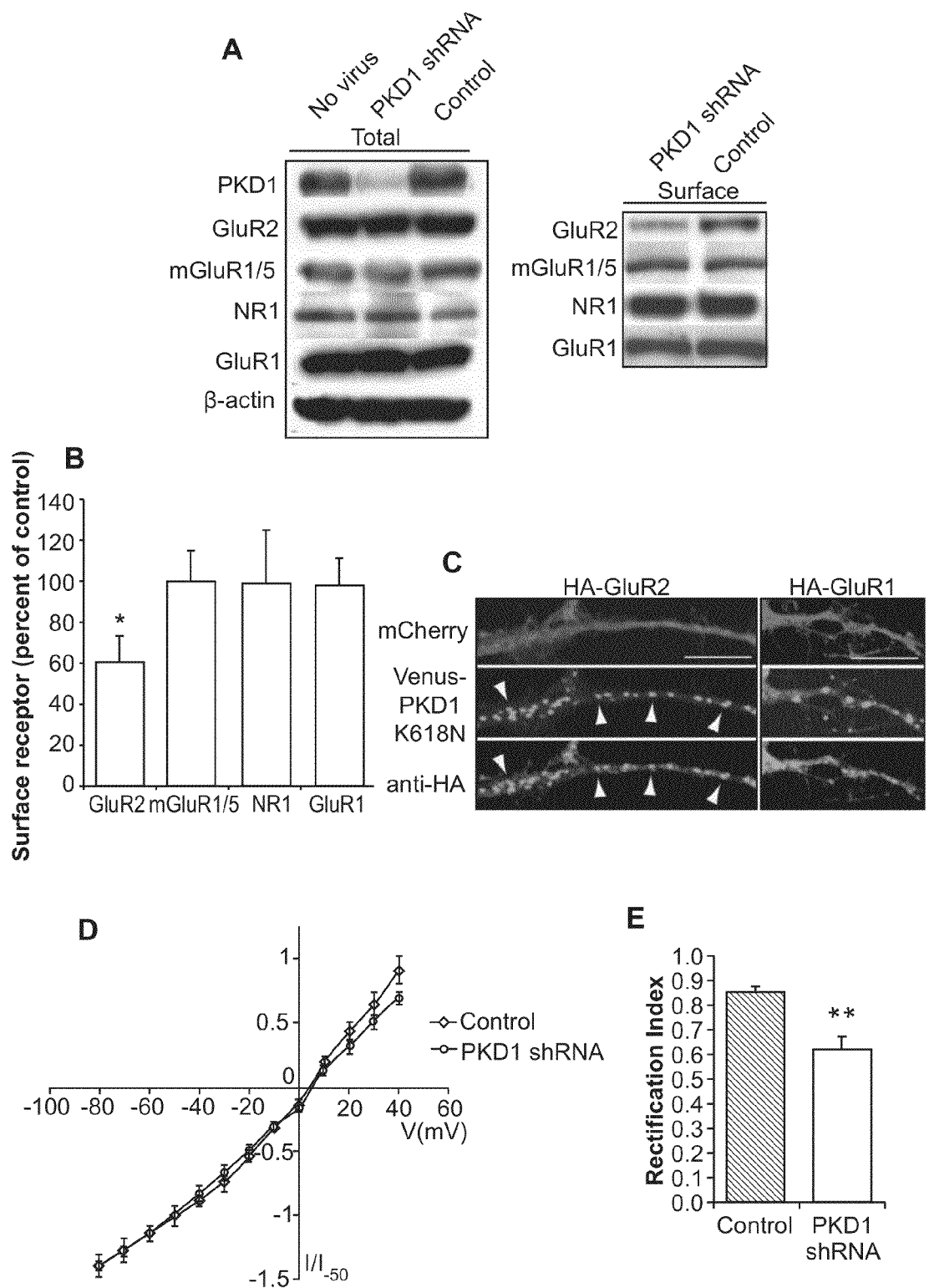
FIGS. 7A-E depict PKD1 regulation of glutamate receptor-2 (GluR2), and not glutamate receptor-1 (GluR1), surface expression.

PKD1 Regulates Surface Expression of GluR2 but Not GluR1 or Other Glutamate Receptors The question was asked whether PKD1 regulates the trafficking of the two other glutamate receptor types that regulate PKD1: NMDARs and Group I mGluRs. Surface biotinylation assays after PKD1 knockdown by lentiviral infection, as described above, showed decreased surface expression of GluR2, but not of the obligatory NMDAR subunit NR1 or mGluRs or of GluR1 (FIGS. 7A and 7B). To confirm the latter result, the effect of a dominant-interfering PKD1 on trafficking of exogenously expressed GluR1, which can form homomeric AMPARs (Shi et al., 2001), was tested Unlike exogenously expressed HA-GluR2, Venus-PKD1 K618N did not colocalize with HA-GluR1 or affect HA-GluR1 localization (FIG. 7C).

Interfering with PKD1 Affects the Composition of Functional AMPARs

If PKD1 regulates the surface expression of GluR2 but not GluR1 subunits, it might determine the subunit composition of mature AMPARs. GluR2 critically governs $Ca^{2+}$ permeability and other biophysical properties of AMPARs (Isaac et al., 2007). Whether a synapse contains GluR2 lacking AMPARs is thus an important determinant of mEPSC size and post-synaptic calcium signaling; it may determine a cell's ability to express certain types of AMPAR-dependent plasticity (Isaac et al., 2007; Liu and Zukin, 2007). GluR2-lacking AMPARs display inward rectification in the presence of a polyamine such as spermine (Bowie and Mayer, 1995; Geiger et al., 1995; Jonas et al., 1994). To test whether PKD1 knockdown increases the proportion of GluR2-lacking AMPARs at the plasma membrane, UV curves of cells expressing shRNA against PKD1 or mutated control were measured. Cells lacking PKD1 displayed marked inward rectification, indicating that disrupting PKD1 function alters AMPAR subunit composition and leads to a relative increase in functional AMPARs lacking GluR2 (FIGS. 7D and 7E).

FIGS. 7A-E. PKD1 Specifically Regulates GluR2, not GluR1, Surface Expression. (A) Surface biotinylation assay showing total protein and surface receptor levels after PKD1 knockdown. (B) Quantification of biotinylation assay in A Bars show mean±SD. n=3 experiments per receptor. *p<0.05 (unpaired t test). (C) Neurons were transfected with Venus-PKD1 K618N and HA-GluR2 (left) or HA-GluR1 (right) and stained with anti-HA antibodies. Arrowheads show colocalizing puncta. Images are representative (n>9 neurons, 4 experiments). (D) Representative UV curves from cells expressing shRNA against PKD1 or control mutant shRNA. (E) Rectification indices calculated by dividing peak current at +40 mV by that at −60 mV. n=4 per condition. *p=0.006 (unpaired t test).

Figure 8:
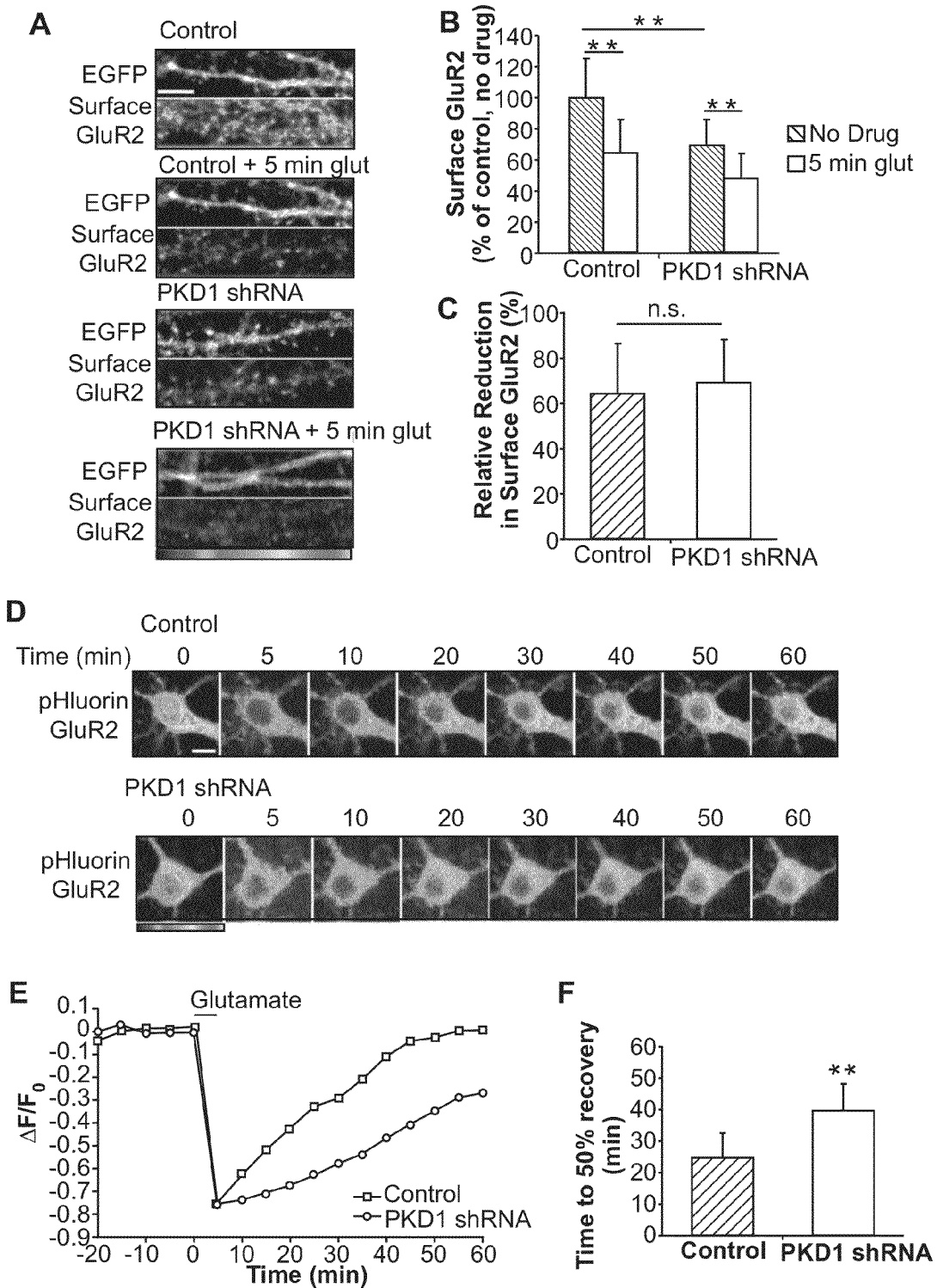
FIGS. 8A-F depict PKD1 regulation of GluR2 recycling after glutamate-induced endocytosis.

PKD1 Regulates Reinsertion, not Internalization, of GluR2 During Glutamate-Induced Recycling Since dominant-negative PKD1 and PKD1 knockdown led to intracellular retention of GluR2, it was hypothesized that PKD1 decreases the endocytosis of GluR2 or promotes its exocytosis. To test the former possibility, surface GluR2 levels after glutamate-induced endocytosis were measured (FIGS. 8A and 8B). If PKD1 normally decreases GluR2 endocytosis, it was expected that the relative decrease in surface GluR2 would be greater after PKD1 knockdown than in control neurons. However, no difference was found in surface GluR2 reduction after glutamate between control and PKD1 knockdown cells (FIG. 8C). Thus, PKD1 does not regulate GluR2 endocytosis in response to glutamate.

To test whether PKD1 promotes GluR2 exocytosis, live cells expressing a GluR2 construct with an N-terminal superecliptic pHluorin tag (pH-GluR2) were imaged. Using this system, surface GluR2 is measured by the intensity of pHluorin fluorescence, which is reversibly quenched by the acidic environment of endosomes (Miesenbock et al., 1998). After 5 minutes of glutamate application, pH-GluR2 fluorescence intensity was ~80% of baseline (FIGS. 8D and 8E). Immediately after glutamate stimulation, pH-GluR2 endocytosis is maximal, as indicated by a reduction of pH-GluR2 fluorescence intensity to 20% of baseline. The magnitude of peak endocytosis was similar in the presence of endogenous PKD1 or after PKD1 knockdown. Fifty-five minutes after glutamate stimulation, pH-GluR2 fluorescence recovered to >90% of baseline in neurons with endogenous PKD1. However, in neurons with PKD1 knocked down, fluorescence recovery was significantly delayed (FIG. 8F). PKD1 thus seems to be important in regulating the rate of GluR2 recycling in response to glutamatergic activity.

FIGS. 8A-F. PKD1 Regulates GluR2 Recycling After Glutamate-Induced Endocytosis. (A) Neurons were infected with lentivirus encoding GFP and a control shRNA or shRNA against PKD1. Surface staining for endogenous GluR2 is shown in lower panels; blue pixels indicate lower intensity staining than red pixels. Scale bar, 5 (B) Quantification of surface staining in B. Values are mean±SD. n=13-15 cells, >65 dendrites/condition. p<0.01 (unpaired t test with Bonferroni correction). (C) Comparison of relative reduction in surface GluR2 after glutamate application in control and PKD1 knockdown cells. p>0.1 (unpaired t test). (D) Representative images of neurons expressing pH-GluR2 and either PKD1 shRNA or mutated control. At t=0 min, glutamate was applied for 5 min and washed out. Blue pixels indicate lower-intensity pH-GluR2 signal than red pixels. Scale bar, 10 μm. (E) Quantification of pH-GluR2 intensity of images shown in D. (F) Quantification of recovery of pH-GluR2 fluorescence intensity halfway back to baseline. p<0.01 (unpaired t test). n=7 cells for control, 8 cells for PKD1 shRNA.

References

Abramoff M D, M. P., Ram S. J. (2004). Image processing with ImageJ. Biophotonics International 11, 36-42.

Adesnik, H., and Nicoll, R. A. (2007). Conservation of glutamate receptor 2-containing AMPA receptors during long-term potentiation. J Neurosci 27, 4598-4602.

Arrasate, M., and Finkbeiner, S. (2005). Automated microscope system for determining factors that predict neuronal fate. Proc Natl Acad Sci USA 102, 3840-3845.

Baron, C. L., and Malhotra, V. (2002). Role of diacylglycerol in PKD recruitment to the TGN and protein transport to the plasma membrane. Science 295, 325-328.

Bellone, C., and Luscher, C. (2005). mGluRs induce a long-term depression in the ventral tegmental area that involves a switch of the subunit composition of AMPA receptors. Eur J Neurosci 21, 1280-1288.

Bisbal, M., Conde, C., Donoso, M., Bollati, F., Sesma, J., Quiroga, S., Diaz And, A., Malhotra, V., Marzolo, M. P., and Caceres, A. (2008). Protein kinase d regulates trafficking of dendritic membrane proteins in developing neurons. J Neurosci 28, 9297-9308.

Bowie, D., and Mayer, M. L. (1995). Inward rectification of both AMPA and kainate subtype glutamate receptors generated by polyamine-mediated ion channel block. Neuron 15, 453-462.

Bradley, J., Carter, S. R., Rao, V. R., Wang, J., and Finkbeiner, S. (2006). Splice variants of the NR1 subunit differentially induce NMDA receptor-dependent gene expression. J Neurosci 26, 1065-1076.

Chen, J., Deng, F., Li, J., and Wang, Q. J. (2008). Selective binding of phorbol esters and diacylglycerol by individual C1 domains of the PKD family. Biochem J 411, 333-342.

Cingolani, L. A., Thalhammer, A., Yu, L. M., Catalano, M., Ramos, T., Colicos, M. A., and Goda, Y. (2008). Activity-dependent regulation of synaptic AMPA receptor composition and abundance by beta3 integrins. Neuron 58, 749-762.

Conrad, K. L., Tseng, K. Y., Uejima, J. L., Reimers, J. M., Heng, L. J., Shaham, Y., Marinelli, M., and Wolf, M. E.

(2008). Formation of accumbens GluR2-lacking AMPA receptors mediates incubation of cocaine craving. Nature 454, 118-121.

Cronshaw, J. M., Krutchinsky, A. N., Zhang, W., Chait, B. T., and Matunis, M. J. (2002). Proteomic analysis of the mammalian nuclear pore complex. J Cell Biol 158, 915-927.

Feng, G., Mellor, R. H., Bernstein, M., Keller-Peck, C., Nguyen, Q. T., Wallace, M., Nerbonne, J. M., Lichtman, J. W., and Sanes, J. R. (2000). Imaging neuronal subsets in transgenic mice expressing multiple spectral variants of GFP. Neuron 28, 41-51.

Gainey, M. A., Hurvitz-Wolff, J. R., Lambo, M. E., and Turrigiano, G. G. (2009). Synaptic scaling requires the GluR2 subunit of the AMPA receptor. J Neurosci 29, 6479-6489.

Geiger, J. R., Melcher, T., Koh, D. S., Sakmann, B., Seeburg, P. H., Jonas, P., and Monyer, H. (1995). Relative abundance of subunit mRNAs determines gating and Ca2+ permeability of AMPA receptors in principal neurons and interneurons in rat CNS. Neuron 15, 193-204.

Goel, A., Jiang, B., Xu, L. W., Song, L., Kirkwood, A., and Lee, H. K. (2006). Cross-modal regulation of synaptic AMPA receptors in primary sensory cortices by visual experience. Nat Neurosci 9, 1001-1003.

Gomez-Ospina, N., Tsuruta, F., Barreto-Chang, O., Hu, L., and Dolmetsch, R. (2006). The C terminus of the L-type voltage-gated calcium channel Ca(V)1.2 encodes a transcription factor. Cell 127, 591-606.

Guire, E. S., Oh, M. C., Soderling, T. R., and Derkach, V. A. (2008). Recruitment of calcium-permeable AMPA receptors during synaptic potentiation is regulated by CaM-kinase I. J Neurosci 28, 6000-6009.

Hausser, A., Storz, P., Martens, S., Link, G., Toker, A., and Pfizenmaier, K. (2005). Protein kinase D regulates vesicular transport by phosphorylating and activating phosphatidylinositol-4 kinase IIIbeta at the Golgi complex. Nat Cell Biol 7, 880-886.

Horton, A. C., and Ehlers, M. D. (2003). Dual modes of endoplasmic reticulum-to-Golgi transport in dendrites revealed by live-cell imaging. J Neurosci 23, 6188-6199.

Horton, A. C., Racz, B., Monson, E. E., Lin, A. L., Weinberg, R. J., and Ehlers, M. D. (2005). Polarized secretory trafficking directs cargo for asymmetric dendrite growth and morphogenesis. Neuron 48, 757-771.

Iglesias, T., Matthews, S., and Rozengurt, E. (1998). Dissimilar phorbol ester binding properties of the individual cysteine-rich motifs of protein kinase D. FEBS Lett 437, 19-23.

Isaac, J. T., Ashby, M., and McBain, C. J. (2007). The role of the GluR2 subunit in AMPA receptor function and synaptic plasticity. Neuron 54, 859-871.

Jonas, P., Racca, C., Sakmann, B., Seeburg, P. H., and Monyer, H. (1994). Differences in Ca2+ permeability of AMPA-type glutamate receptor channels in neocortical neurons caused by differential GluR-B subunit expression. Neuron 12, 1281-1289.

Kennedy, M. J., and Ehlers, M. D. (2006). Organelles and Trafficking Machinery for Postsynaptic Plasticity. Annu Rev Neurosci.

Kielland, A., Bochorishvili, G., Corson, J., Zhang, L., Rosin, D. L., Heggelund, P., and Zhu, J. J. (2009). Activity patterns govern synapse-specific AMPA receptor trafficking between deliverable and synaptic pools. Neuron 62, 84-101.

Kunkel, M. T., Toker, A., Tsien, R. Y., and Newton, A. C. (2007). Calcium-dependent regulation of protein kinase D revealed by a genetically encoded kinase activity reporter. J Biol Chem 282, 6733-6742.

Lee, S. H., Simonetta, A., and Sheng, M. (2004). Subunit rules governing the sorting of internalized AMPA receptors in hippocampal neurons. Neuron 43, 221-236.

Li, J., Chen, L. A., Townsend, C. M., Jr., and Evers, B. M. (2008). PKD1, PKD2, and their substrate Kidins220 regulate neurotensin secretion in the BON human endocrine cell line. J Biol Chem 283, 2614-2621.

Li, J., O'Connor, K. L., Hellmich, M. R., Greeley, G. H., Jr., Townsend, C. M., Jr., and Evers, B. M. (2004). The role of protein kinase D in neurotensin secretion mediated by protein kinase C-alpha/-delta and Rho/Rho kinase. J Biol Chem 279, 28466-28474.

Lin, J. W., Ju, W., Foster, K., Lee, S. H., Ahmadian, G., Wyszynski, M., Wang, Y. T., and Sheng, M. (2000). Distinct molecular mechanisms and divergent endocytotic pathways of AMPA receptor internalization. Nat Neurosci 3, 1282-1290.

Liu, S. J., and Cull-Candy, S. G. (2005). Subunit interaction with PICK and GRIP controls Ca2+ permeability of AMPARs at cerebellar synapses. Nat Neurosci 8, 768-775.

Liu, S. J., and Zukin, R. S. (2007). Ca2+-permeable AMPA receptors in synaptic plasticity and neuronal death. Trends Neurosci 30, 126-134.

Lu, W., and Ziff, E. B. (2005). PICK1 interacts with ABP/GRIP to regulate AMPA receptor trafficking. Neuron 47, 407-421.

Maeda, Y., Beznoussenko, G. V., Van Lint, J., Mironov, A. A., and Malhotra, V. (2001). Recruitment of protein kinase D to the trans-Golgi network via the first cysteine-rich domain. Embo J 20, 5982-5990.

Mameli, M., Balland, B., Lujan, R., and Luscher, C. (2007). Rapid synthesis and synaptic insertion of GluR2 for mGluR-LTD in the ventral tegmental area. Science 317, 530-533.

Manders, E. M., Stap, J., Brakenhoff, G. J., van Driel, R., and Aten, J. A. (1992). Dynamics of three-dimensional replication patterns during the S-phase, analysed by double labelling of DNA and confocal microscopy. J Cell Sci 103 (Pt 3), 857-862.

Matthews, S., Iglesias, T., Cantrell, D., and Rozengurt, E. (1999a). Dynamic re-distribution of protein kinase D (PKD) as revealed by a GFP-PKD fusion protein: dissociation from PKD activation. FEBS Lett 457, 515-521.

Matthews, S. A., Iglesias, T., Rozengurt, E., and Cantrell, D. (2000). Spatial and temporal regulation of protein kinase D (PKD). Embo J 19, 2935-2945.

Matthews, S. A., Rozengurt, E., and Cantrell, D. (1999b). Characterization of serine 916 as an in vivo autophosphorylation site for protein kinase D/Protein kinase Cmu. J Biol Chem 274, 26543-26549.

McNamara, J. O., Grigston, J. C., VanDongen, H. M. A., and VanDongen, A. M. J. (2004). Rapid dendritic transport of TGN38, a putative cargo receptor. Mol Brain Res 127, 68-78.

Medeiros, R. B., Dickey, D. M., Chung, H., Quale, A. C., Nagarajan, L. R., Billadeau, D. D., and Shimizu, Y. (2005). Protein kinase D1 and the beta 1 integrin cytoplasmic domain control beta 1 integrin function via regulation of Rap1 activation. Immunity 23, 213-226.

Merrill, M. A., Chen, Y., Strack, S., and Hell, J. W. (2005). Activity-driven postsynaptic translocation of CaMKII. Trends Pharmacol Sci 26, 645-653.

Micheva, K. D., and Smith, S. J. (2007). Array tomography: a new tool for imaging the molecular architecture and ultrastructure of neural circuits. Neuron 55, 25-36.

Miesenbock, G., De Angelis, D. A., and Rothman, J. E. (1998). Visualizing secretion and synaptic transmission with pH-sensitive green fluorescent proteins. Nature 394, 192-195.

Oancea, E., Bezzerides, V. J., Greka, A., and Clapham, D. E. (2003). Mechanism of persistent protein kinase D1 translocation and activation. Dev Cell 4, 561-574.

Oancea, E., and Meyer, T. (1998). Protein kinase C as a molecular machine for decoding calcium and diacylglycerol signals. Cell 95, 307-318.

Oster, H., Abraham, D., and Leitges, M. (2006). Expression of the protein kinase D (PKD) family during mouse embryogenesis. Gene Expr Patterns 6, 400-408.

Park, M., Penick, E. C., Edwards, J. G., Kauer, J. A., and Ehlers, M. D. (2004). Recycling endosomes supply AMPA receptors for LTP. Science 305, 1972-1975.

Passafaro, M., Piech, V., and Sheng, M. (2001). Subunit-specific temporal and spatial patterns of AMPA receptor exocytosis in hippocampal neurons. Nat Neurosci 4, 917-926.

Plant, K., Pelkey, K. A., Bortolotto, Z. A., Morita, D., Terashima, A., McBain, C. J., Collingridge, G. L., and Isaac, J. T. (2006). Transient incorporation of native GluR2-lacking AMPA receptors during hippocampal long-term potentiation. Nat Neurosci 9, 602-604.

Rao, V. R., Pintchovski, S. A., Chin, J., Peebles, C. L., Mitra, S., and Finkbeiner, S. (2006). AMPA receptors regulate transcription of the plasticity-related immediate-early gene Arc. Nat. Neurosci 9, 887-895.

Rey, O., Reeve, J. R., Jr., Zhukova, E., Sinnett-Smith, J., and Rozengurt, E. (2004). G protein-coupled receptor-mediated phosphorylation of the activation loop of protein kinase D: dependence on plasma membrane translocation and protein kinase Cepsilon. J Biol Chem 279, 34361-34372.

Rey, O., Young, S. H., Cantrell, D., and Rozengurt, E. (2001). Rapid protein kinase D translocation in response to G protein-coupled receptor activation. Dependence on protein kinase C. J Biol Chem 276, 32616-32626.

Rey, O., Yuan, J., and Rozengurt, E. (2003a). Intracellular redistribution of protein kinase D2 in response to G-protein-coupled receptor agonists. Biochem Biophys Res Commun 302, 817-824.

Rey, O., Yuan, J., Young, S. H., and Rozengurt, E. (2003b). Protein kinase C nu/protein kinase D3 nuclear localization, catalytic activation, and intracellular redistribution in response to G protein-coupled receptor agonists. J Biol Chem 278, 23773-23785.

Rozengurt, E., Rey, O., and Waldron, R. T. (2005). Protein kinase D signaling. J Biol Chem 280, 13205-13208.

Rybin, V. O., Guo, J., and Steinberg, S. F. (2009). Protein kinase D1 autophosphorylation via distinct mechanisms at Ser744/Ser748 and Ser916. J Biol Chem 284, 2332-2343.

Sanchez-Ruiloba, L., Cabrera-Poch, N., Rodriguez-Martinez, M., Lopez-Menendez, C., Jean-Mairet, R. M., Higuero, A. M., and Iglesias, T. (2006). Protein kinase D intracellular localization and activity control kinase D-interacting substrate of 220-kDa traffic through a postsynaptic density-95/discs large/zonula occludens-1-binding motif. J Biol Chem 281, 18888-18900.

Shi, S., Hayashi, Y., Esteban, J. A., and Malinow, R. (2001). Subunit-specific rules governing AMPA receptor trafficking to synapses in hippocampal pyramidal neurons. Cell 105, 331-343.

Steiner, P., Alberi, S., Kulangara, K., Yersin, A., Sarria, J. C., Regulier, E., Kasas, S., Dietler, G., Muller, D., Catsicas, S., and Hirling, H. (2005). Interactions between NEEP21, GRIP1 and GluR2 regulate sorting and recycling of the glutamate receptor subunit GluR2. Embo J 24, 2873-2884.

Sumara, G., Formentini, I., Collins, S., Sumara, I., Windak, R., Bodenmiller, B., Ramracheya, R., Caille, D., Jiang, H., Platt, K. A., et al. (2009). Regulation of PKD by the MAPK p38delta in insulin secretion and glucose homeostasis. Cell 136, 235-248.

van Steensel, B., van Binnendijk, E. P., Hornsby, C. D., van der Voort, H. T., Krozowski, Z. S., de Kloet, E. R., and van Driel, R. (1996). Partial colocalization of glucocorticoid and mineralocorticoid receptors in discrete compartments in nuclei of rat hippocampus neurons. J Cell Sci 109 (Pt 4), 787-792.

Wang, Q. J. (2006). PKD at the crossroads of DAG and PKC signaling. Trends Pharmacol Sci 27, 317-323.

Wang, Y., Zheng, F., Zhou, X., Sun, Z., and Wang, H. (2009). Converging signal on ERK1/2 activity regulates group I mGluR-mediated Arc transcription. Neurosci Lett 460, 36-40.

Woods, A. J., White, D. P., Caswell, P. T., and Norman, J. C. (2004). PKD1/PKCmu promotes alphavbeta3 integrin recycling and delivery to nascent focal adhesions. Embo J 23, 2531-2543.

Yeaman, C., Ayala, M. I., Wright, J. R., Bard, F., Bossard, C., Ang, A., Maeda, Y., Seufferlein, T., Mellman, I., Nelson, W. J., and Malhotra, V. (2004). Protein kinase D regulates basolateral membrane protein exit from trans-Golgi network. Nat Cell Biol 6, 106-112.

Yin, D. M., Huang, Y. H., Zhu, Y. B., and Wang, Y. (2008). Both the establishment and maintenance of neuronal polarity require the activity of protein kinase D in the Golgi apparatus. J Neurosci 28, 8832-8843.

Example 2

Genetically Modified Mice Deficient in PKD1

Methods
Cell Culture

Cortices from E18 mouse embryos were dissected and treated with papain (10 units ml$^{-1}$, 30 min; Worthington Biochemical) followed by trypsin inhibitor (10 mg ml$^{-1}$, 15 min; Sigma). After trituration, dissociated neurons were plated on plastic tissue culture plates (3.4×10$^5$ cells per cm$^2$) or 12-mm glass coverslips (6.8×10$^5$ cells per cm$^2$) coated with poly-D-lysine (BD Biosciences). Neurons were grown in Neurobasal-A with B27 (Invitrogen). Neurons were used for experiments at 12 days in vitro (DIV), unless otherwise stated. HEK293T cells were maintained in Dulbecco's modified Eagle's medium (DMEM) with Glutamax, containing 10% heat-inactivated fetal bovine serum (Invitrogen), 100 U/mL penicillin, and 100 U/mL streptomycin at 37° C. and 5% CO$_2$.

Antibodies and Drugs

Phospho-PKD1 (Ser 744/748), phospho-PKD1 (Ser 916), and HDAC5 antibodies were purchased from Cell Signaling. Flag, α-tubulin, and β-actin antibodies were from Sigma. Secondary antibodies were from Jackson ImmunoResearch. DHPG, ACPD, MCPG, MPEP, CPCCOEt, AP5, NBQX, nimodipine were from Tocris. TTX was from Calbiochem. All other chemicals were from Sigma.

Western Blots

Cells were collected in ice-cold RIPA buffer (150 mM NaCl, 50 mM Tris buffer, pH 7.5, 1 mM EDTA, 1% NP-40, 0.5% deoxycholate and 0.1% SDS) containing protease inhibitors (Roche). Protein concentrations were determined by BCA assay. Equal quantities of total protein were separated by 10% SDS-PAGE and transferred to nitrocellulose (Amersham Biosciences). Membranes were blocked with 5% nonfat milk (Bio-Rad), probed with primary antibodies and peroxidase-conjugated secondary antibodies, and visualized using enhanced chemiluminescence reagents (Perkin Elmer). Blots were stripped in buffer (100 mM 2-mercaptoethanol, 2% SDS and 62.5 mM Tris, pH 6.7) for 50 min at 55° C.

Immunocytochemistry

Cells were fixed in 4% paraformaldehyde with 4% sucrose for 10 min and blocked in PBS with 3% bovine serum albumin, 2% goat or donkey serum, and 0.1% Triton-X100. Nuclei were stained with Hoechst 33342 (2.5 g ml-1, 10 min; Tocris).

Reporter Gene Assays

Cortical neurons (10 DIV) were cotransfected with one of the reporter genes and pRL0-Renilla (1:1 molar ratio). At 20-24 h after transfection, neurons were stimulated with drugs, and lysates were collected and assayed with a Dual Luciferase Kit (Promega) and a luminometer (Thermo Electron).

Reverse Transcription PCR

Total RNA was extracted from mouse brain using Qiagen RNEasy (Qiagen, Valencia, Calif.) kit according to manufacturer's instructions. cDNA was generated using SuperScript II reverse transcriptase according to manufacturer's instructions. PKDs 1, 2, and 3 were amplified with isoform specific primers as described (1).

qfRT-PCR

Cells were stimulated with drugs for 6 h and mRNA levels were determined by qfRT-PCR using gene-specific primers: 5'-cctgagccacctggaagagta-3' (SEQ ID NO:25) and 5'-ggc-ccattcatgtggttctg-3' (SEQ ID NO:26) for Arc, 5'-ctgtgacct-caagccagaaa-3'(SEQ ID NO:27) and 5'-gtacccaccactgac-ctcct-3' (SEQ ID NO:28) for PKD1, 5'-catcgacctcatcaacaacc-3' (SEQ ID NO:29) and 5'-tggctgagagacttgtccac-3' (SEQ ID NO:30) for PKD2, 5'-cccagaaatctgtgttccct-3' (SEQ ID NO:31) and 5'-agagagccgagctgagagtc-3' (SEQ ID NO:32) for PKD3, 5'-ccccaatgtgtccgtcgt-3' (SEQ ID NO:33) and 5'-gc-ctgcttcaccaccttct-3' (SEQ ID NO:34) for GAPDH (internal control gene for normalization). For detection of nascent Arc transcripts, primer pairs were as follows: intron 1 (primers anneal within intron 1), 5'-ccctgcaccgtgtatcttagagtg-3' (SEQ ID NO:35) and 5'-tccacccttgcaactaatttg-3' (SEQ ID NO:36); intron 2 (primers flank an intron-exon boundary), 5'-taacctg-gtgtccctcctggatc-3' (SEQ ID NO:37) and 5'-gcaaagacttctcag-cagccttga-3' (SEQ ID NO:38).

Mice

All animal procedures were approved by the University of California, San Francisco Institutional Animal Care and Use Committee. The genetically modified mice used in the study, PKD1 fl/fl (2), Nestin::Cre (3), and CaMKII::Cre (4) have been described previously.

Tissue Preparation and Staining

Mice were perfused with 4% paraformaldehyde (w/v). The brains were postfixed overnight at 4° C. For frozen sections, brains were cryoprotected in 30% sucrose, embedded in Tissue-Tek Optimal Cutting Temperature compound (Sakura) and cut into 12-mm sections. For polyethylene glycol (PEG) sections, brains were dehydrated in an ethanol series, embedded in a 2:1 mixture of PEG 1,000 and PEG 1,500, and cut into 10-mm sections. For immunostaining, sections were incubated with primary antibodies overnight at 4° C., followed by incubation with secondary antibodies at 20-23.5° C. for 2 h.

Electrophysiological Recordings

Field EPSPs (fEPSPs) were recorded with glass electrodes (3 M tip resistance) filled with 1 M NaCl and 25 mM HEPES, pH 7.3, and evoked every 20 s with a bipolar tungsten electrode (FHC). Recordings were filtered at 2 kHz (−3 dB, eight-pole Bessel), digitally sampled at 20 kHz with a Multiclamp 700A amplifier (Molecular Devices), and acquired with a Digidata-1322A digitizer and pClamp 9.2 software. Data were analyzed offline with pClamp9 software and OriginPro 8.0 (OriginLab). For recordings performed in CA1, the stimulating electrode was placed in the stratum radiatum at the border of CA3 and CA1, and the recording electrode was placed 150 µm away in CA1 stratum radiatum. Measures of synaptic strength and plasticity assessed in each slice consisted of input-output (I-O) relationships, paired-pulse ratios, LTP and LTD. Synaptic transmission strength was assessed by generating I-O curves for fEPSPs; input was the peak amplitude of the fiber volley, and the output was the initial slope of the fEPSP. Paired-pulse ratios were determined by evoking two fEPSPs 50 ms apart and dividing the initial slope of the second fEPSP by the initial slope of the first fEPSP ($fEPSP_2/fEPSP_1$). After a 15 min stable baseline was established, LTP was induced in CA1 by high-frequency stimulation (four 100-Hz trains of 100 stimuli). After a 15-min stable baseline was established, NMDA-LTD was induced by 3 min of 5 Hz stimulus train and mGluR-LTD was induced by bath application of 50 µM DHPG for 5 min.

Behavioral Tests

Only male mice were analyzed to reduce variability in behavioral performance. One cohort of mice was behaviorally evaluated at 3 months of age. Each cohort contained two groups: PKD1 null mice and littermate control mice.

Open Field

For the open field test, individual mice were placed in 41×41×30 cm acrylic animal cages for 15 min during which their horizontal and vertical movements were monitored by two arrays of 16 infrared light beam sensors (Flex-Field/Open Field Photobeam Activity System (PAS), San Diego Instruments, San Diego, Calif.) connected to a computer that recorded their position every millisecond. PAS software was then used to calculate, in both the horizontal plane and along the vertical axis, the total number of movements, the distance traveled, the time spent moving, and the total number of infrared beam breaks for each mouse. The apparatus was cleaned with 70% alcohol after testing of each mouse.

Elevated Plus Maze

The elevated plus maze consisted of two open (without walls) and two enclosed (with walls) arms elevated 63 cm above the ground (Hamilton-Kinder). Mice were allowed to habituate in the testing room under dim light for 1 h before testing. During testing, mice were placed at the junction between the open and closed arms of the plus maze and allowed to explore for 5 min. The maze was cleaned with 70% alcohol after testing of each mouse. Total distance traveled and time spent in both the open and closed arms were calculated based on infrared photobeam breaks.

Novel Object Recognition

Male mice from each genotype were habituated in a round testing arena (30 cm×30 cm) for 30 min on day one. On day two the mice were presented with two objects (familiar) within specific areas and mice were allowed to freely explore the arena and objects for 10 min then returned to their home cages. Four hour later, one of the objects was replaced with a new object (the novel object) and the mice were allowed to explore the environment for 10 min. Positions of the familiar and novel objects in the chamber were changed semi-randomly between testing of different mice but were kept constant between training and test sessions for any given mouse. Behavior was recorded with a video tracking system (Noldus). Frequency of interactions with the objects and time spent exploring each object were recorded for subsequent data analysis, and recognition memory was assessed in the final trial. Arenas and objects were cleaned with 70% ethanol after testing of each mouse.

Morris Water Maze

The water maze consisted of a pool (122 cm diameter) filled with water (21±1° C.) made opaque with nontoxic white tempera paint powder. The pool was located in a room surrounded by distinct extramaze (spatial) cues. Preceding hidden platform training, mice were given two pretraining trials in which they had to swim in a rectangular channel (15×122 cm) and mount a platform hidden 1.5 cm below the water surface in the middle of the channel. Mice that did not mount the platform within 90 s were gently guided to it and allowed to sit on it for 10 s before they were removed by the experimenter. The day after pretraining, mice were trained in the circular water maze. For hidden platform training, the platform (14×14 cm) was submerged 1.5 cm below the water surface. The platform location remained the same throughout hidden platform training, but the drop location varied semi-randomly between trials. Mice received two training sessions with 3 h intersession intervals for 5 consecutive days. Each session consisted of two trials with 10 min intertrial intervals. Mice that did not find the platform within 60 s were guided to it and allowed to sit on it for 10 s. In spatial probe trials, the platform was removed, and mice were allowed to swim for 60 s before they were removed. The drop location was 180° from where the platform was placed during hidden platform training. The same drop location was used for all spatial probe trials. After the final probe trial, mice were allowed to rest for 1 d, followed by cued platform training. In this task, the platform was marked with a visible cue (15 cm tall, black and white striped pole placed on top of the platform). Mice received two training sessions per day with 2-3 h intertrial intervals. Each session consisted of two training trials with 20 min intertrial intervals. For each session, the platform was moved to a new location, and the drop location varied semi-randomly between trials. Trials were aborted after 60 s. Behavior was recorded with a video tracking system (Noldus). Escape latencies, distance traveled, swim paths, swim speeds, percentage time spent in each quadrant, and platform crossings were recorded for subsequent analysis.

Statistical Analysis

One-way ANOVA and post-hoc Tukey t-tests were performed with Prism (GraphPad Software).

Results

Figure 13:
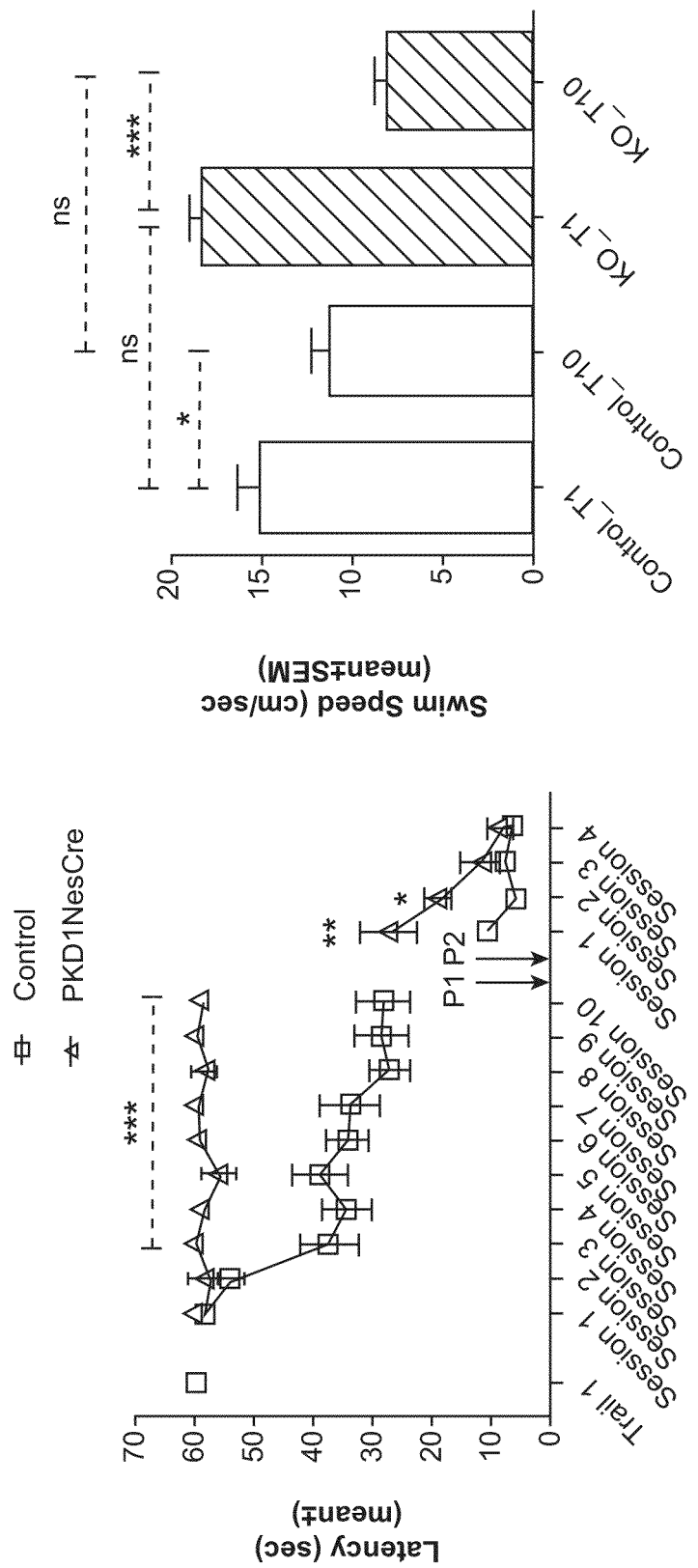
FIG. 13 depicts water maze deficits in PKD1 null mice.
Figure 14:
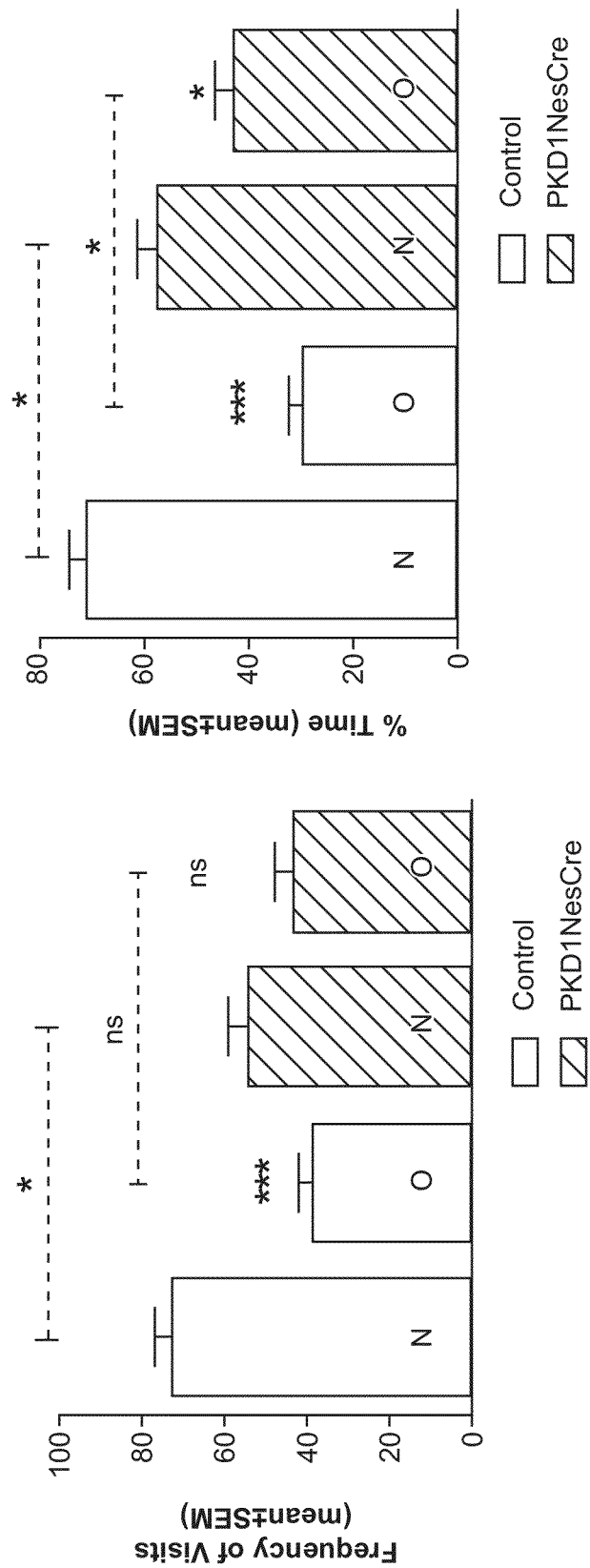
FIG. 14 depicts object recognition by PKD1 null mice.
Figure 15:
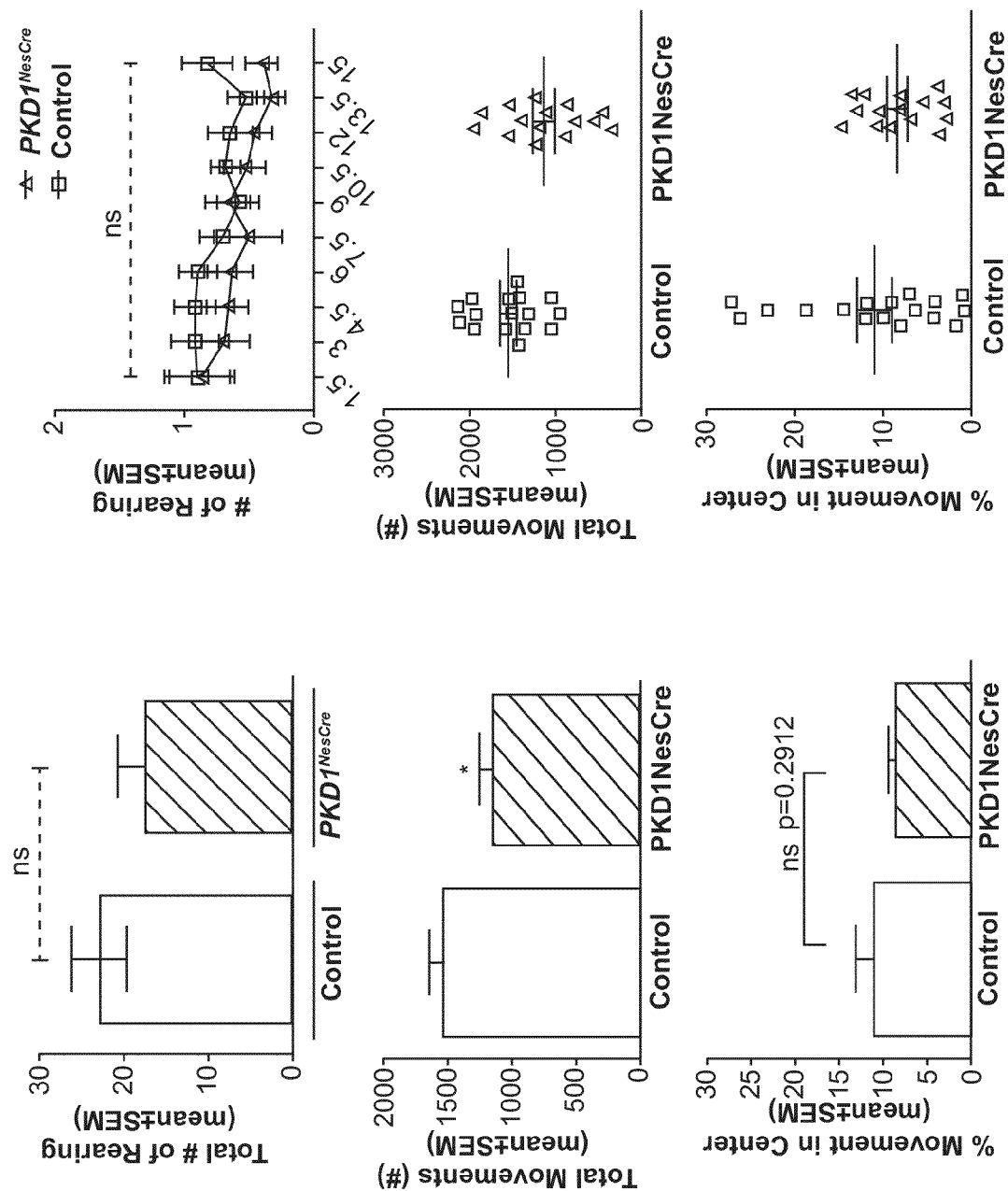
FIG. 15 depicts the results of open field testing of PKD1 null mice.
Figure 16:
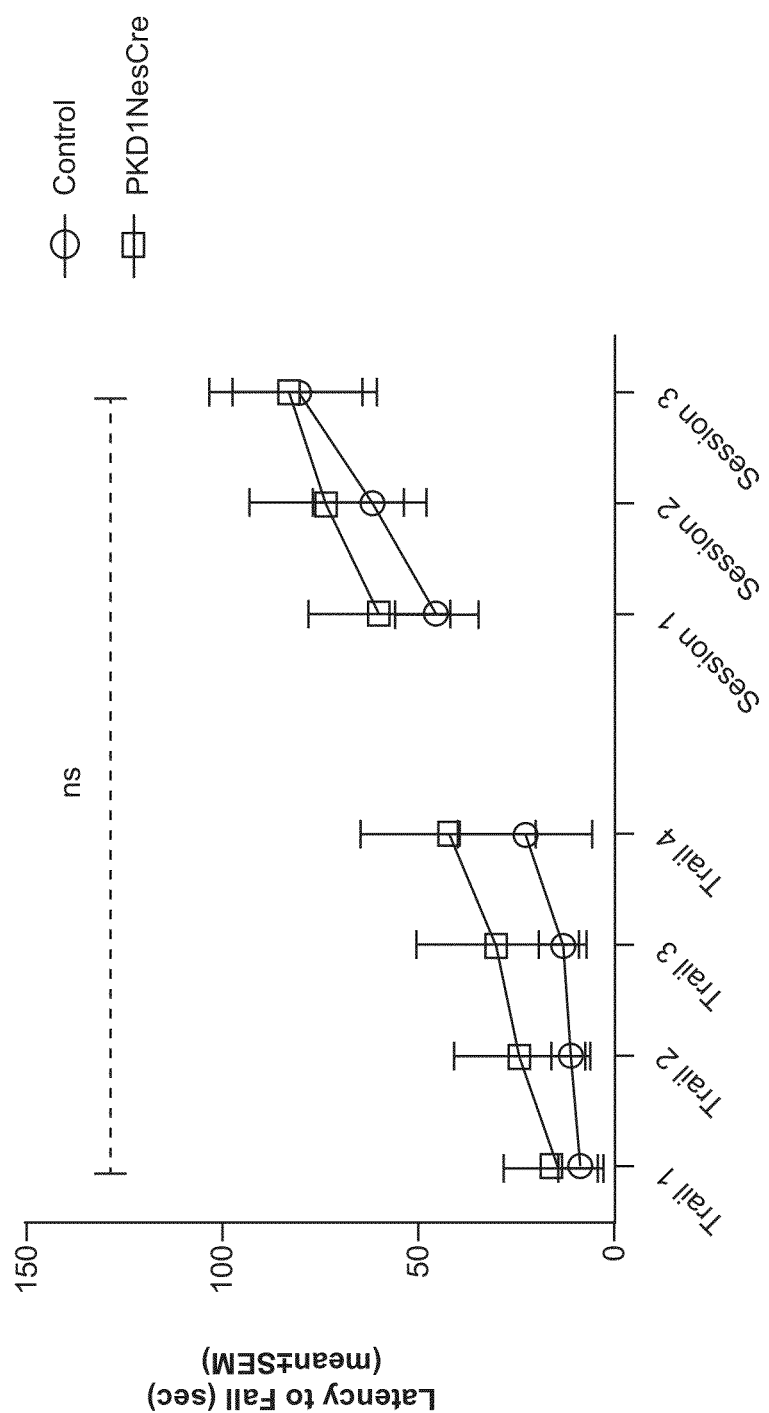
FIG. 16 depicts rotarod performance of PKD1 null mice.
Figure 17:
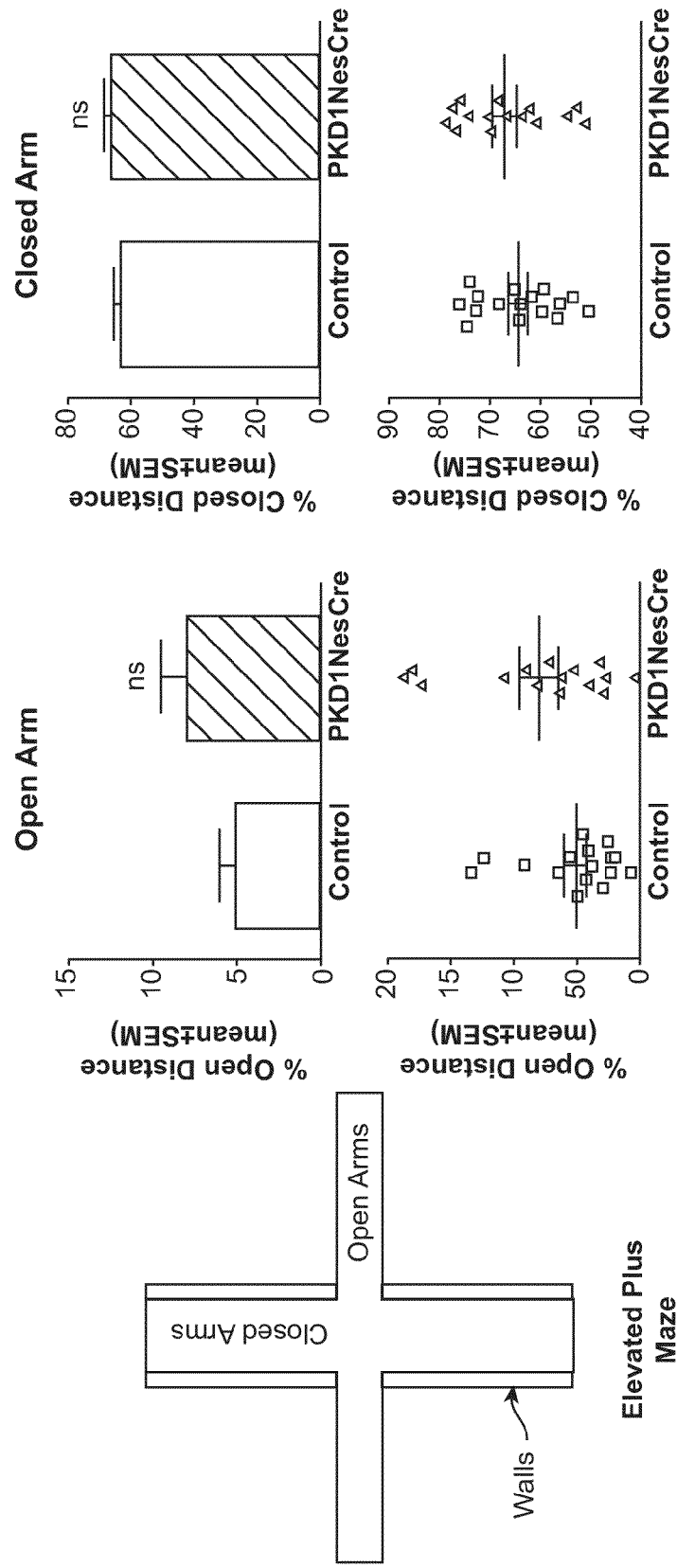
FIG. 17 depicts the results of anxiety testing of PKD1 null mice.
Figure 18:
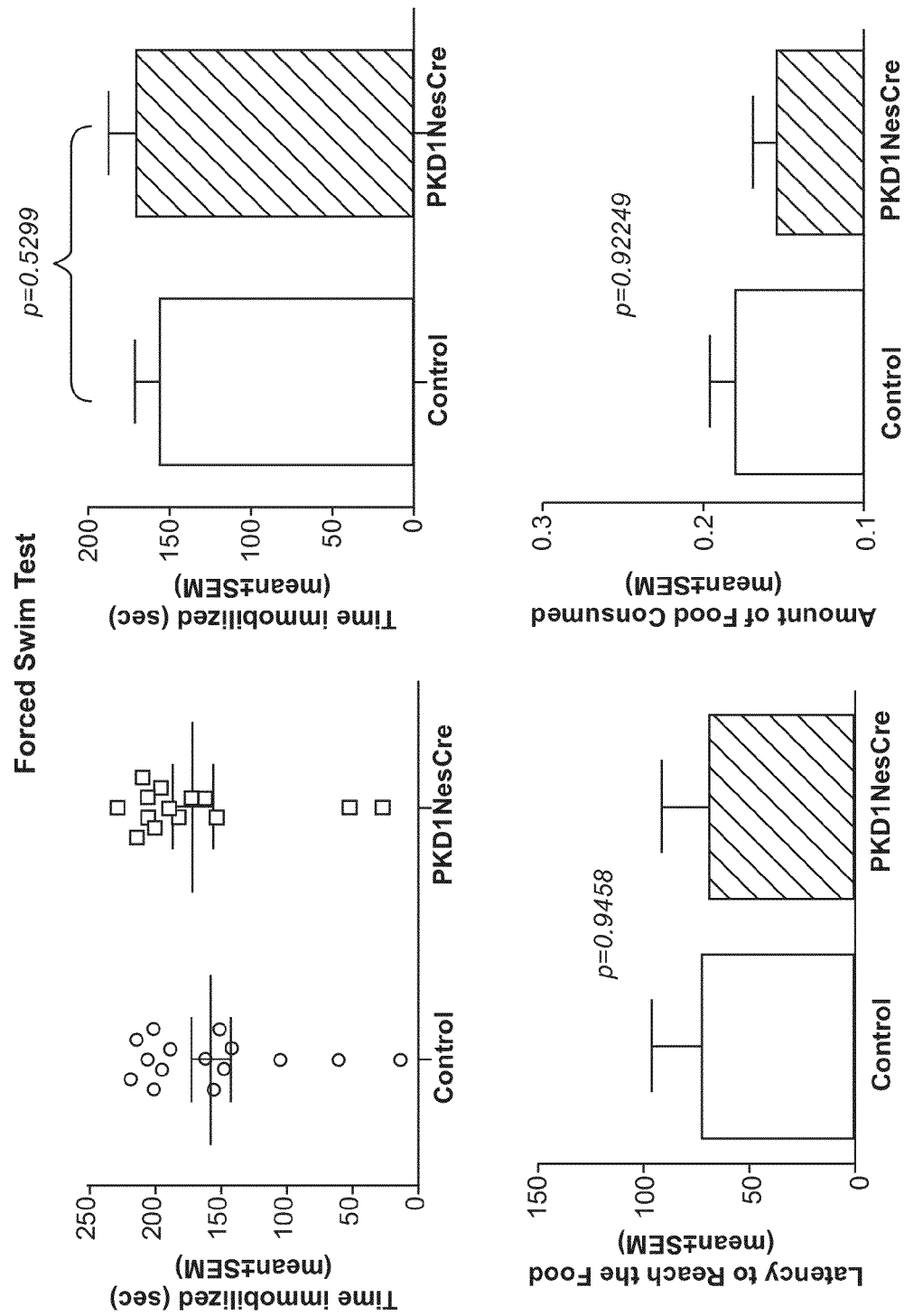
FIG. 18 depicts the results of depression testing of PKD1 null mice.

The results are shown in FIGS. 13-18. A series of behavioral tests were performed on mice with PKD1 deleted selectively from the CNS (PKD1$^{Nes/Cre}$: PKD1$^{flox/flox}$×Nestin$^{Cre/Cre}$). These mice displayed severe hippocampus-dependent spatial learning deficits as shown by the failure of the mice to learn the location of the hidden platform in the Morris Water Maze test, despite normal swimming speeds (FIG. 13). These mice found the visible platform quickly, indicating that their vision, sensory perception, and motivation are normal (FIG. 13). These mice also exhibited modest cortex-dependent novel object recognition deficits (FIG. 14). In open field testing, PKD1$^{Nes/Cre}$ mice showed a small but statistically significant difference from control mice in total movements although the total number of rearings and the amount of movement in the center of the open field was not significantly different from control animals (FIG. 15). Other behavioral tests were normal including the rotarod test of motor function (FIG. 16), the elevated plus maze test for anxiety (FIG. 17), and two tests for depression (FIG. 18). Taken together, these results suggest a critical and fairly selective role for PKD1 in hippocampus-dependent and cortex-dependent learning.

REFERENCES

Oster, H., Abraham, D., and Leitges, M. (2006). Expression of the protein kinase D (PKD) family during mouse embryogenesis. Gene Expr Patterns 6, 400-408.

Fielitz J, Kim M S, Shelton J M, Qi X, Hill J A, Richardson J A, Bassel-Duby R, Olson E N. [2008]. Requirement of protein kinase D1 for pathological cardiac remodeling. Proc Natl Acad Sci USA. 105(8), 3059-63.

F. Tronche, C. Kellendonk, O. Kretz, P. Gass, K. Anlag, P. C. Orban, R. Bock, R. Klein and G. Schütz. [1999]. Disruption of the glucocorticoid receptor gene in the nervous system results in reduced anxiety, Nat. Genet. 23, 99-103

Xu B, Gottschalk W, Chow A, Wilson R I, Schnell E, Zang K, Wang D, Nicoll R A, Lu B, Reichardt L F. [2000]. The role of brain-derived neurotrophic factor receptors in the mature hippocampus: modulation of long-term potentiation through a presynaptic mechanism involving TrkB. J. Neurosci. 20(18), 6888-97.

Example 3

PKD1 Modulator Effect on Non-Human Animal Model of Neurological Disorder

The effect of a PKD1 modulator (e.g., a PKD1 inhibitor) on a neurological disorder can be determined using a non-human animal model of the disorder.

Suitable non-human animal models of Parkinson's disease (PD) include, e.g., the α-synuclein transgenic mouse model; and the 1-methyl-4-phenyl-1,2,3,6,-tetrahydropyridine (MPTP) mouse model of Parkinson's disease. See, e.g., Betarbet et al. (2002) *Bioessays* 24:308; Orth and Tabrizi (2003) *Mov. Disord.* 18:729; Beal (2001) *Nat. Rev. Neurosci.* 2:325.

Suitable non-human animal models of Huntington's disease include, e.g., a transgenic mouse comprising a human huntingtin transgene (e.g., the R6 line, the YAC line), where the human huntingtin transgene comprises 30-150 CAG repeats (encoding a polyglutamine expansion); a knock-in mouse model, comprising a homozygous or heterozygous replacement of endogenous mouse huntingtin gene with a human huntingtin gene comprising 30-150 CAG repeats. See, e.g., Mangiarini et al. (1996) *Cell* 87:493; Menalled (2005) *NeuroRx* 2:465; and Menalled and Chesselet (2002) *Trends Pharmacol. Sci.* 23:32; and Hodgson et al. (1999) *Neuron* 23:181.

Suitable non-human animal models of amyotrophic lateral sclerosis (ALS) include spontaneously-occurring mouse models (e.g., the motor neuron degeneration (Mnd) model; the progressive motor neuropathy (Pmn) model; and wobbler); transgenic mouse models (e.g., a transgenic mouse that overexpresses the mutated SOD1 gene of familial ALS patients; the neurofilament transgenic mouse; a transgenic mouse comprising a mutation in the TAR DNA binding protein-43 (TDP-43) gene identified in some ALS patients; a transgenic mouse with neuron-specific expression of Bicaudal D2 N-terminus (BICD2-N), which chronically impairs dynein/dynactin function); and the like. See, e.g., Pioro and Mitsumoto (1995) *Clin. Neurosci.* 3:375; Price et al. (1997) *Rev. Neurol.* 153:484; and Wegorzewska et al. (2009) *Proc. Natl. Acad. Sci. USA* 106:18809; and Teuling et al. (2008) *Hum. Mol. Genet.* 17:2849.

Suitable non-human animal models of Alzheimer's disease (AD) include a transgenic mouse comprising a human amyloid precursor protein (hAPP) mutant transgene; a transgenic mouse comprising a presenilin1 or a presenilin2 transgene; and the like. See, e.g., Götz et al. (2004) *Mol. Psychiatry.* 9:664; Götz and Ittner (2008) *Nature Reviews* 9:532.

Suitable non-human animal models of multiple sclerosis include the Experimental Autoimmune Encephalitis (EAE) mouse models of MS. See, e.g., Owens (2006) *Adv. Neurol.* 98:77; Baker and Jackson (2007) *Adv. Clin. Neurosci. Rehab.* 6:12; and Steinman and Zamvil (2006) *Ann. Neurol.* 60:12.

A PKD1 modulator is administered to the non-human animal model, e.g., in an amount of from about 1 µg to about 100 µg or more. The effect of the PKD1 modulator on one or more parameters is assessed.

For example, the effect of the PKD1 modulator on cognitive function, muscle function, motor function, brain function, behavior, and the like, is assessed. Electrophysiological tests can be used to assess brain function. Muscle function can be assessed using, e.g., a grip strength test. Motor function can be tested using, e.g., a rotarod test. Cognitive functions can be tested using, e.g., the open field test, the elevated plus maze, the Morris water maze, the zero maze test, the novel objection recognition test, and the like. Tests for neurological functioning and behavior that include sensory and motor function, autonomic reflexes, emotional responses, and rudimentary cognition, can be carried out. Such tests are well known in the art; see, e.g., Chapter 12 "Assessments of Cognitive Deficits in Mutant Mice" by Rodriguiz and Wetsel, in "Animal Models of Cognitive Impairment" (2006) E. D. Levin and J. J. Buccafusco, eds. CRC Press, Boca Raton, Fla.

As another example, the effect of the PKD1 modulator on one or more of: a) protein deposition (e.g., Aβ and/or hyperphosphorylated tau in an AD model; α-synuclein and/or Lewy bodies in a PD model; neuronal aggregates in an ALS model; huntingtin with polyglutamine expansion in Huntington's disease; see e.g., Ross and Poirier (2004) *Nat. Med.* 10Suppl:S10); b) dystrophic neurites; c) microglial activation; d) reactive astrocyte formation; e) cell loss (e.g., neurons; glial cells, including microglia and astrocytes); etc., is assessed. The effect of the PKD1 modulator can be assessed histochemically, e.g., on brain tissue from the treated non-human animal model. Protein deposition can be assessed immunohistochemically. Cells, such as neurons and glial cells (including astrocytes and microglia) can be obtained from the treated non-human animal model and assessed in vitro. Protocols for detecting these pathologies are known in the art. See, e.g., *Greenfield's Neuropathology* S. Love, D. N. Louis, and D. W. Ellison (2008) 8$^{th}$ Ed. Oxford University Press.

A PKD1 modulator that, when administered to a suitable animal model, results in an improvement of at least one parameter associated with a neurodegenerative disease, is considered a candidate for treating the neurodegenerative disease.

Example 4

Generation and Characterization of PKD1-Deficient, hAPP-FAD Transgenic Mouse Lines Evaluating how deletion of PKD1 affects phenotypes in well-established animal models of disease is a powerful strategy for assessing therapeutic potential of PKD1 inhibitors. Towards this end, three new mouse lines were developed: PKD1$^{fl/fl}$+J20, PKD1$^{fl/fl}$×Nestin::Cre+J20, and PKD1$^{fl/fl}$×CamKII::Cre+J20. J20 is a transgenic mouse line that expresses moderate levels of hAPP with Indiana and Swedish FAD-associated mutations. Additionally, J20 mice show AD-like histopathological, behavioral, and electrophysiological abnormalities (Mucke et al. (2000) infra; Harris et al. (2010) *J Neurosci* 30:372-381). Altered time-course or severity of symptoms in J20 mice lacking PKD1 provides evidence of the kinase's role in the pathogenesis of AD, and informs a therapeutic strategy for delivery of drugs targeting PKD1.

Materials and Methods

Electrophysiology

Animals.

All animal procedures were approved by the University of California, San Francisco Institutional Animal Care and use Committee. The mouse lines used to generate these animals were: 1) PKD1$^{fl/fl}$ (Fielitz et al. (2008) Proc Natl Acad Sci USA 105:3059-3063); 2) CamKII::Cre (Xu et al. (2000) *J Neurosci* 20:6888-6897); and 4) J20 (Mucke et al. (2000) *J Neurosci* 20:4050-4058). Hemizygous J20 mice were crossed with PKD1$^{fl/fl}$ mice. PKD1$^{wt/fl}$+J20 animals were subsequently bred with PKD1$^{fl/fl}$ to generate a PKD1$^{fl/fl}$+J20 line. A final cross of PKD1$^{fl/fl}$+J20 with PKD1$^{fl/fl}$×CamKII::Cre mice was performed to produce the animals used in this study.

Slice Preparation and Data Acquisition.

2.5-4 month old mice were anesthetized using inhaled isofluorane and rapidly decapitated into ice cold sucrose-artificial CSF (aCSF) with 1 mM ascorbic acid (in mM: 252 sucrose, 2.5 KCl, 7 MgCl$_2$, 0.4 CaCl$_2$, 20 glucose, and 25 NaHCO$_3$, pH 7.4). Transverse horizontal slices (300-400 µM) were taken at throughout the entire dorsoventral extent of the hippocampus (4-6 slices per animal) and transferred to a perfusion chamber with normal aCSF (in mM: 125 NaCl, 2.5 KCl, 1 MgCl$_2$, 2.5 CaCl$_2$, 20 glucose, and 25 NaHCO$_3$, pH 7.4) containing 1 mM ascorbic acid. Slices were equilibrated for at 34° C. for 30 min and then returned to room temperature for another 30 min prior to recording. During recording, slices received constant bath perfusion of normal aCSF heated to 34° C. with an inline heater. Solutions were constantly bubbled with 95% O$_2$/5% CO$_2$. Data were acquired using a Multiclamp 700B amplifier (Molecular Devices) (2 kHz low-pass Bessel filter) and digitized (10 kHz sampling rate) with an ITC-18 Computer Interface digitizer (Instrutech). Data were analyzed using custom software written for IGOR Pro (WaveMetrics).

Whole-Cell Patch Clamp Recordings.

Whole-cell patch clamp recordings were made from CA1 pyramidal neurons using borosilicate electrodes (3-6MΩ) containing (in mM: 117 CsMeSO$_4$, 20 HEPES, 0.4 EGTA, 2.8 NaCl, 2.5 ATP, 0.25 GTP, 5 tetraethylammonium-C1, and 20 glucose; pH 7.4; mOsm 280-290). For analysis of miniature postsynaptic currents (mEPSCs), cells were held at −80 mV and 1 µM tetrodotoxin and 20 µM bicuculline (TTX; Tocris, Minn., USA) were included in the external solution. In all experiments, series resistance (<25MΩ) was monitored and corrected.

Field Recordings.

Field excitatory postsynaptic potentials (fEPSPs) were recorded using borosilicate glass electrodes (~3MΩ) filled with 1M NaCl and 25 mM HEPES, pH 7.3. Potentials were evoked with square current pulses delivered using bipolar (contact spacing 115 uM) tungsten electrodes (FHC) placed in the stratum radiatum at the CA1/CA3 border. Recording electrodes were placed 150-300 µM away in CA1 stratum radiatum. The fEPSC input/output (i/o) relationship was determined by administering a range of stimulus intensities (15 to 800 µA) at 0.067 Hz. Following i/o measurements, paired-pulse ratios (PPRs) were obtained by delivering stimulus pairs at a 50 ms latency. PPR values were generated by taking the ratio of fEPSP slope 2/fEPSP slope 1.

Statistical Analysis

Unpaired t-tests, One-way ANOVA, Two-way ANOVA and post-hoc Tukey's tests were performed using Prism 6 (GraphPad).

Results

Network dysfunction and synapse loss have been identified as pathological features of AD (Minoshima et al. (1997) Ann Neurol 42:85-94; Sperling et al. (2009) Neuron 63:178-188). Understanding how these changes contribute to AD symptoms and identifying their underlying molecular mechanisms could promote discovery of novel targets for AD drugs. Line J20 mice are a model of FAD and show reduced efficacy at hippocampal synapses as early as 2 months of age (Harris et al. (2010) supra). To evaluate if PKD knockout affects this synaptic dysfunction, acute brain slices were taken from PKD1$^{fl/fl}$, PKD1$^{fl/fl}$+J20, PKD1$^{fl/fl}$×CamKII::Cre, and PKD1$^{fl/fl}$×CamKII::Cre+J20 mice; and mEPSCs and fEPSPs were measured in CA1 pyramidal neurons and their dendritic fields.

Figure 19:
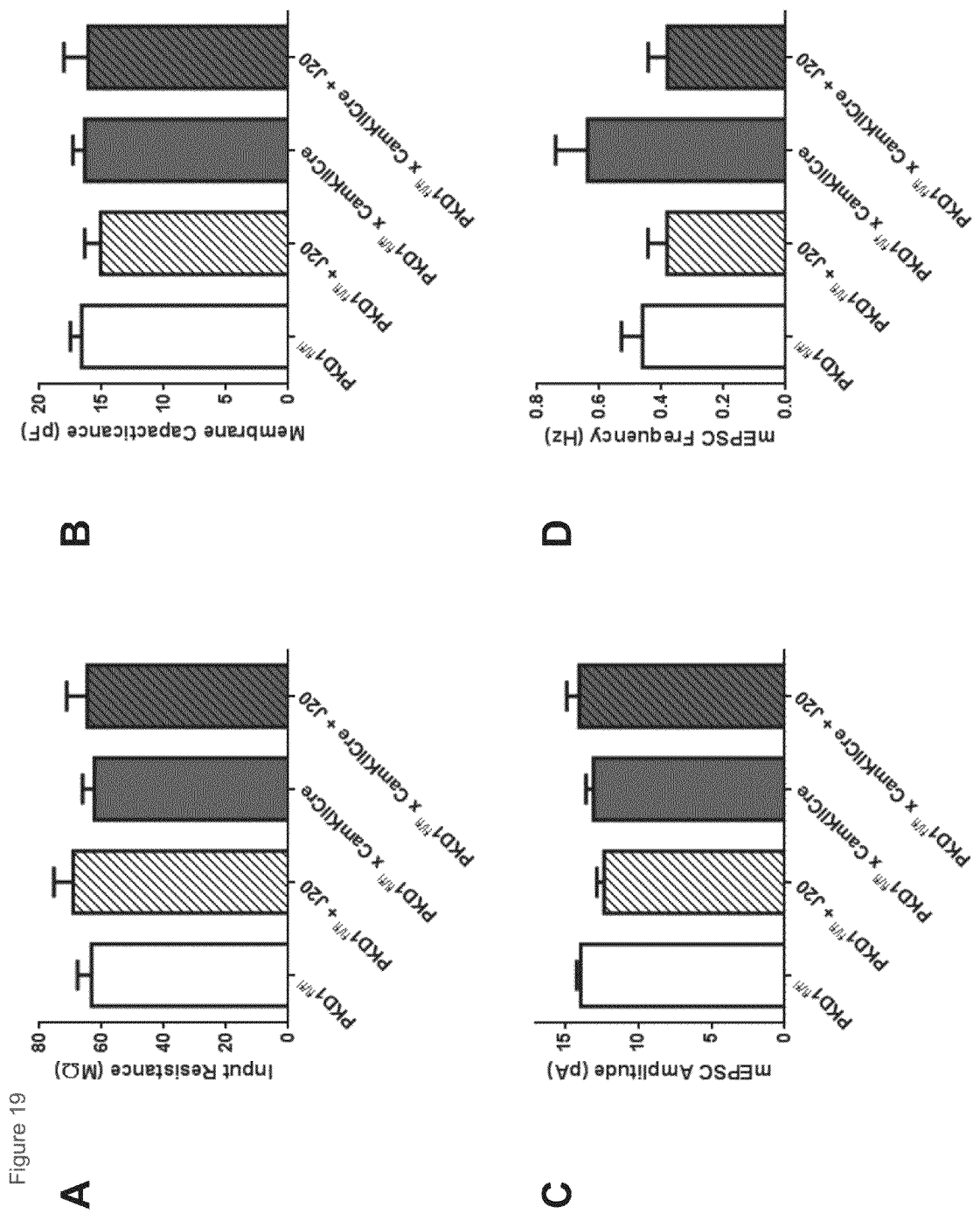
FIGS. 19A-D depict the effect of PKD1 deletion on membrane resistance, membrane capacitance, miniature postsynaptic current (mEPSC) amplitude, and mEPSC frequency.
Figure 20:
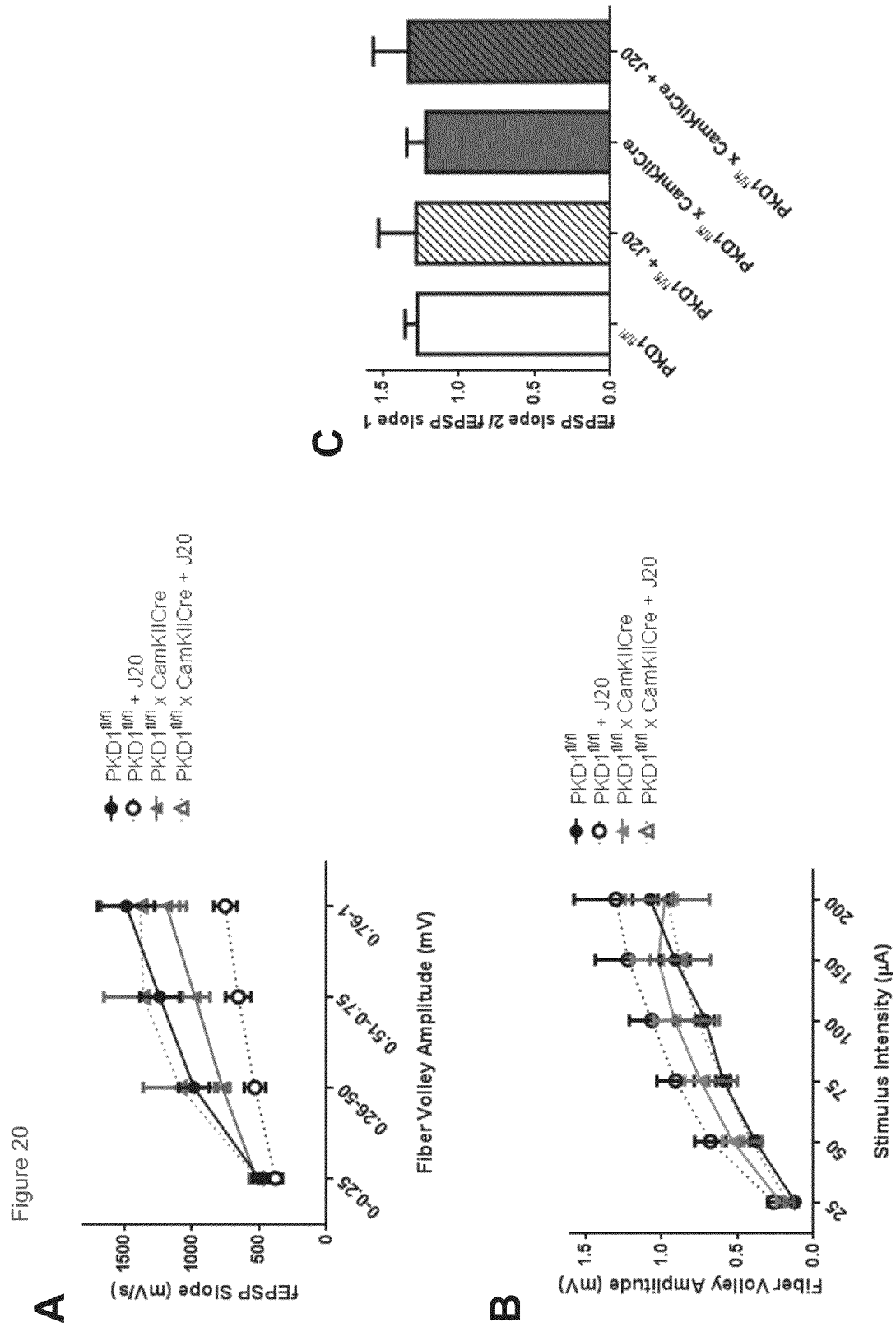
FIGS. 20 A-C depict the effect of PKD1 deletion on field excitatory postsynaptic potentials (fEPSPs) in mice not transgenic for hAPP$^{FAD}$ and in mice transgenic for hAPP$^{FAD}$.

Membrane resistance (FIG. 19A) and capacitance (FIG. 19B) were not different between any of the groups tested. No significant group differences in event amplitude or frequency were detected from mEPSC measurements from these cells (FIGS. 19C and 19D).

fEPSP recordings in PKD1$^{fl/fl}$ slices had a much greater postsynaptic response to stimulation than those from PKD1$^{fl/fl}$+J20 mice (p=0.008). Interestingly, PKD1$^{fl/fl}$×CamKII::Cre+J20 slices also had larger fEPSP response than PKD1$^{fl/fl}$+J20 (p=0.002), suggesting that loss of PKD1 mitigates this effect of hAPP expression on synaptic function (FIG. 20A). Fiber volley amplitude as a function of stimulus intensity was higher in PKD1$^{fl/fl}$+J20 mice compared to PKD1$^{fl/fl}$ (p=0.002) (FIG. 20B). This indicates that Schaffer collaterals of J20 mice are hyperexcitable. This relationship was also lower in PKD1$^{fl/fl}$×CamKII::Cre+J20 slices than PKD1$^{fl/fl}$+J20 slices (p=0.007) (FIG. 20B), suggesting a role for PKD1 in this phenotype. 50 ms PPR measurements, a test of neurotransmitter release probability, did not differ between any of the groups tested (FIG. 20C).

Example 5

PKD1 is Abnormally Phosphorylated in Mouse Models of Huntington'S Disease and Alzheimer's Disease Materials and Methods All animal procedures were approved by the University of California, San Francisco Institutional Animal Care and use Committee.

Forebrains of mice were lysed in a Dounce homogenizer with ice-cold RIPA buffer (1% Triton X-100, 0.1% SDS, 50 mM Tris-HCl, 150 mM NaCl, 1 mM EDTA, 10 mM NaF, and protease inhibitor cocktail; Roche). Samples were centrifuged, and supernatants were loaded onto gels, separated by SDS-PAGE, transferred to PVDF membranes, and probed with antibodies against pan-PKD1 (1:1000, Cell Signaling), phospho-S916 PKD1 (1:1000, Cell Signaling), β-actin (1:4000, Sigma). Anti-rabbit or anti-mouse secondary antibodies conjugated to horseradish peroxidase were used on all blots and imaged by enhanced chemiluminescence (Amersham Biosciences) or with SuperSignal West Femto substrate (Pierce).

Results

Protein kinase D1 (PKD1) kinase activity is correlated with its phosphorylation on specific sites: protein kinase C phosphorylates PKD1 serines 744/8 (pS744/8) to initiate PKD1 activity, after which PKD1 phosphorylates itself at serine 916 (pSer916). Thus PKD1 kinase activity can be assessed in cells or tissues by measuring levels of PKD1 pS744/8 or pSer916 by western blot.

Figure 21:
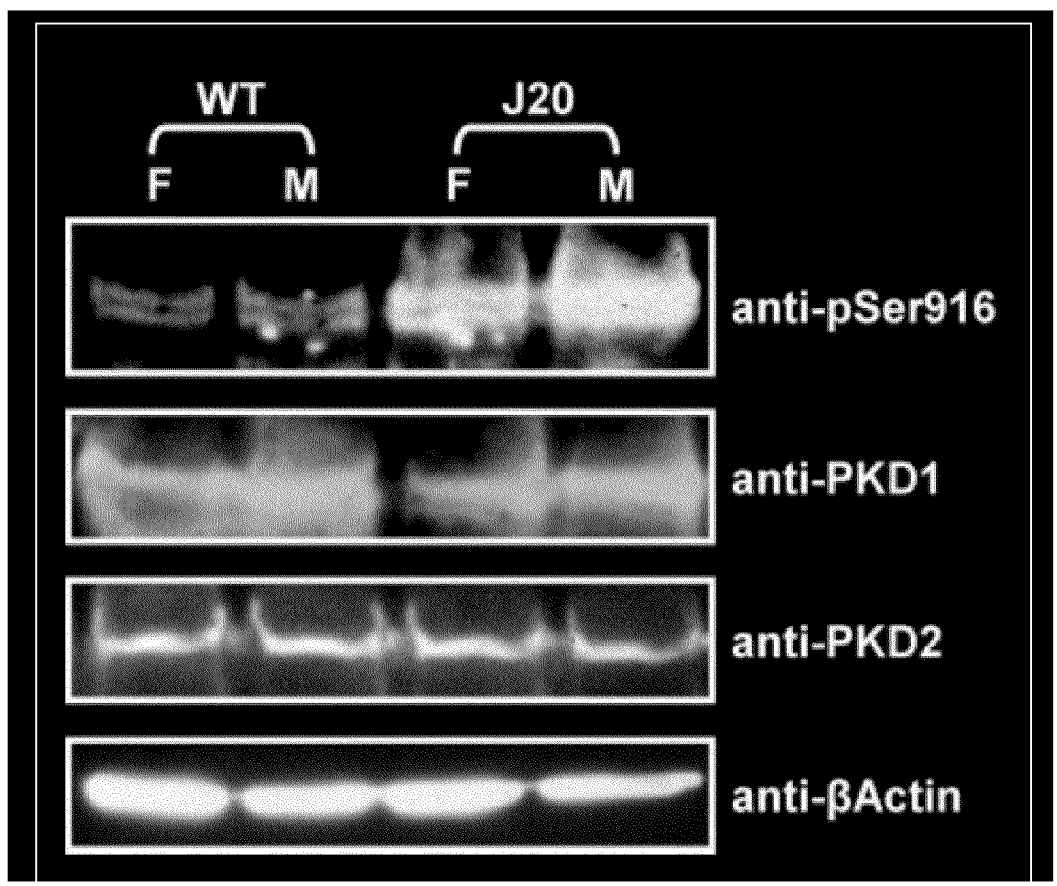
FIG. 21 depicts Western blot analysis of forebrain lysate of 6-month-old J20 mice and wild type (WT) littermate controls.

To determine if PKD1 kinase activity was abnormal in a mouse model of Alzheimer's disease, forebrain lysate was collected from 6 month old J20 mice (Mucke et al. (2000) J. Neurosci. 20:4050) or control littermates and probed with antibodies against pSer916, PKD1, PKD2. Actin served as a loading control to ensure equal amounts of protein were loaded in all conditions. While PKD1 levels were the same in J20 and control mice, J20 forebrain lysate showed in increase in p916 (FIG. 21), indicating J20 mice have increased PKD1 kinase activity in their forebrains compared to wild type animals.

Figure 22:
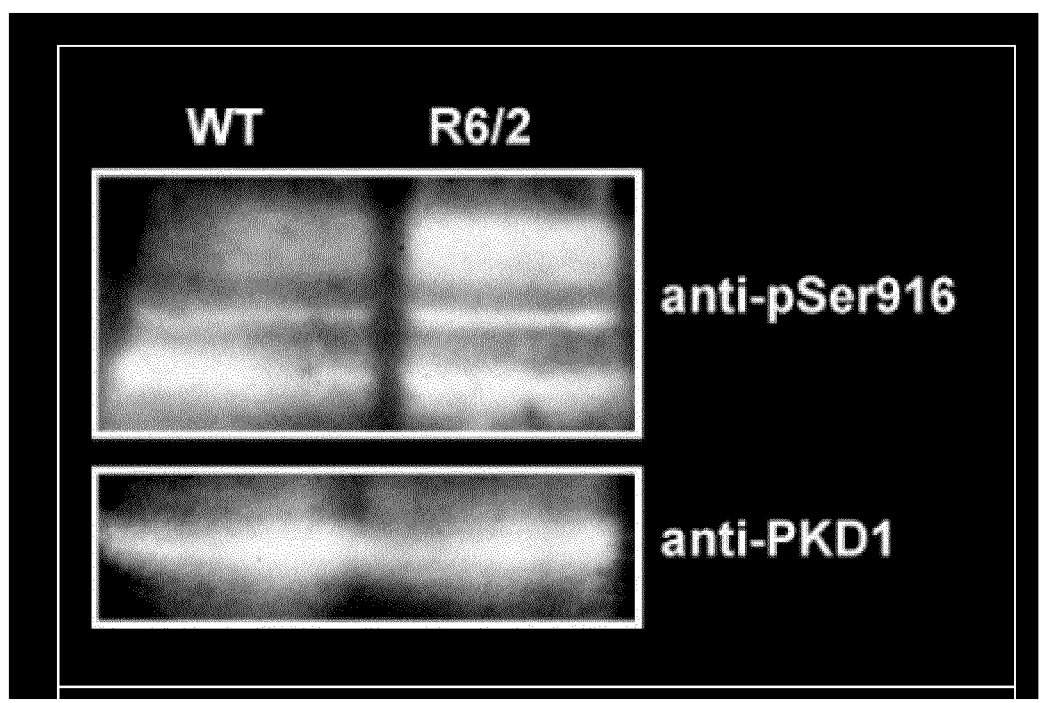
FIG. 22 depicts Western blot analysis of forebrain lysate of 13-week-old R6/2 mice and wild-type littermate controls.

To determine if PKD1 kinase activity was abnormal in a mouse model of Huntington's disease, forebrain lysate was collected from 13 week old R6/2 mice (Mangiarini et al. (1996) Cell 87:493) or control littermates and probed with antibodies against pSer916 and PKD1. Total PKD1 levels were the same between R6/2 and control forebrain, but the R6/2 sample had a higher pSer916 signal (FIG. 22), suggesting PKD1 kinase activity was up-regulated in the brain R6/2 mice.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A method for treating a neurodegenerative disease in an individual, the method comprising administering to the individual an effective amount of an inhibitory nucleic acid that reduces the level of active protein kinase D1 (PKD1) in a neuronal cell and/or a glial cell in the individual, wherein the neurodegenerative disease is Huntington's disease or Alzheimer's disease.

2. The method of claim 1, wherein the inhibitory nucleic acid comprises an antisense region that is complementary to a nucleotide sequence in a target PKD1-encoding nucleic acid.

3. The method of claim 2, wherein the agent is an inhibitory nucleic acid comprises an antisense region that is complementary to a PKD1 target sequence from SEQ ID NOs: 17-21.

4. The method of claim 1, wherein the inhibitory nucleic acid comprises one or more chemical modifications that increase stability.

5. The method of claim 1, wherein the inhibitory nucleic acid is formulated with a lipid.

* * * * *